US008609024B2

(12) United States Patent
Ronsick et al.

(10) Patent No.: US 8,609,024 B2
(45) Date of Patent: Dec. 17, 2013

(54) SYSTEM AND METHOD FOR AUTOMATICALLY VENTING AND SAMPLING A CULTURE SPECIMEN CONTAINER

(75) Inventors: Christopher S. Ronsick, Durham, NC (US); Mark S. Wilson, Hillsborough, NC (US); Ronnie J. Robinson, St. Charles, MI (US)

(73) Assignee: Biomerieux, Inc., Durham, NC (US)

( * ) Notice: Subject to any disclaimer, the term of this patent is extended or adjusted under 35 U.S.C. 154(b) by 315 days.

(21) Appl. No.: 12/800,396

(22) Filed: May 14, 2010

(65) Prior Publication Data

US 2010/0291615 A1    Nov. 18, 2010

Related U.S. Application Data

(60) Provisional application No. 61/216,339, filed on May 15, 2009.

(51) Int. Cl.
*B32B 5/02* (2006.01)
*G01N 35/02* (2006.01)

(52) U.S. Cl.
USPC ............... 422/63; 422/65; 422/400; 422/404; 422/67

(58) Field of Classification Search
None
See application file for complete search history.

(56) References Cited

U.S. PATENT DOCUMENTS

| | | |
|---|---|---|
| 4,192,919 A | 3/1980 | Raghavachari |
| 4,212,948 A | 7/1980 | Dorn |
| 4,927,545 A | 5/1990 | Roginski |
| 4,928,539 A | 5/1990 | Champseix et al. |
| 5,035,865 A | 7/1991 | Inaba et al. |
| 5,260,872 A | 11/1993 | Copeland et al. |
| 5,371,016 A | 12/1994 | Berndt |
| 5,411,065 A | 5/1995 | Meador et al. |
| 5,432,061 A | 7/1995 | Berndt |
| 5,443,791 A | 8/1995 | Cathcart et al. |

(Continued)

FOREIGN PATENT DOCUMENTS

| | | |
|---|---|---|
| FR | 2888328 | 1/2007 |
| WO | 2008/107881 | 9/2008 |
| WO | 2009/049171 | 4/2009 |
| WO | 2009/100197 | 8/2009 |

OTHER PUBLICATIONS

International Search Report for PCT/US2010/034987.

(Continued)

*Primary Examiner* — Sally Merkling
(74) *Attorney, Agent, or Firm* — McDonnell Boehnen Hulbert & Berghoff LLP

(57) ABSTRACT

Apparatus for automated venting and/or sampling of a specimen container is disclosed. The apparatus includes a rack holding the specimen container; a venting and/or sampling device having a needle, a chamber in fluid communication with the needle and a port in fluid communication with the chamber; a robotic transfer mechanism moveable relative to the rack; a sample removal apparatus attached to the robotic transfer mechanism having gripping features for gripping the venting device. The sample removal apparatus and robotic transfer mechanism are moveable relative to the specimen container so as to automatically insert the needle of the venting device through the closure of the specimen container to thereby vent the interior of the specimen container and obtain equilibrium between the interior of the specimen container and the atmosphere and withdraw a portion of the sample from the specimen container into the venting and/or sampling device.

9 Claims, 40 Drawing Sheets

(56) References Cited

U.S. PATENT DOCUMENTS

| | | | |
|---|---|---|---|
| 5,474,910 A | 12/1995 | Alfano | |
| 5,479,969 A * | 1/1996 | Hardie et al. | 141/130 |
| 5,516,692 A | 5/1996 | Berndt | |
| 5,525,298 A | 6/1996 | Anami | |
| 5,635,348 A | 6/1997 | Leong | |
| 5,665,309 A | 9/1997 | Champseix et al. | |
| 5,705,384 A | 1/1998 | Berndt | |
| 5,869,329 A | 2/1999 | Berndt | |
| 5,938,617 A | 8/1999 | Vo-Dinh | |
| 5,948,610 A | 9/1999 | Ho et al. | |
| 6,060,022 A | 5/2000 | Pang et al. | |
| 6,077,481 A | 6/2000 | Ichida et al. | |
| 6,122,396 A | 9/2000 | King et al. | |
| 6,293,750 B1 | 9/2001 | Cohen et al. | |
| 6,346,421 B1 | 2/2002 | Anderson et al. | |
| 6,544,799 B1 | 4/2003 | Lewis et al. | |
| 6,592,324 B2 | 7/2003 | Downs et al. | |
| 6,673,595 B2 | 1/2004 | Barbera-Guillem | |
| 6,793,887 B2 | 9/2004 | Itoh | |
| 6,834,237 B2 | 12/2004 | Noergaard et al. | |
| 7,070,739 B1 | 7/2006 | Anderson et al. | |
| 7,141,213 B1 | 11/2006 | Pang et al. | |
| 7,229,820 B2 * | 6/2007 | Wilson | 435/284.1 |
| 7,374,720 B2 | 5/2008 | Toi et al. | |
| 7,462,323 B1 * | 12/2008 | Chang et al. | 422/68.1 |
| 2004/0068193 A1 | 4/2004 | Barnes et al. | |
| 2004/0197771 A1 | 10/2004 | Powers et al. | |
| 2005/0009123 A1 | 1/2005 | Goodnow | |
| 2005/0037408 A1 | 2/2005 | Christensen et al. | |
| 2006/0024211 A1 * | 2/2006 | Giter et al. | 422/104 |
| 2006/0216199 A1 | 9/2006 | Koike | |
| 2006/0263250 A1 * | 11/2006 | Blouin et al. | 422/63 |
| 2007/0037135 A1 | 2/2007 | Barnes et al. | |
| 2007/0184546 A1 * | 8/2007 | Farrelly et al. | 435/286.3 |
| 2007/0269897 A1 | 11/2007 | Tanaka et al. | |
| 2008/0090268 A1 | 4/2008 | Aygen | |
| 2008/0240898 A1 | 10/2008 | Manz et al. | |
| 2008/0261263 A1 | 10/2008 | Allardyce et al. | |
| 2009/0004063 A1 | 1/2009 | Higashihara et al. | |
| 2009/0142844 A1 | 6/2009 | Le Comte | |

OTHER PUBLICATIONS

The Written Opinion of the International Searching Authority for PCT/US2010/034987.

International Search Report for PCT/US2010/034956.

The Written Opinion of the International Searching Authority for PCT/US2010/034956.

Co-pending U.S. Appl. No. 12/800,467 "System for rapid noninvasive detection of a microbial agent in a biological sample and identifying and/or characterizing the microbial agent" filed May 14, 2010.

Co-pending U.S. Appl. No. 12/800,387, titled "Methods for Rapid Identification and/or Characterization of a Microbial Agent in a Sample," filed May 14, 2010.

Co-pending U.S. Appl. No. 12/800,388, titled "System for rapid identification and/or characterization of a microbial agent in a sample," filed May 14, 2010.

* cited by examiner

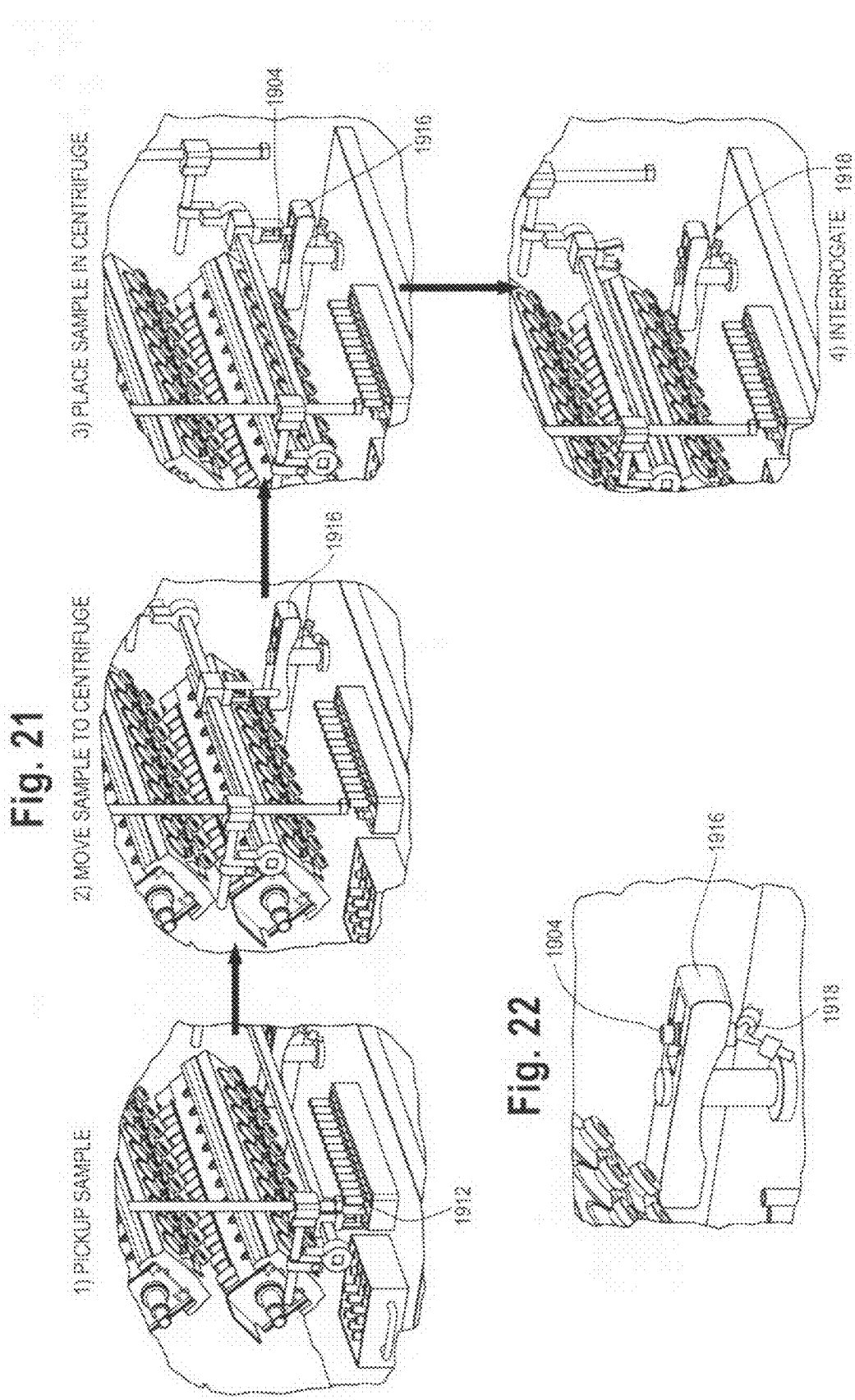

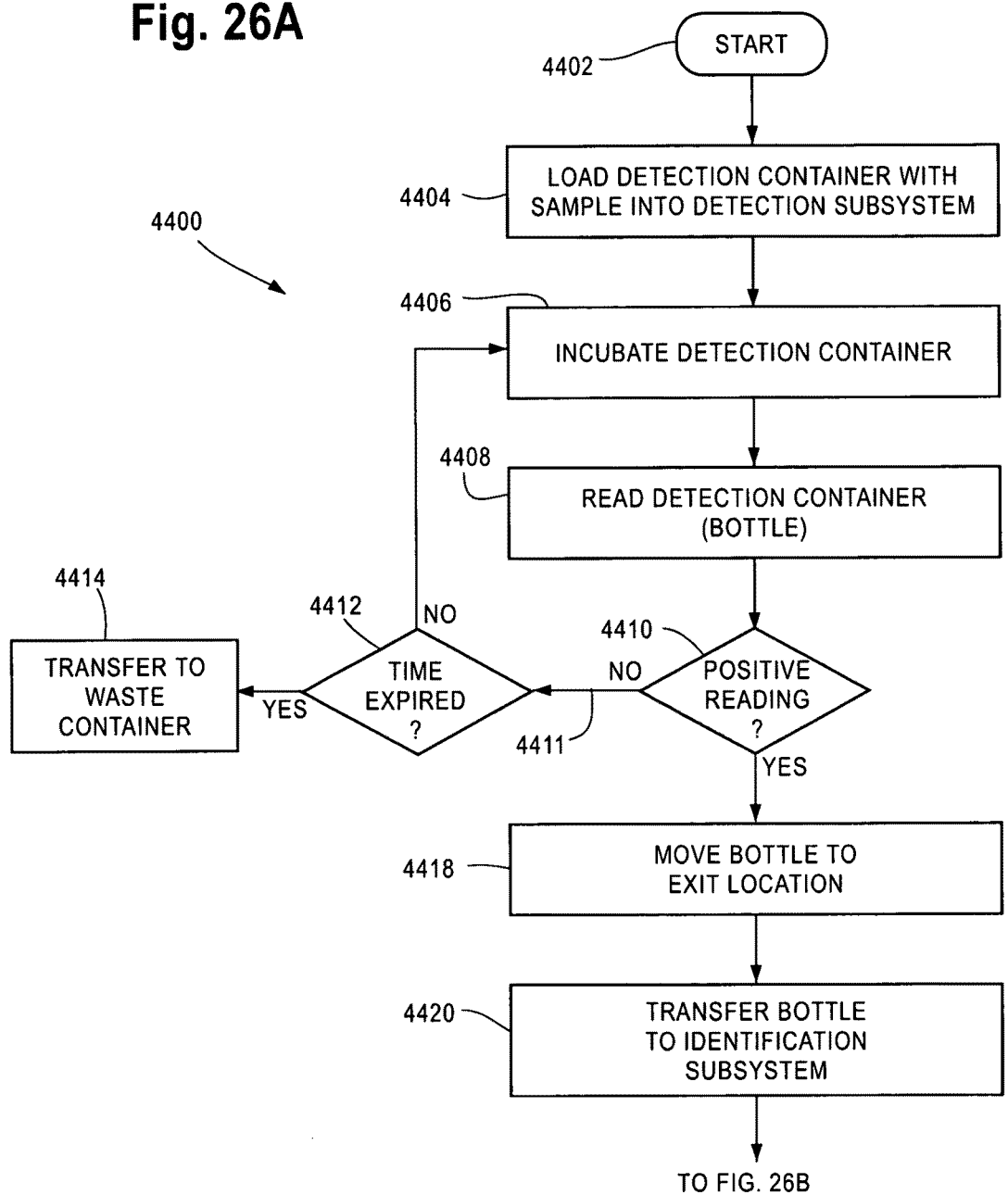

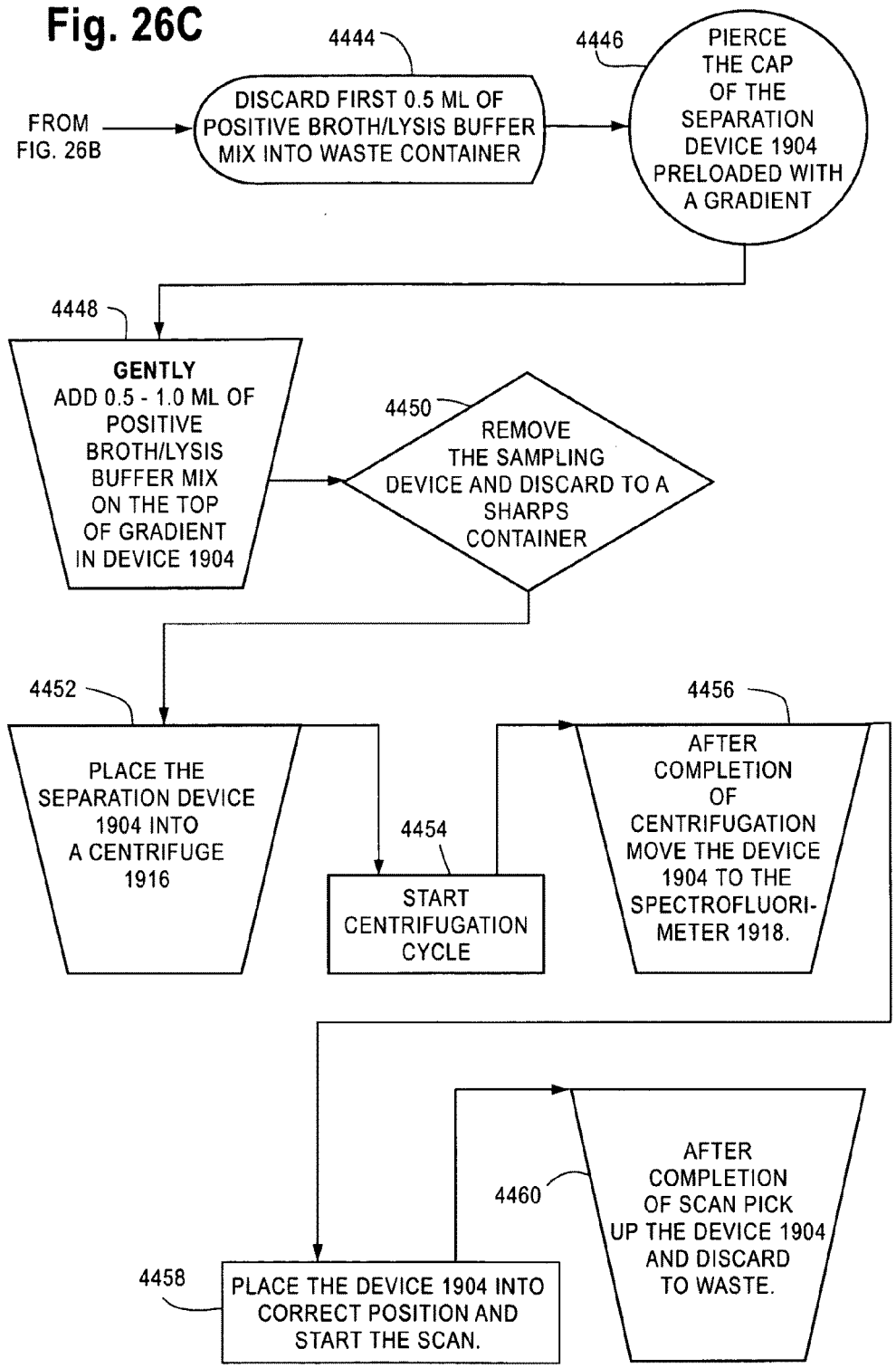

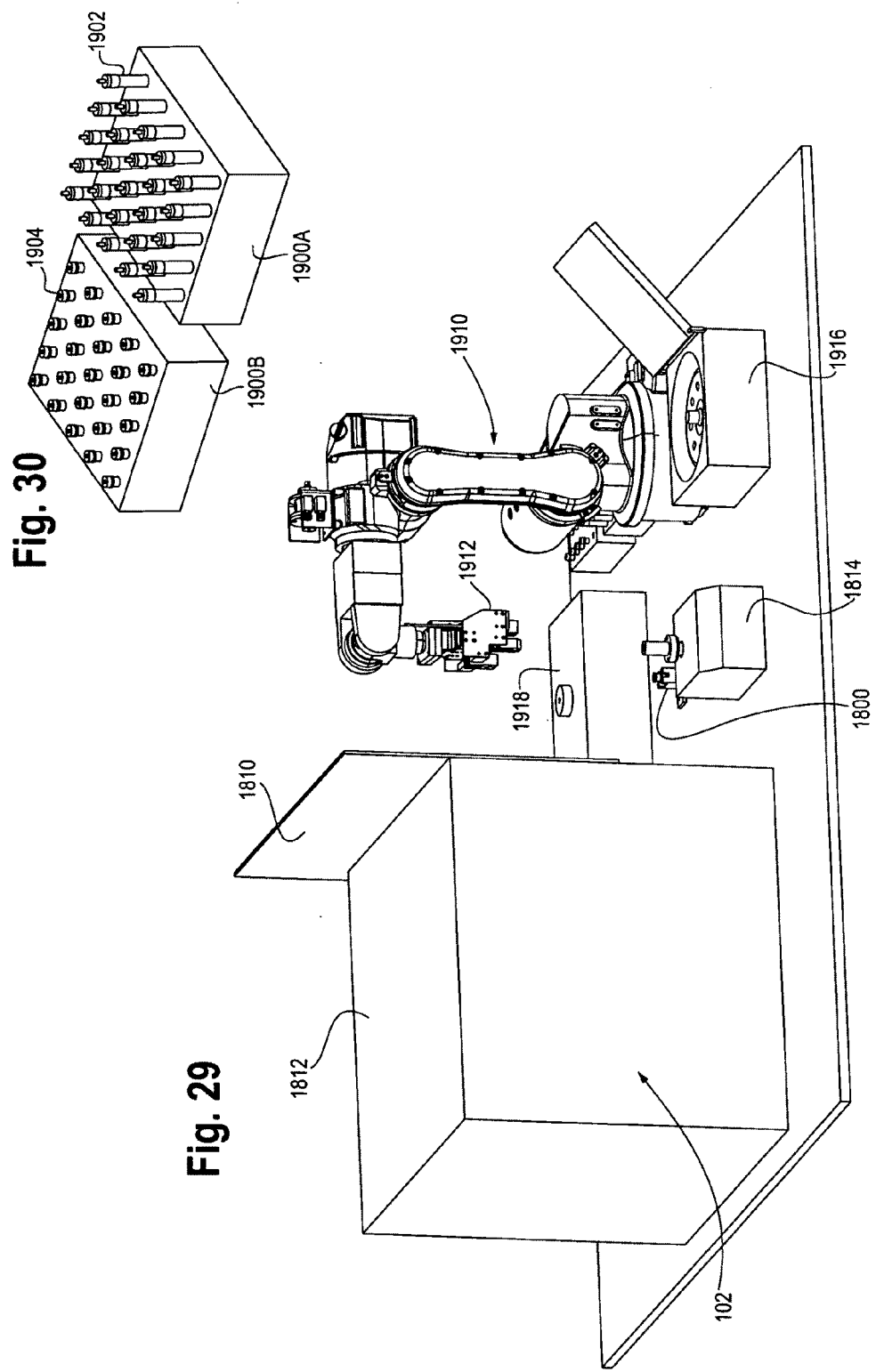

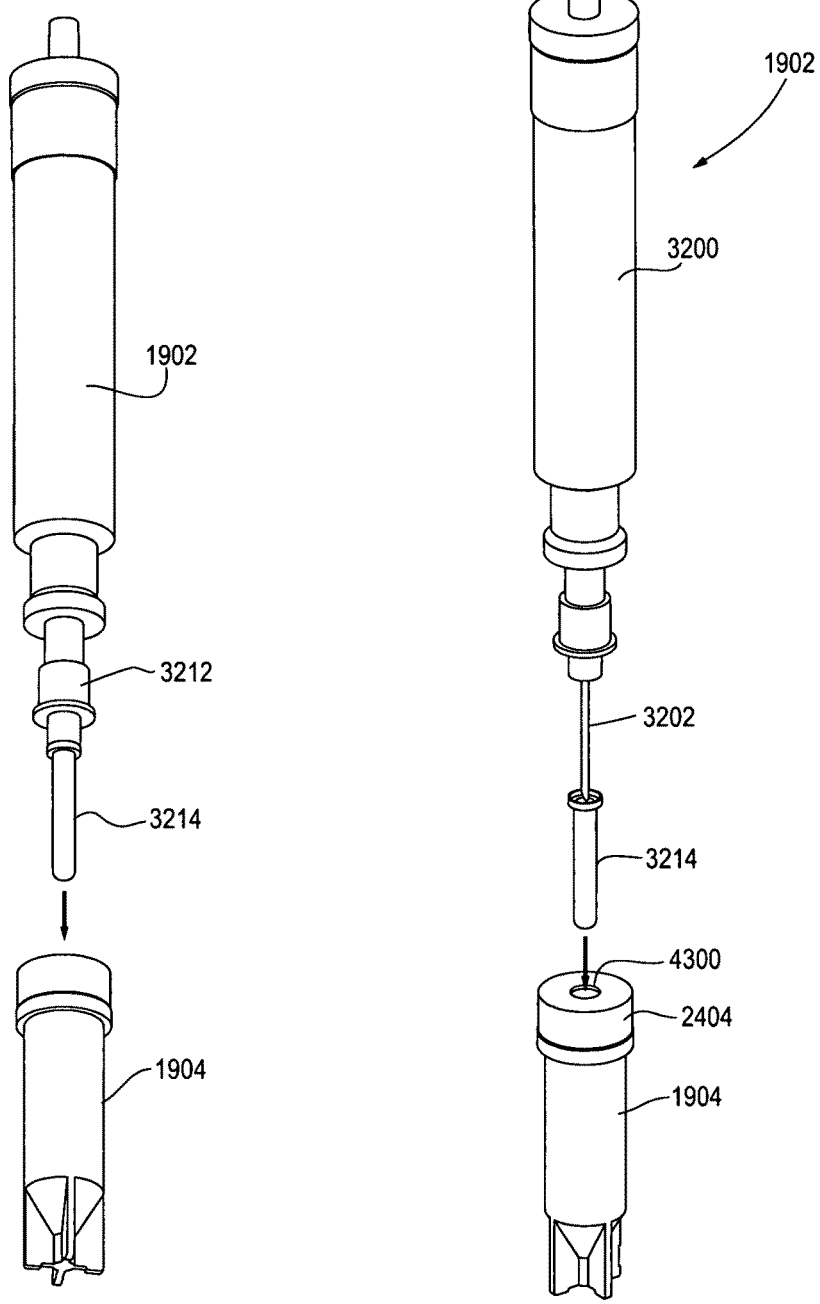

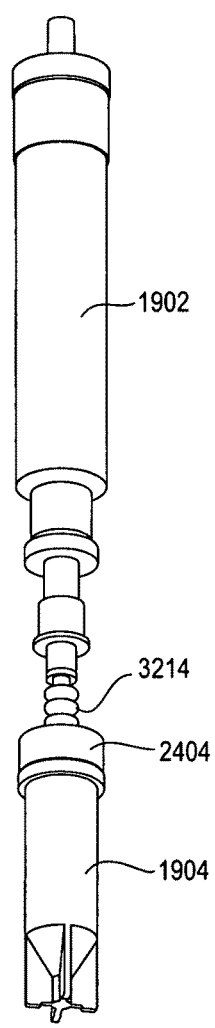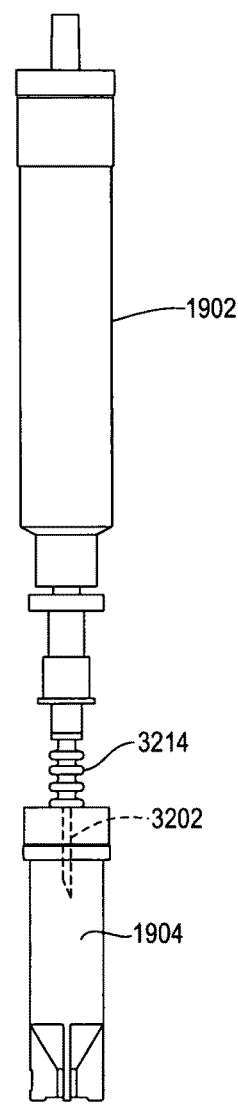

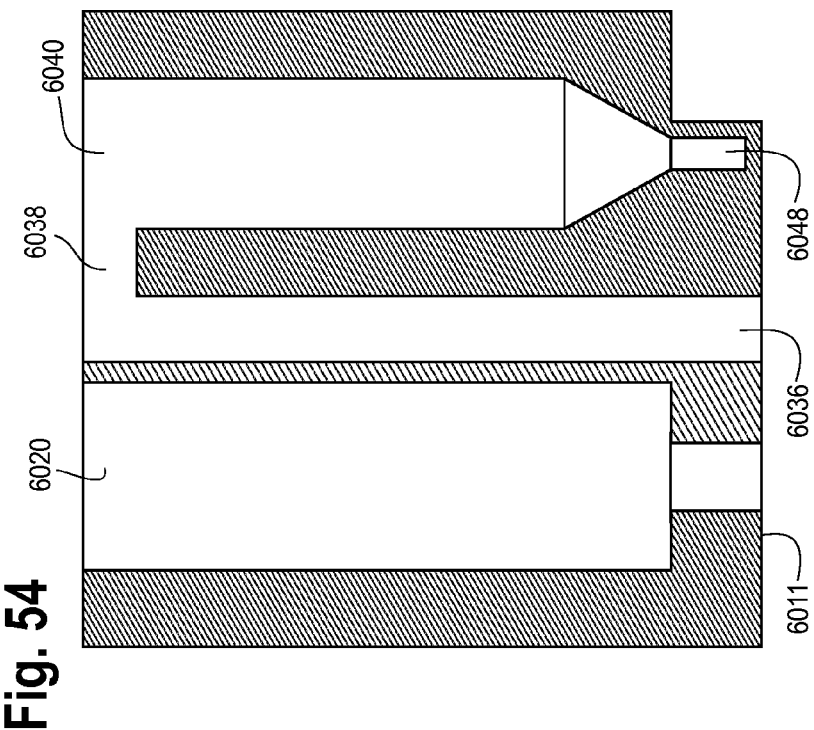
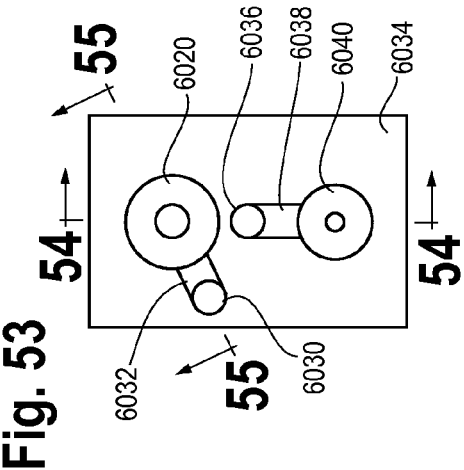
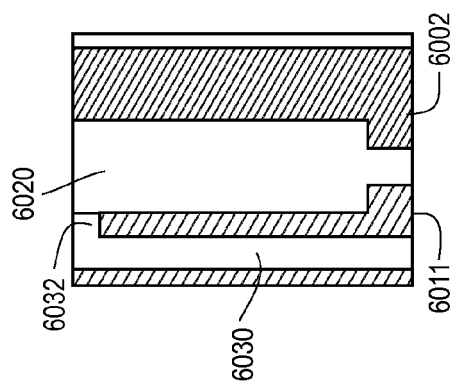

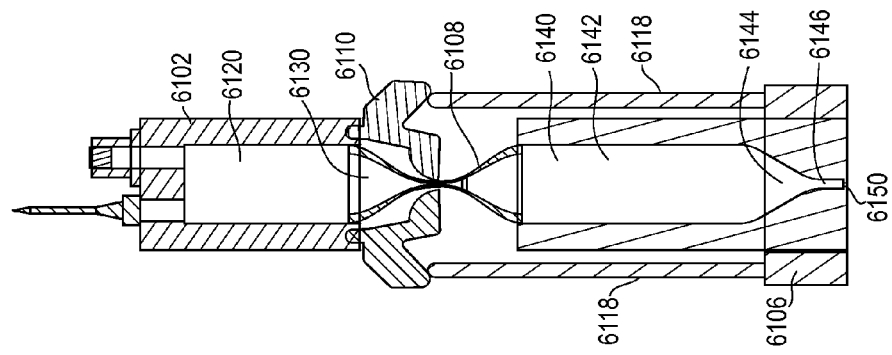
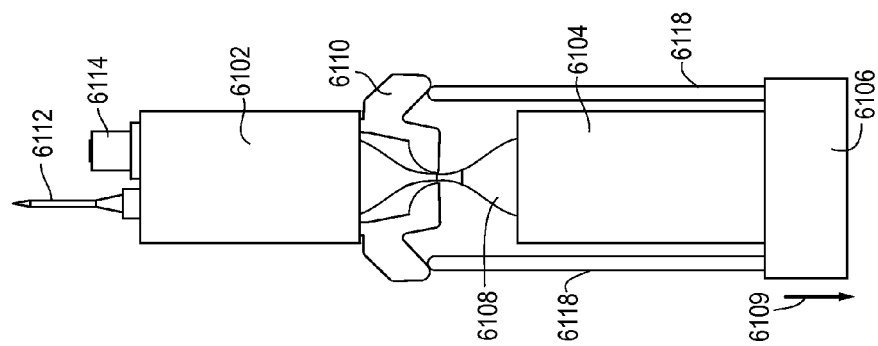
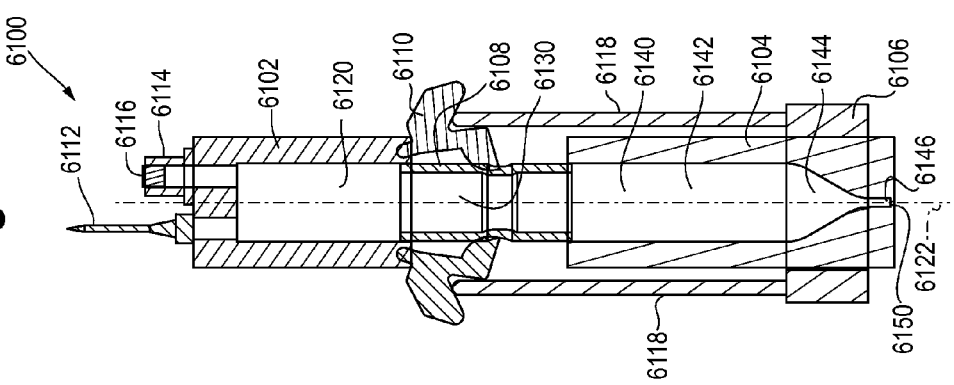
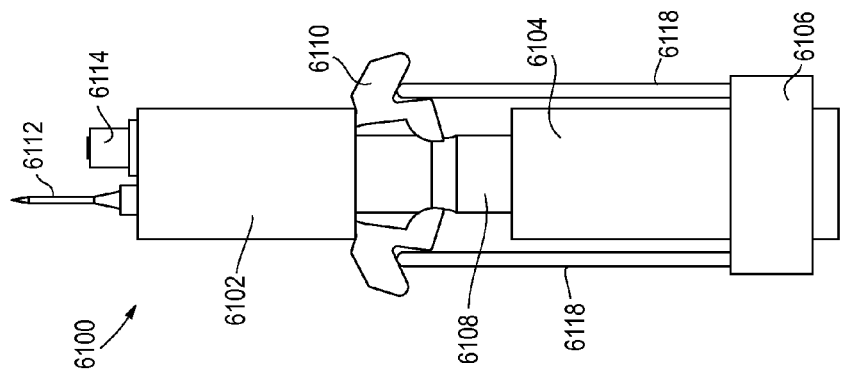

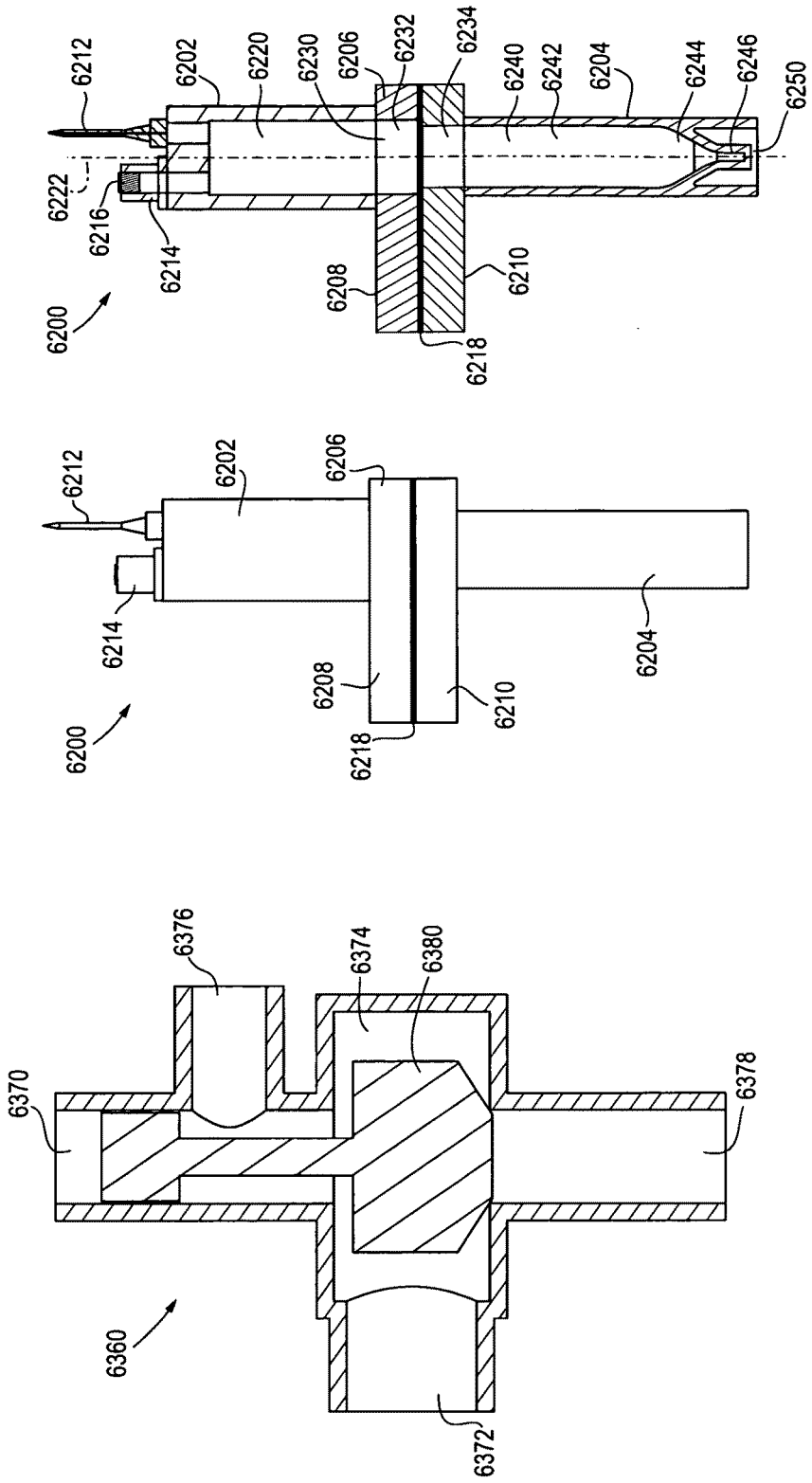

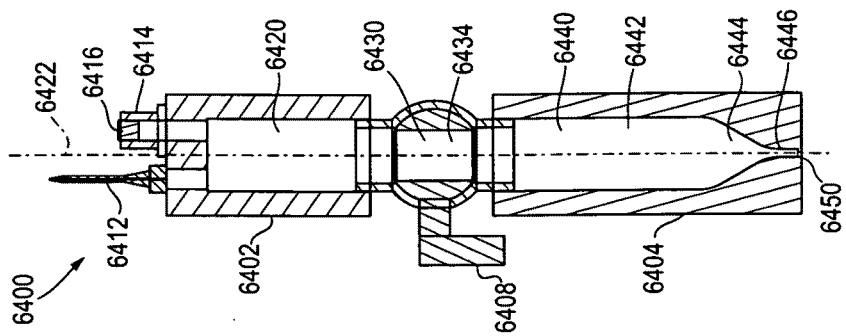
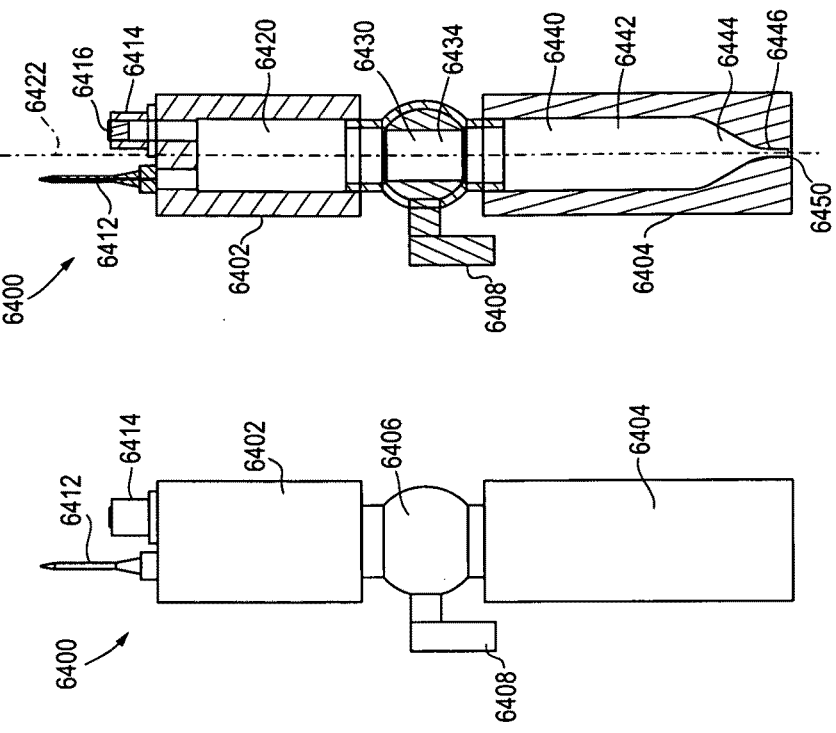
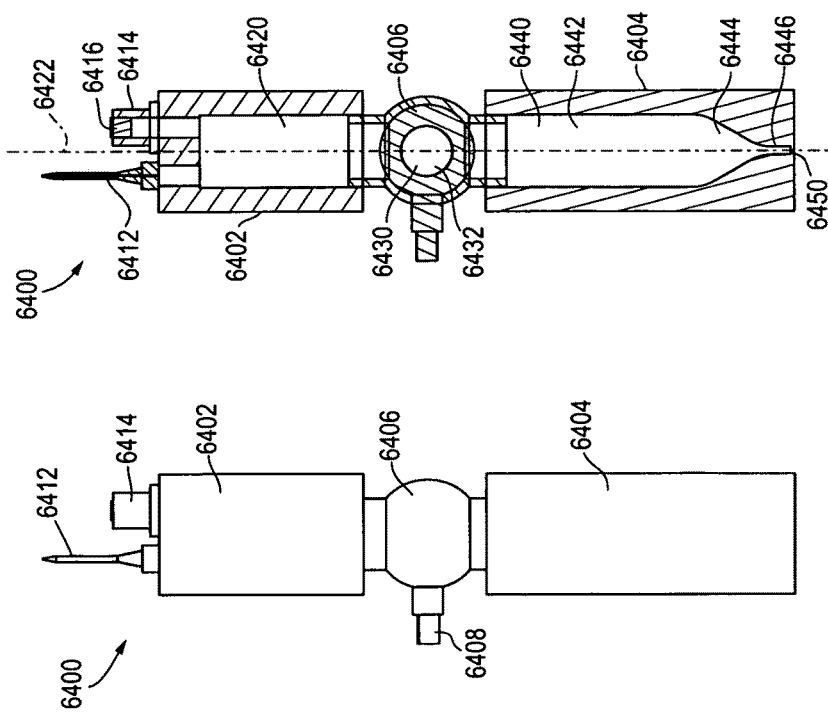

SYSTEM AND METHOD FOR AUTOMATICALLY VENTING AND SAMPLING A CULTURE SPECIMEN CONTAINER

CROSS-REFERENCE TO RELATED APPLICATIONS

This application claims priority under 35 U.S.C. §119(e) to U.S. provisional application Ser. No. 61/216,339 filed May 15, 2009, the content of which is incorporated by reference herein.

This application is also related to the following applications filed on the same date as this application, the content of which is incorporated by reference herein:

Ser. No. 12/800,387, entitled "Methods for rapid identification and/or characterization of a microbial agent in a sample."

Ser. No. 12/800,388, entitled "System for rapid identification and/or characterization of a microbial agent in a sample."

Ser. No. 12/800,467, entitled "System for rapid detection of a microbial agent in a sample and identifying and/or characterizing the microbial agent."

STATEMENT OF FEDERALLY SPONSORED RESEARCH

Not applicable.

BACKGROUND

This invention is directed to automated methods and apparatus for obtaining a sample from a specimen container used to culture a sample and for venting the container to atmosphere.

Instruments currently exist on the market in the U.S. that detect the growth and therefore the presence of a microorganism in a blood sample. One such instrument is the BacT/ALERT 3D instrument of the present assignee bioMérieux, Inc. The instrument receives a blood culture bottle containing a blood sample, e.g., from a human patient. The instrument incubates the bottle. Periodically during incubation an optical detection unit in the incubator analyzes a colorimetric sensor incorporated into the bottle to detect whether microbial growth has occurred within the bottle. The optical detection unit, specimen containers and sensors are described in the patent literature, see U.S. Pat. Nos. 4,945,060; 5,094,955; 5,162,229; 5,164,796; 5,217,876; 5,795,773; and 5,856,175, the entire content of each of which is incorporated by reference herein. Other prior art of interest relating generally to the detection of microorganisms in a biological sample includes the following patents: U.S. Pat. Nos. 5,770,394, 5,518,923; 5,498,543, 5,432,061, 5,371,016, 5,397,709, 5,344,417, 5,374,264, 6,709,857; and 7,211,430.

In detection instruments such as the BacT/ALERT 3D and similar instruments, once the blood culture bottle has been tested positive for microorganism presence, it is difficult to obtain a high level of characterization of the microbial agent, or identification of the species of the microbial agent, due to the interference of blood components and artifacts of the disposable system (e.g., bottle) containing the sample. Therefore, current methods use a bottle or other suitable disposable container and a related instrument for natural growth and detection of a microorganism in the sample, as described above. Once the instrument indicates that the bottle is positive for presence of a microbial agent, according to current methods the "positive" bottle is manually retrieved from the instrument and a portion of the sample is manually removed from the bottle and cultured on an agar plate. There are instruments in the art that automate the streaking of a sample medium on a culture plate and incubating the plate. One such instrument is described in U.S. Pat. No. 6,617,146. After streaking, the plate is manually placed in an incubator and periodically inspected for growth of a subculture of the microorganism. After the subculture has grown sufficiently, a sample of the culture is taken from the plate and placed in a test tube. The test tube is then introduced into yet another instrument for identification testing via a disposable test sample card having a multitude of individual wells. The disposable test cards are known in the patent literature, see e.g., U.S. Pat. Nos. 4,118,280, 3,963,355, 4,018,65; 4,116,775 and 4,038,151, 5,609,828, 5,746,980, 5,766,553, 5,843,380, 5,869,005, 5,916,812, 5,932,177, 5,951,952, and 6,045,758, the entire content of which is incorporated by reference herein.

The test sample card is then processed in an analytical instrument known in the art as the VITEK 2 instrument of the assignee. The VITEK 2 instrument incubates and periodically reads the wells of the test sample card with a reader unit. Growth of the sample in one or more of the wells of the cards results in identification of the microbial agent. The VITEK 2 instrument is described in the patent literature, see e.g., U.S. Pat. Nos. 5,762,873 and 6,086,824, the content of which is incorporated by reference herein.

This entire process from the time of introducing the sample into the blood collection bottle to culture, detection of microorganism presence, and then identification of the microorganism by the VITEK 2 instrument typically takes 2-5 days. The identification steps alone, occurring after positive bottle detection, typically occupy 1-3 of these days.

Substantial, and potentially life saving, clinical benefits for a patient are possible if the time it takes for detection and identification of a microbial agent in a blood sample and reporting the results to a clinician could be reduced from the current 2-5 days to less than one day. A system that meets this need has heretofore eluded the art. However, such rapid identification and/or characterization of a microbial agent in a biological sample such as a blood sample is made possible by this invention.

The methods and apparatus of this disclosure are useful in their own right; however they are particularly useful when implemented in an instrument for rapidly identifying and/or characterizing a microbial agent as described in our prior provisional application, in co-pending application Ser. No. 12/800,467, filed on the same date as this application, and in embodiments disclosed herein.

SUMMARY

In one aspect, an apparatus for automated venting of a specimen container having a closure sealing the interior of the specimen container from the environment is provided. The apparatus includes a rack holding the specimen container; a venting device having a needle, a chamber in fluid communication with the needle and a port in fluid communication with the chamber; a robotic transfer mechanism moveable relative to the rack; and a sample removal apparatus attached to the robotic transfer mechanism having gripping features for gripping the venting device. The sample removal apparatus and robotic transfer mechanism are moveable relative to the specimen container so as to automatically insert the needle of the venting device through the closure of the specimen container to thereby vent the interior of the specimen container and obtain equilibrium between the interior of the specimen container and the atmosphere.

In another aspect, an automated method is disclosed for venting a specimen container in the form of a bottle having a closure sealing the interior of the specimen container from the environment, comprising the steps of: holding the bottle in a rack; automatically and with the aid of robotic apparatus grasping a venting device having a needle, a chamber connected to the needle and a port connected to the chamber; automatically moving the robotic apparatus so as to place the venting device in a position proximate to the bottle in the rack; automatically inserting the needle of the venting device through the closure so as to place the needle into the interior of the bottle, and bringing the interior of the specimen container to equilibrium with the atmosphere via the needle, chamber and port.

In another aspect, an apparatus for automated sampling of a specimen container having a closure sealing the interior of the specimen container from the environment is disclosed. The apparatus includes a rack holding the specimen container; a sampling device having a needle, a chamber in fluid communication with the needle and a port in fluid communication with the chamber; a robotic transfer mechanism moveable relative to the rack; a sample removal apparatus attached to the robotic transfer mechanism having gripping features for gripping the sampling device; and a pneumatic system coupled to the port of the sampling device. The sample removal apparatus and robotic transfer mechanism are moveable so as to automatically insert the needle of the sampling device through the closure of the specimen container, the pneumatic system operative to draw a portion of a sample contained within the specimen container into the chamber of the sampling device via the needle.

In still another aspect, an automated method for sampling a specimen container in the form of a bottle having a closure sealing the interior of the specimen container from the environment is disclosed. The method includes the step of (a) holding the bottle in a rack; (b) automatically and with the aid of robotic apparatus grasping a sampling device having a needle, a chamber connected to the needle and a port connected to the chamber; (c) automatically moving the robotic apparatus so as to place the sampling device in a position proximate to the bottle in the rack; (d) automatically inserting the needle of the sampling device through the closure so as to place the needle into the interior of the bottle, and (e) applying vacuum to the port of the sampling device so as to draw a portion of a sample contained in the bottle into the sampling device.

BRIEF DESCRIPTION OF THE DRAWINGS

The following detailed description makes reference to the appended drawing figures. It is intended that the embodiments and figures disclosed herein are to be considered illustrative and offered by way of example rather than restrictive. In particular, the inventive venting and sampling apparatus of this disclosure will be described in conjunction with several embodiments of an automated instrument for rapid identification and/or characterization of a microbial agent within a specimen container. This environment for use of the apparatus of this disclosure is offered by way of example and not limitation.

FIG. 21 is sequence of perspective views of the sample removal apparatus showing the operations of transferring the separation device to the separation and concentration station and optical interrogation of the separation device in the identification and/or characterization module.

FIG. 22 is a more detailed illustration of the separation and concentration station and the identification and/or characterization module.

FIGS. 26A-26C are a flow chart showing the steps performed in the operation of both automatically detecting the presence of a microbial agent in a specimen container (FIG. 26A) and automatically identifying and/or characterizing the microbial agent (FIGS. 26B and 26C).

FIG. 28 shows one embodiment in which the automated detection and identification instruments can be combined into a single instrument.

FIG. 29 is another perspective view of the embodiments of FIGS. 27 and 28. A multiple axis robot is used access the specimen containers and perform the sampling operation using disposable sampling devices.

FIG. 30 is a perspective view of cassettes holding disposable sampling devices and disposable separation devices, which can be used in the instruments of either FIG. 2-5 or 27-29.

FIGS. 43A, 43B and 43C are cross-sectional, side and perspective views, respectively, of the sampling device and the separation device prior to introduction of the sample from the sampling device into the separation device. FIG. 43D is another perspective view of the sampling and separation device, with the rubber needle sheath of the sampling device shown partially removed in order to show the needle of the sampling device.

FIG. 44 is a perspective view of the sampling device in position to inject a portion of the sample into the separation device.

FIG. 45 is a side view of the injection operation shown in FIG. 44.

FIG. 53 is a top view of the body portion of the separation device embodiment shown in FIG. 51.

FIG. 54 is a cross-sectional view along line A-A of the separation device embodiment shown in FIG. 53.

FIG. 55 is a cross-sectional view along line B-B of the separation device embodiment shown in FIG. 53.

FIG. 57 is a front view of the combined sampling and separation device shown in FIG. 56 with a pinch valve shown in the open position.

FIG. 58 is a cross-sectional view of the combined sampling and separation device shown in FIG. 57 with the pinch valve shown in the open position.

FIG. 59 is a front view of the combined sampling and separation device shown in FIG. 56 with a pinch valve shown in the closed position.

FIG. 60 is a cross-sectional view of the combined sampling and separation device shown in FIG. 58 with the pinch valve shown in the closed position.

FIG. 63 is a cross-sectional view of the valve shown in FIG. 62.

FIG. 64 is a side view of a third embodiment of a combined sampling and separation device which can be used in conjunction with the identification and/or characterization instrument of FIG. 1.

FIG. 65 is a cross-sectional view of the combined sampling and separation device shown in FIG. 64.

FIG. 68A is a side view of the combined sampling and separation device shown in FIG. 67.

FIG. 68B is a cross-sectional view of the combined sampling and separation device shown in FIG. 68A.

FIG. 69A is a side view of the combined sampling and separation device shown in FIG. 67.

FIG. 69B is a cross-sectional view of the combined sampling and separation device shown in FIG. 69A.

DETAILED DESCRIPTION

I. Overview

An automated instrument is described herein that provides a new architecture and method for automated identification and/or characterization of a microbial agent in a specimen sample, e.g., biological sample. The identification and/or characterization instrument 104 is shown in block diagram form in FIG. 1. Two embodiments are described herein in great detail, a first embodiment described in conjunction with FIGS. 2-26 and a second embodiment described in conjunction with FIGS. 27-46. The embodiments of the instrument 104 operate on a specimen container 500 (FIG. 1) containing a sample. In one example, the specimen container 500 is a standard culture bottle, e.g., a blood culture bottle, for containing a specimen sample therein, e.g., a blood sample.

The venting and sampling aspects of this invention are included as features of the instrument 104 as will be apparent from the following discussion.

In general, any type of sample that may contain a microbial agent, e.g., bacterium, fungi or yeast species, can be tested in the instrument 104 such as for example biological samples. For example, the specimen sample can be a clinical or non-clinical sample suspected of containing one or more microbial agents. Clinical samples, such as a bodily fluid, include, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. Non-clinical samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like.

One possible configuration for the instrument 104 of this disclosure is in a combined system which integrates detection of a microbial agent in a specimen container with automated identification and/or characterization of the microbial agent. Such a combined approach is described in the prior provisional application and in co-pending application Ser. No. 12/800,467, filed on the same date as this application. This combined approach is also described in conjunction with the embodiment of FIG. 27.

Figure 47:
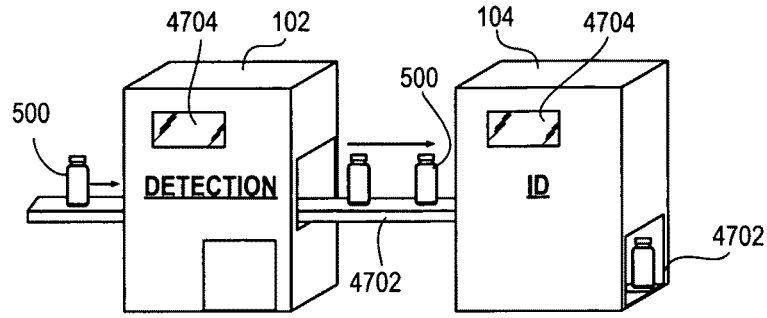
FIG. 47 is a schematic representation of a detection instrument for detection of a microbial agent in a biological sample coupled to an automated identification and/or characterization instrument via a conveyor.

In this configuration, a specimen container 500 (FIG. 1) is inoculated with a specimen sample (e.g., clinical or non-clinical sample) and loaded/unloaded into/out of an automated detection instrument 102 (e.g. FIG. 47). After a sufficient time interval to allow natural amplification of microorganism (this time interval varies from species to species), the specimen container is tested within the detection instrument 102 for the presence of a microorganism. The testing occurs on a periodic basis so that as soon as a specimen container is tested positive it can be transferred to the identification and/or characterization instrument 104 for further analysis of the specimen sample.

Detection can be accomplished using a variety of technologies such as the colorimetric sensor described in the patent literature (see U.S. Pat. Nos. 4,945,060; 5,094,955; 5,162,229; 5,164,796; 5,217,876; 5,795,773; and 5,856,175). Detection could also be accomplished using intrinsic fluorescence of the microorganism, detection of changes in the optical scattering of the media, or detection in the generation of volatile organics in the media or headspace. These techniques are known in the art and described in previously cited patent literature in the Background section of this document.

Once a specimen container 500 is detected as positive in the automated detection instrument 102 (see FIG. 47), the detection instrument 102 will notify the operator through an indicator (e.g., visual prompt), or via a notification at the user interface display, or by other means. The system may be set up to automatically analyze a positive specimen container or require end user acknowledgement prior to sample analysis in the identification/characterization instrument 104 described below. With automatic characterization, it would be possible to notify the physician immediately via electronic means of the results from the identification/characterization system.

Once a specimen container is determined to be positive in the detection instrument 102, the positive specimen container is handed off or transferred to the identification and/or characterization instrument 104 described below. See FIG. 47. The manner in which this is accomplished can vary widely depending on the physical configuration of the detection and identification/characterization instruments 102 and 104. One example of how this can be accomplished is described below in conjunction with FIG. 27.

Figure 1:
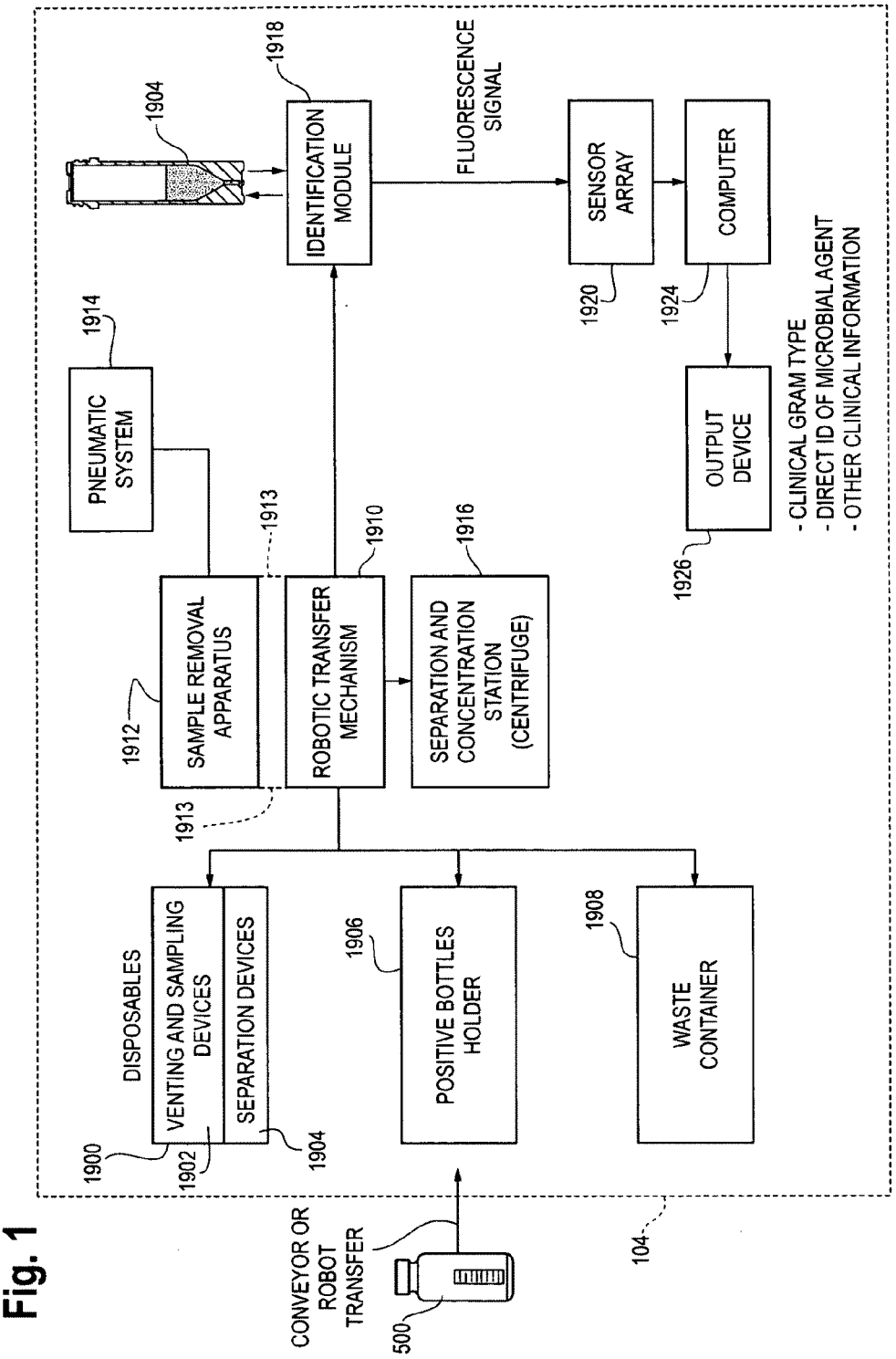
FIG. 1 is a block diagram of an automated instrument for rapid identification and/or characterization of a microbial agent present in a sample. The venting and sampling aspects of this disclosure are implemented in the instrument of FIG. 1; however they could be implemented in other instruments or in identification instruments with different configurations.

Referring now in particular to FIG. 1, a specimen container or bottle 500 is received in the identification and/or characterization instrument 104, either in an automated or manual fashion. The manner in which this occurs is not particularly important and can vary widely depending on the configuration of the instrument 104. The specimen container 500 is placed in a suitable holding structure or rack 1906 in the identification and/or characterization instrument 104. FIGS. 2, 5, 27 and 28 show several possible configuration for the holding structure 1906. The holding structure 1906 is typically adapted for holding a multitude of specimen containers 500. The holding structure 1906 has a facility for rotating the specimen containers to inclined positions above and below horizontal to facilitate venting and sample removal, as described below and optionally agitation of the sample and thereby promoting microbial growth. In an alternative configuration, the positively declared specimen container could remain in the racks within the detection instrument 102 and the sampling could occur directly from the detection instrument.

The identification and/or characterization instrument 104 includes a sample removal apparatus 1912 which holds or grasps a disposable venting and/or sampling device 1902. Together, they operate to vent the specimen container and remove a test sample (i.e., a portion of the specimen sample in the positive specimen container 500) and subsequently add the portion to a separation device 1904 (see FIGS. 6-11). The separation device 1904 can take several forms, and one configuration is described herein in which the separation device includes a reservoir (FIG. 8, item 2602) for receiving the sample and a capillary tube 2604 connected to the reservoir 2602. The identification/characterization instrument 104 further includes a separation and/or concentration station 1916, optionally in the form of a centrifuge, which operates on the separation device 1904 so as to separate the microbial agent from other components in the test sample and concentrate the microbial agent within the separation device 1904. In one example, the microbial agent is concentrated in the form of a pellet or pellet-like mass in the bottom of the capillary tube 2604 of the separation device 1904. The identification/characterization instrument further includes a identification and/or characterization module or read station (FIG. 1, 1918) which interrogates the concentrated microbial agent to identify and/or characterize the microbial agent.

The instrument 104 receives a cassette 1900 of disposables. The disposables are of two types: (1) sampling devices 1902 for venting and removing a test sample from the specimen container 500, and (2) separation devices 1904 which receive a portion of the sample from the container 500 via the venting and/or sampling device 1902 and in which the microbial agent in the test sample is concentrated. In alternative configuration of the instrument the functions of the venting/and or sampling device 1902 and the separation device 1904 are combined into a single disposable device as shown in FIGS. 51-60 in which case the cassette 1900 will only include a multitude of the combined sampling and separation devices.

The instrument 104 further includes a robotic transfer mechanism 1910 which operates to access the disposables 1902 and 1904, positive specimen containers 500 held in the holder or rack 1906, a waste container 1908, the separation and concentration device 1916, and the identification module 1918. The robotic transfer mechanism 1910 may also operate to receive a positive specimen container from a separate detection instrument, and load the positive specimen container into the holding structure or rack 1906. The robotic transfer mechanism 1910 accesses the waste container, separation and concentration station 1916, identification module 1918 and other modules or components in the instrument 104 as necessary to perform the functions described below. The manner of construction of the transfer mechanism 1910 can vary, widely depending on the configuration of the instrument 104.

The sample removal apparatus 1912 is preferably incorporated into, or coupled to, the robotic transfer mechanism 1910 as indicated by the dashed lines 1913. The apparatus 1912 further includes robot gripping and handling mechanisms to grasp one of the venting and sampling devices 1902, the separation device 1904 and/or the specimen container 500. The sample removal apparatus 1912 is connected to a pneumatic system 1914 which enables robotic gripping functions. The pneumatic system 1914 may include a vacuum pump, as described in the second embodiment below. The vacuum pump operates to provide vacuum to the venting and sampling device 1902 to draw a sample from the specimen container 500 and provide positive pressure to the sampling device 1902 to inject the sample from the sampling device 1902 into the separation device 1904. These aspects of the identification instrument 104 will all be described in greater detail below.

In one embodiment, the identification module 1918 includes a light source (e.g., an excitation light source) which illuminates the concentrated microbial agent in the separation device 1904. In response to the illumination, the concentrated microbial agent emits a detectable fluorescence signal, i.e., intrinsic fluorescence, as described below. In addition, the illumination of the concentrated microbial agent by the light source will generate a reflectance signal or Rayleigh scattering signal; this signal is of the same wavelength of the excitation light and provides additional information about the absorption of the microbial agent. The reflectance signal may also provide the basis of normalization of the fluorescence data The configuration of the identification module 1918 includes a means for spatially dispersing the reflectance/fluorescence spectrum, which may take the form of a spectrometer. These fluorescence and reflectance signals (spectrum) are captured by a sensor array 1920 which generates signals supplied to a computer 1924. The computer executes algorithms to process the reflectance/fluorescence signals and responsively identifies and/or characterizes the microbial agent. In one embodiment, a report containing the identification or characterization result is sent to an output device 1926

(e.g., display or associated computer workstation, pager, cell phone or e-mail server). The results can include clinical gram type, direct identification of the microbial agent (e.g., to the genus or species level in a taxonomic hierarchy), or other clinical information regarding the microbial agent in the sample.

First Embodiment (FIGS. 1-26)

Sample Removal Apparatus and Sampling from the Specimen Container (e.g., Blood Culture Bottle 500) (FIGS. 1-5, 15-16, Items 1910 and 1912)

Figure 5:
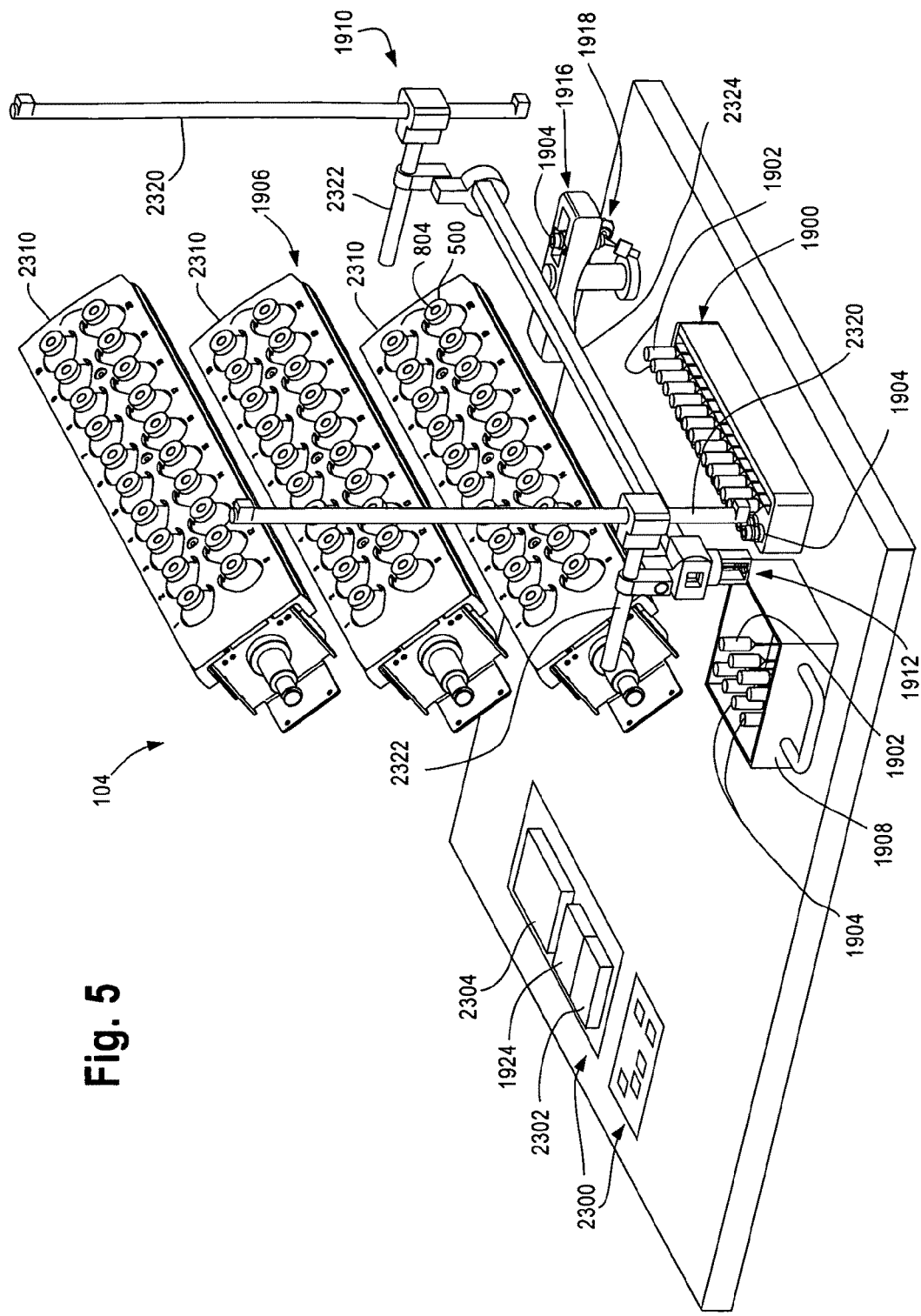
FIG. 5 is another perspective view of the embodiment of FIGS. 2-4.

A sample removal apparatus, in the form of a sample head 1912, retrieves a sampling device 1902 (disposable) from a cassette 1900 of such devices (FIGS. 1, 5). This sampling device 1902 (FIG. 14, see also FIGS. 32, 33) may take the form of a sterile sheathed needle or other means to pierce a stopper or other closure member in the specimen container 500 and vent the specimen container (if necessary) so as to equilibrate the bottle pressure with atmospheric pressure. The sampling device (FIG. 14, 32, 1902) includes a sampling container or chamber 3204 to hold the withdrawn test sample. The test sample will include a portion of the specimen sample and any culture media present. Another possible embodiment is that the sampling device contains the sterile sheathed needle and is directly connected to or incorporated into to the separation device (i.e., a combined sampling and separation device, see FIGS. 60-78). The sample removal apparatus 1912 may optionally include features to decontaminate the surface of the bottle prior to sampling (if necessary).

The robotic transfer mechanism 1910 (FIG. 5) can be moved in three mutually orthogonal translation axes in addition to one rotational axis around one of the orthogonal translation axes so as to be able to position the sample removal apparatus 1912 opposite the access point (e.g. stopper, or septum) of each specimen container/bottle 500 while the bottle is held in the racks 2310 of the specimen container holder 1906. Alignment of a sheathed needle 3202 of the sampling device 1902 to the bottle access point can either be accomplished by a docking feature built-in to the container 500, a vision system (e.g., camera) or using pre-programmed dimensional coordinates and precision motion controlling of the robot transfer mechanism 1910. The bottle 500 is preferably first tilted upward so that the space below the access point or stopper contains the headspace gases and not liquid media. The rationale for this step is that the container should first be vented so that the pressure in the bottle is close to atmospheric pressure. This would prevent venting of aerosols from the bottle and excess fluid transfer and overfill and possible spillage in the case of a bottle over-pressure situation.

Similarly, if the culture has not produced significant by-products (e.g. headspace gases) or the microorganism is not a "gas producer", there will be an under-pressure condition or the pressure inside the bottle will be below atmospheric pressure which would make sampling difficult. The aseptic venting will equilibrate the pressure so that a fluid sample can be removed from the bottle.

After proper venting, the bottle 500 is tilted so that the access port of the bottle is oriented downwards and a liquid sample can be transferred to the sampling device 1902. The sampling device withdraws for example a 0.5 ml, 1.0, or 2.0 ml sample of blood/media from the specimen container. Alternatively, a positive displacement syringe like device could be developed to provide sampling of specimen containers over a wide range of vacuum or pressure conditions.

Figure 14:
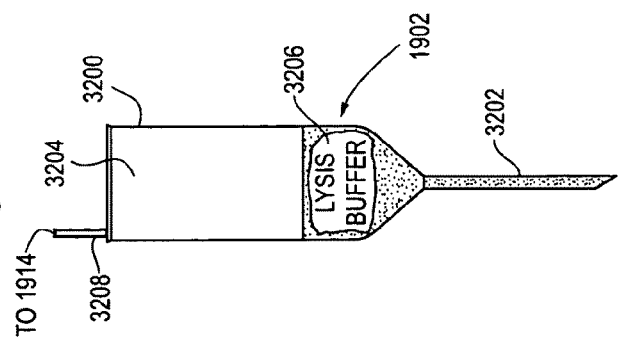
FIG. 14 is an illustration of one embodiment of a disposable sampling device which is used within the identification and/or characterization instrument.
Figure 32:
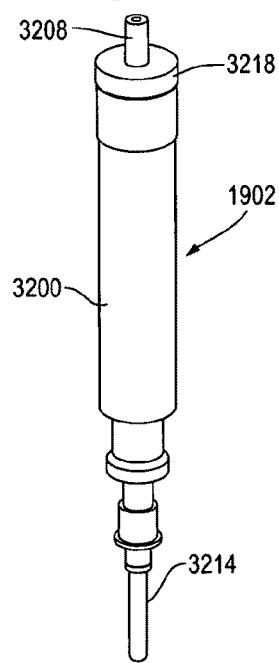
FIG. 32 is a perspective view of an alternative embodiment of a disposable sampling device, presenting a variation on the general design shown in FIG. 14.

The functions of venting and sampling could be performed by separate disposable devices 1902, each having the configuration of FIGS. 14 and 32. Alternatively, the functions of venting and sampling could be performed by a device that includes the separation and concentration function, see FIGS. 51-60 and the discussion below.

Optional Lysis of Components in the Test Sample

After the test sample has been withdrawn from the specimen container 500, any cellular components contained therein (e.g., blood cells) may need to be lysed so that they do not interfere with separation and identification/characterization processes described below. The optional lysis step can be performed using a lysis buffer (which is a pH balanced surfactant solution) or can be accomplished using sonication. Both approaches cause disruption of the blood cell walls. The lysis operation can be performed by adding the lysis buffer to the disposable sampling device 1902 either off-line or within the identification and/or characterization instrument 104. Alternatively, the lysis buffer can be mixed with the blood/media sample during the loading of the sample into the separation device 1904. After the lysis buffer and blood/media sample are combined, some amount of agitation or mixing needs to be performed to ensure the lysis buffer contacts the blood cells and cell wall rupture occurs. In one possible embodiment, the robotic transfer mechanism may move up and down or otherwise to accomplish this mixing. In another embodiment, a mixing station (e.g., a vortexer as described in the second embodiment below) can be included in the instrument 104 for accomplishing this mixing.

As an alternative, the separation device 1904 could have two compartments separated by a thermoresponsive gel or other separation material that would allow the lysis buffer and the blood/media mixture to be combined, then pass through into the microorganism separation device.

Another approach could incorporate a filter to collect the microorganisms on a surface and then resuspend the microorganisms into an inoculum for testing.

It is envisioned the multiple separation devices 1904 could be provided in a format such as a cartridge, cassette, disk or strip to facilitate ease of user loading the system.

Separation and/or Concentration Station (FIGS. 1, 21, Item 1916) and Separation Device (FIG. 1, 6-11, 21, Item 1904)

After withdrawal of the specimen from the specimen container, and after optional lysing of the cellular components (e.g., blood cells) in the sampling device 1902, the sample is then injected or otherwise introduced into one of the separation devices 1904. A microbial agent present in the sample is separated from other components and concentrated into a pellet or pellet-like mass within the separation device 1904.

The details of the separation and/or concentration of the microorganism in the separation device (1904) are described in related patent applications incorporated by reference into this application hereinabove, but the basic method will be described below. The separation is accomplished using a density solution or density cushion filtration. In one embodiment, the separation device 1904 is preloaded with the density cushion. Separation and concentration occurs by means of centrifugation of the separation device 1904.

The separation device 1904 (FIGS. 6-11) itself can take the form of a capillary tube design with a 1-2 mm diameter internal cross section capillary tube filled with the density solution. Above this capillary tube region is a fluted structure that opens up (i.e., opens to a larger cross sectional area) to provide a reservoir for the blood/media sample and the density solution. The bottom surface of the separation device is made of a material that has very good ultraviolet and visible light transmission. The top of the structure has a lid that is applied before centrifugation. In alternative configurations the separation device could be illuminated from the side in which case the lower portion of the separation device is made from a material that has very good ultraviolet and visible light transmission; the cross-sectional shape of the capillary tube may be circular or square.

The mixed or lysed sample contents (lysis buffer and test sample) are loaded into the separation device 1904 (see FIGS. 20A-C and the description below) by means of injecting the sample from the sampling device 1902 into the separation device 1904. The density solution is either loaded into the separation device 1904 on-line in the identification and/or characterization instrument 104 or, more preferably the separation device 1904 is shipped pre-filled with the density solution. After the mixed or lysed sample is loaded into the separation device 1904 and the device 1904 capped, the separation device 1904 is loaded into a centrifuge 1916. Alternatively, this lid is configured with a septum. The sample can be added to the device 1904 by piercing the septum, preventing the need for lid removal and replacement. The centrifuge is activated and spun, e.g. for several minutes at high rpm. This action causes the microbial agent (which is not lysed) to pass through the density solution and concentrate at the base of the capillary tube in the separation device 1904 into a pellet or pellet-like mass in the very bottom of the tube (see FIG. 10, concentrated microbial agent pellet 2804). In one embodiment, the device 1904 loaded with density cushion is centrifuged prior to loading of the test sample to remove any air bubbles or the like that may otherwise interfere with the separation and/or concentration step.

Again, a combined sampling and separation device could be used for both removing a test sample from the specimen container and concentration of the microbial agent; see FIGS. 51-60 and the discussion below.

Identification/Characterization Module (Read Station) for Microbiological Identification and/or Characterization (FIG. 1, 21, 22 Item 1918)

Figure 10:
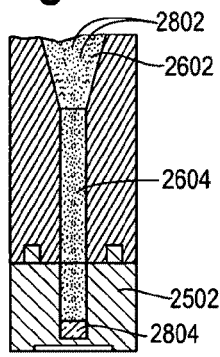
FIG. 10 is a cross-sectional view of the separation device of FIG. 6, showing the concentrated microbial agent in the capillary tube of the separation device after centrifugation.

After the separation device 1904 has been centrifuged as described above, the centrifuge 1916 can be rotated so that the separation device 1904 is in a reading position wherein a identification and/or characterization module (read station) 1918 can interrogate the separated and/or concentrated microbial agent (FIG. 10, pellet 2804). Alternatively, the separation device 1904 can be removed from the centrifuge by the robotic transfer mechanism 1910 and placed in a read station in a separate location.

In one form, the read station 1918 includes an optical reader assembly for interrogating the concentrated microbial agent (pellet) within the separation device 1904. Since the microorganism/microbial agent in the blood/media sample is forced to the bottom surface of the capillary tube in the separation device 1904 (see FIGS. 10 and 11), the microbial agent will be in contact with the bottom surface. In one possible implementation, the optical reader assembly observes the fluorescence signal (e.g., intrinsic fluorescence signal) emitted from the concentrated microbial agent due to illumination from an excitation lights source.

Figure 11:
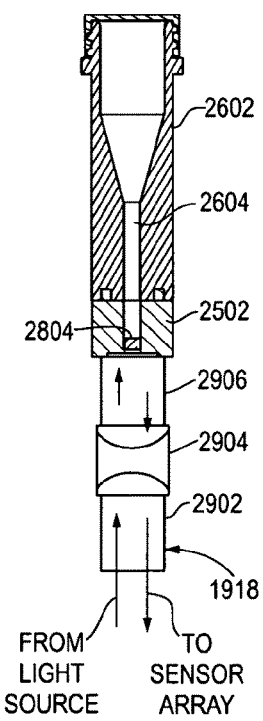
FIG. 11 is a schematic illustration of the concentrated microbial agent in the separation device of FIG. 6 being interrogated by the identification/characterization or reading module.

The fluorescence signal (e.g., intrinsic fluorescence) results from excitation by a UV, visible spectrum or IR light source (see FIG. 11). The light sources could be continuum lamps such as a deuterium or xenon lamp for UV and/or a tungsten halogen lamp for visible/IR excitation. Since these light sources have a broad range of emission, the excitation band can be reduced using optical bandpass filters. Other methods for emission wavelength spectral width that may be utilized include an acousto-optic tunable filter, liquid crystal tunable filter, an array of optical interference filters, prism spectrograph, and still others. Alternatively, lasers are available in discrete wavelengths from the ultraviolet to the near infra-red; additionally many multiplexing methods are known to those skilled in the art, Alternatively, light emitting diodes can be used as narrow-band excitation light sources. LED's are available from a peak wavelength of 240 nm to in excess of 700 nm with a spectral width of 20-40 nm. The same methods for the reduction of spectral width can be incorporated with the LED's to improve discrimination between excitation and emission spectra.

The emission from the sample may be measured by any suitable means of spectral discrimination, most preferably employing a spectrometer. The spectrometer may be a scanning monochromator that detects specific emission wavelengths whereby the output from the monochromator is detected by a photomultiplier tube and/or the spectrometer may be configured as an imaging spectrograph whereby the output is detected by an imaging detector array such as a charge-coupled device (CCD) detector array. In one embodiment, a discriminator allows the observation of the fluorescence and/or scattering signal by a photodetection means (such as a photomultiplier tube, avalanche photodiode, CCD detector array, a complementary metal oxide semiconductor (CMOS) area sensor array and/or electron multiplying charge coupled device (EMCCD) detector array (FIG. 1, item 1920). An optical lens system (2904 in FIG. 11) in front of the sensor array will magnify the 0.78-2.0 $mm^2$ area forming the bottom of the capillary tube 2604 so that it fills the frame of the sensor array. Alternatively, coupling between the disposable separation device 1902 and the optical fiber is direct optical fiber coupling with no lens system; the optical fiber probe is a six around one configuration at the distal end, with the proximal end having a linear configuration for emission fibers to couple into the entry slit of a spectrometer. Fluorescence signal strength at several different wavelengths are acquired and saved in a computer memory.

An alternative configuration is to reduce the capillary tube 2604 to less than 1 mm in diameter to account for low biomass samples. Furthermore, the geometry of the capillary area may take other shapes, such as a rectangular-shaped internal cross-section. Another optional embodiment is to configure the reading of the capillary tube from the side instead of from the bottom. There are two possible benefits to doing so: (1) avoid debris or fibers that sediment to the base of the capillary tube and (2) provide the opportunity to optically identify the presence of polymicrobic agents. A rectangular shaped capillary tube may be preferred for this side read application.

The identification and/or characterization module 1918 includes a computer (FIG. 1, item 1924) that operates on the fluorescence signal strength measurements which are stored in memory. The measurements are compared to experimentally determined fluorescence spectra measurements for different types of microorganisms (i.e. Gram positive, Gram negative, yeast, etc.) that are also stored in memory. The computer executes a classification algorithm and generates a classification result for the microbial agent, e.g., gram classification, gram family, and species. In one configuration, further analysis of the spectra of the captured intrinsic fluorescence signal is accomplished so that species identification and/or characterization or at least the top three probabilities for species identification is achieved. Details on the methods executed by the computer are not particularly important to the instant invention and therefore a detailed discussion is omitted for the sake of brevity.

Figure 23:
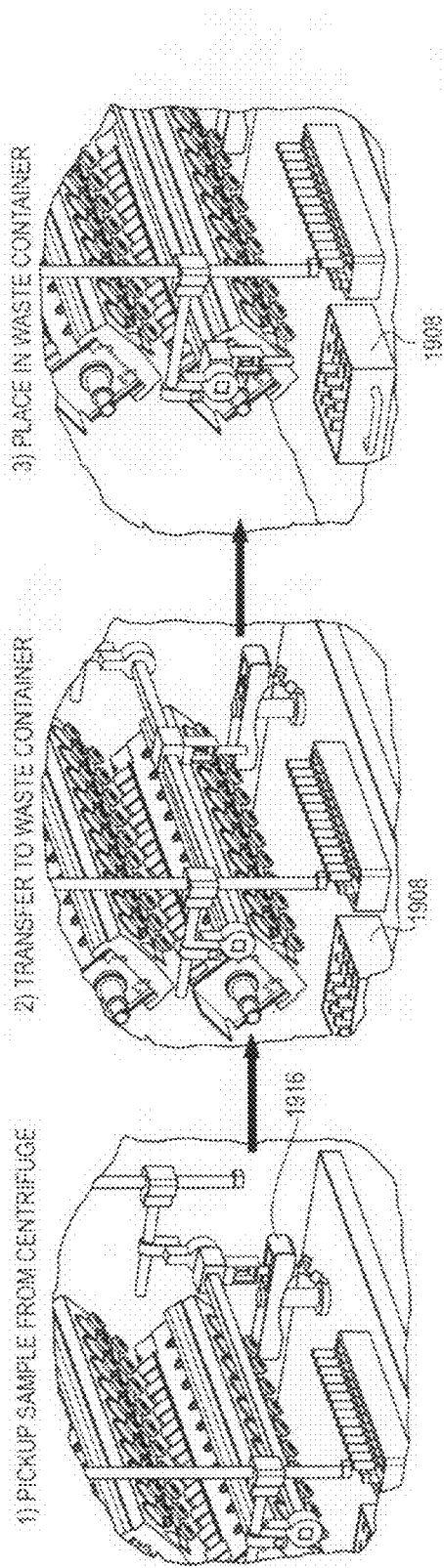
FIG. 23 is a sequence of three perspective views of the identification and/or characterization instrument showing the operations of picking up the separation device, transferring the separation device to the waste container and placing the separation device in the waste container.

Disposal of Sampling Device 1902 and Separation Device 1904 (FIGS. 1, 23, Item 1908)

After the test sample is injected from the sampling device 1902 into the separation device 1904, the sampling device 1902 is discarded into a biowaste container 1908 within the identification and/or characterization instrument 104. After the reading of the separation device 1904, the separation device 1904 is also discarded in the biowaste container 1908. The biowaste container is periodically removed from the identification/characterization instrument and emptied, and then replaced into the identification/characterization instrument.

User Interface

The identification instrument 104 preferably includes a user interface (not shown) which provides an operator with status information regarding specimen containers loaded into the identification instrument. The user interface may include some or all of the following features:

Touch screen display
Keyboard on touch screen.
System status
Positives alert
Communications to other systems (DMS, LIS, BCES & other detection or identification Instruments).
Specimen Container status
Retrieve specimen containers
Visual and audible Positive Indicator
USB access (back ups and external system access).
Remote Notification of Identification and/or Characterization Results, System Status and Error Messages The particular appearance or layout of the user interface is not particularly important.

The identification results are sent to an output device 1926 (FIG. 1), which may be a computer memory, instrument display, printer, pager, cell phone, personal digital assistant, e-mail server, or other device. The results will typically include one or more of the following: clinical gram type of the microbial agent, identification and/or characterization of the species of the microbial agent, or other clinical information.

Specimen Container 500

The specimen container 500 shown in FIG. 1 is designed to hold and contain a sample and may take the form of a standard culture bottle, e.g., blood culture bottle. Preferred embodiments of the bottle incorporate a bar code (FIG. 1) for automated reading of the bottle 500 within the identification/characterization instrument 104 or off-line equipment. The bottle 500 includes a stopper (not shown) sealing the container from the environment having a pierceable septum. Optionally, where the bottle is used for both detection and automated identification, the bottle includes a colorimetric sensor formed or placed in the bottom of the bottle for purposes of colorimetric detection of the presence of microbial growth in the bottle 500. Specimen containers of the type shown in FIG. 1 are well known in the art and described in the patent literature cited in the Background section of this document, therefore a further description is unnecessary.

The configuration of the bottle is not particular important and the inventive system and methods can be adapted to a variety of containers for containing a sample. Thus, the present description of blood culture specimen containers is offered by way of example and not limitation.

II. Detailed Description of First Embodiment (FIGS. 1-26)

Figure 2:
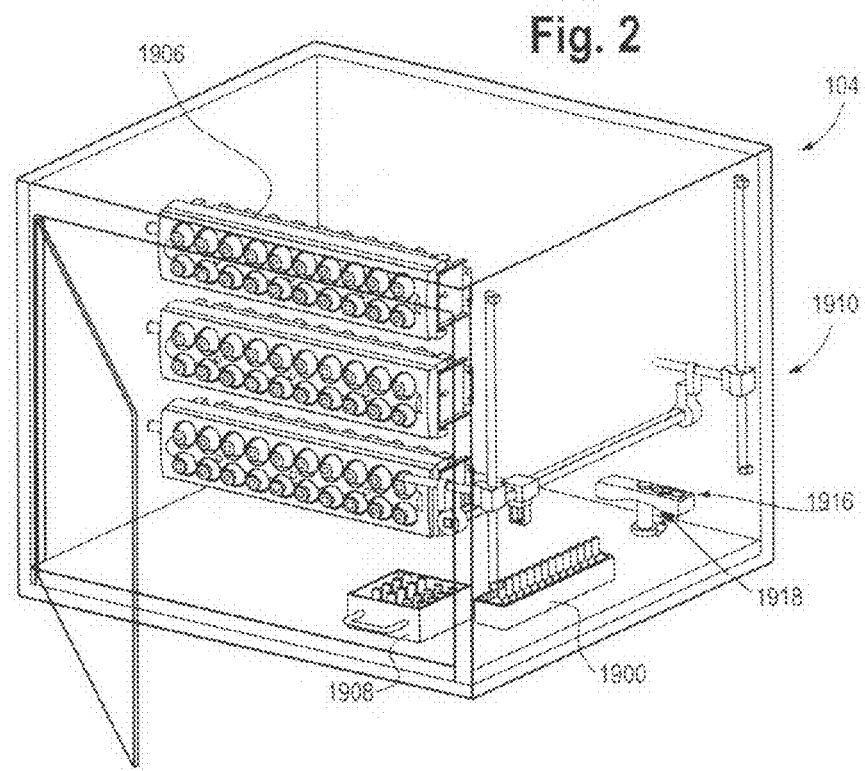
FIG. 2 is a perspective view of one possible configuration of the instrument shown in FIG. 1. The instrument includes a rack for holding specimen containers, a cassette of disposables (including sampling devices and separation devices), a robotic transfer mechanism, sample removal apparatus; a separation and concentration device in the form of a centrifuge, and a identification and/or characterization module (read station) operating to interrogate a separation device containing a concentrated microbial agent for identification and/or characterization of the microbial agent. In one possible embodiment, the instrument of FIG. 2 could be integrated with an automated detection instrument (See FIG. 28, 47-48 below), in which case the rack for the specimen containers is the same structure holding the specimen containers during the detection operations. Alternatively, the identification and/or characterization instrument is located remotely from but coupled to an automated detection instrument as shown in FIG. 47 and described in our prior provisional application and co-pending U.S. application Ser. No. 12/800,467, filed on the same date as this application.
Figure 3:
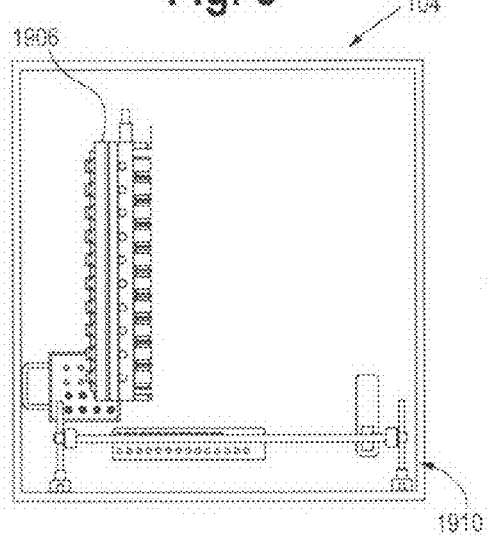
FIG. 3 is top plan view of the identification and/or characterization instrument of FIG. 2, showing the rack of positive specimen containers in one position for incubation.
Figure 4:
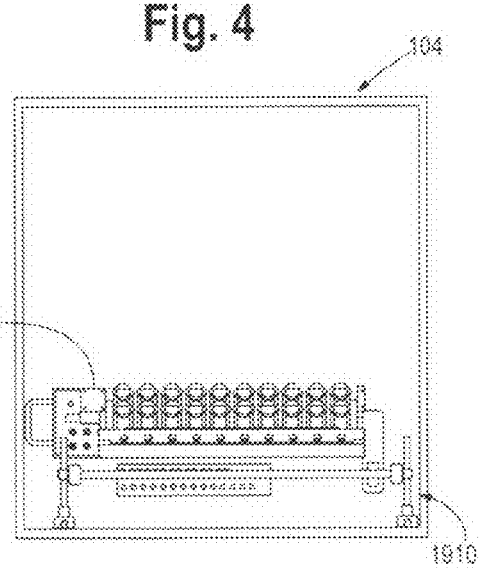
FIG. 4 is a top plan view of the instrument of FIG. 2, showing the rack for the positive specimen containers moved to a position for withdrawal of the sample from the bottle for identification and/or characterization testing.

FIG. 2 shows one possible configuration of the identification/characterization instrument 104, including the cassette of disposables 1900, a rack or holder 1906 for positive specimen containers, a waste container 1908, a robotic transfer mechanism 1910, a sample removal apparatus 1912 which is attached to or coupled to the robotic transfer mechanism 1910, a separation and concentration station 1916, and the identification and/or characterization module 1918. FIG. 3 is a top plan view of the arrangement of FIG. 2. The holder 1906 includes three racks that are oriented in one position for incubation and receiving new positive specimen containers, e.g., from a remote detection instrument or a manual loading door. In FIG. 4, the racks are moved to a position for sample removal from the specimen containers, and loading of the sample into the separation device 1904.

FIG. 5 is a perspective view of the identification/characterization instrument in the position of FIG. 4, showing the identification/characterization instrument 104 in further detail. The holder 1906 includes three separate racks 2310, each holding twenty specimen containers 500. The racks 2310 are rotatable as a unit about the horizontal axis to tilt the specimen containers into upward orientation (shown in FIG. 5) for purposes of venting the specimen containers and to a downward orientation (see FIG. 15) for sample removal.

The robotic transfer mechanism 1910 includes vertical guide rails 2320 and a horizontal guide rail 2324. The sample removal apparatus 1912 is moved from left to right and up and down by means of collars connected to the guide rails and a motor and belt driving subassembly (not shown, but conventional). Thus, the sample removal apparatus 1912 can move to any of the bottle positions in the three racks 2310, when the specimen containers are in either the upward or downward orientation. The sample removal apparatus 1912 can further move fore and aft by sliding along the guides 2322.

FIG. 5 also indicates that the instrument 104 includes electronics 2300, which includes a computer 1924 for processing fluorescence measurements, a memory 2302 storing results of the analysis and a further memory or processing units 2304 for storing program code for operation of the identification/characterization instrument 104. The electronics 2300 are preferably located behind suitable panels, which are not shown.

Cassette of Disposables

FIG. 5 shows a cassette 1900 of disposable devices which is loaded into the identification/characterization instrument 104. The cassette 1900 includes a multitude of sampling devices 1902 and separation devices 1904.

Figure 8:
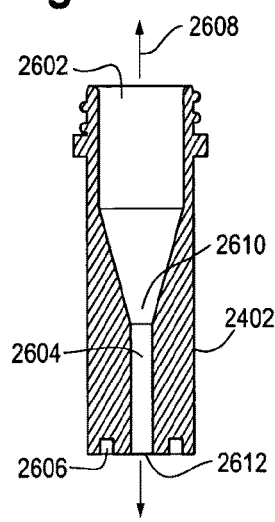
FIG. 8 is a cross-sectional view of the separation device of FIGS. 6 and 7.
Figure 9:
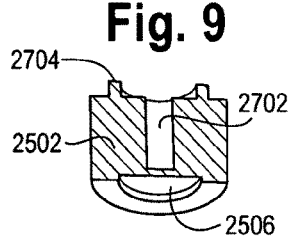
FIG. 9 is a cross-sectional view of an end-cap which is fitted to the lower end of the separation device of FIGS. 6-8.

The separation device 1904 is shown in FIGS. 6-11. Referring to these Figures, the separation device consists of a body 2402 that defines a reservoir 2602 and a capillary tube 2604 which is connected to the reservoir 2602. The body 2402 defines an axis 2608 and the capillary tube 2604 is oriented along the axis 2608. A first end of the capillary tube 2610 is connected to the reservoir 2602 and the second end 2612 of the capillary tube communicates with a tube portion 2702 of an end piece 2502. The reservoir is accessed via a removable cap 2404 that threads onto threads 2502 formed at the top portion of the body 2402. The lower portion of the body 2402 is closed off by an end piece 2502 which is affixed to the body by means of a ridge 2704 fitting into a corresponding recess 2606 in the body and welding or use of an adhesive. The bottom wall 2506 of the end piece 2502 is of reduced thickness as indicated in FIG. 8. The end piece incorporates a capillary tube 2702 which is aligned with the capillary tube 2604 of the body 2402. The body 2402 proximate to the second end of the capillary tube is made from an optically transparent material; in the embodiment of FIG. 7 the end piece 2502 is optically transparent for facilitating optical interrogation of the concentrated microbial agent 2804 located at the bottom of the capillary tube 2604. The separation device 1904 is loaded with a density solution or "cushion" 2802 (FIG. 10), either preloaded with the material or less preferably the material is added to the separation device within the identification/characterization instrument.

Figure 12:
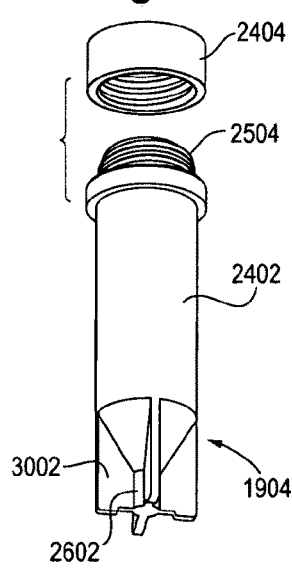
FIG. 12 is a perspective view of an alternative embodiment of the separation device of FIG. 6.
Figure 13:
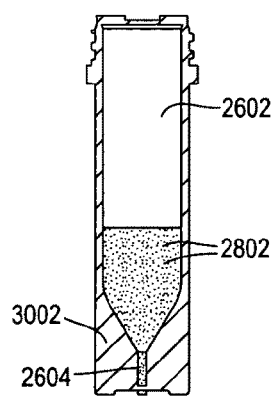
FIG. 13 is a cross-section of the separation device of FIG. 12.

FIGS. 12 and 13 show an embodiment of the separation device 1904 in which the body of the separation device 1904 is a one-piece construction. Walls 3002 provide support for the lower portion of the capillary tube 2602. The body proximate to the lower portion of the capillary tube 2604 is made from an optically transparent material.

FIG. 11 shows the operation of interrogation of concentrated microbial agent 2804 within the separation device 1904, an operation performed by the identification module 1918 of FIGS. 1 and 5. Light from a light source passes along an optical fiber 2902 and is directed by lens system 2904 to the base of the separation device 1904. The light stimulates the production of fluorescence from the microbial agent 2804 and the fluorescence is directed via the optical fiber 2906 through the lens 2904 and fiber 2902 to a CCD sensor array (1920, FIG. 1).

The sampling device 1902 is shown schematically and parts not to scale in FIG. 14. The device 1902 can take the form of a syringe-like device having a body 3200 defining a chamber 3204 and a sheathed needle 3202. The chamber 3204 may be pre-loaded with a selective lysis buffer 3206. The top of the chamber 3204 is sealed. The chamber may have a port 3208 which allows the sampling device to be connected to a vacuum or pneumatic unit to facilitate venting or sampling of a sample from the bottle 500. The lysis buffer 3206 can be pre-loaded into the sampling device 1902, or it may be loaded into the device 1902 in the instrument at the time of use.

The lysis buffer loaded into the sampling device 1902 may be tailored to the specie(s) expected to be found. In one possible configuration, several reservoirs of selective lysis buffers are present in the instrument 104 and one of the lysis buffers is loaded into the sampling device 1902 at the time of use.

Sample Removal Apparatus (Sampling Head) 1912

The sample removal apparatus 1912 of FIGS. 1 and 5 operates to remove a portion of the biological sample in the positive container 500 from the container 500 and add the portion to a separation device 1904 obtained from the supply of separation devices 1900. The physical configuration of the sample removal apparatus 1912 can take a variety of forms, depending on the configuration of the specimen containers, the sampling device, and the separation device. In the illustrated embodiment the sample removal apparatus 1912 takes the form of articulating fingers that open and close so as to grasp the sampling device 1902 and the separation device 1904. The sample removal apparatus 1912 is moved to the required position for sampling and loading into the separation device by means of operation of the robotic transfer mechanism 1910.

Venting and Sampling

Figure 15:
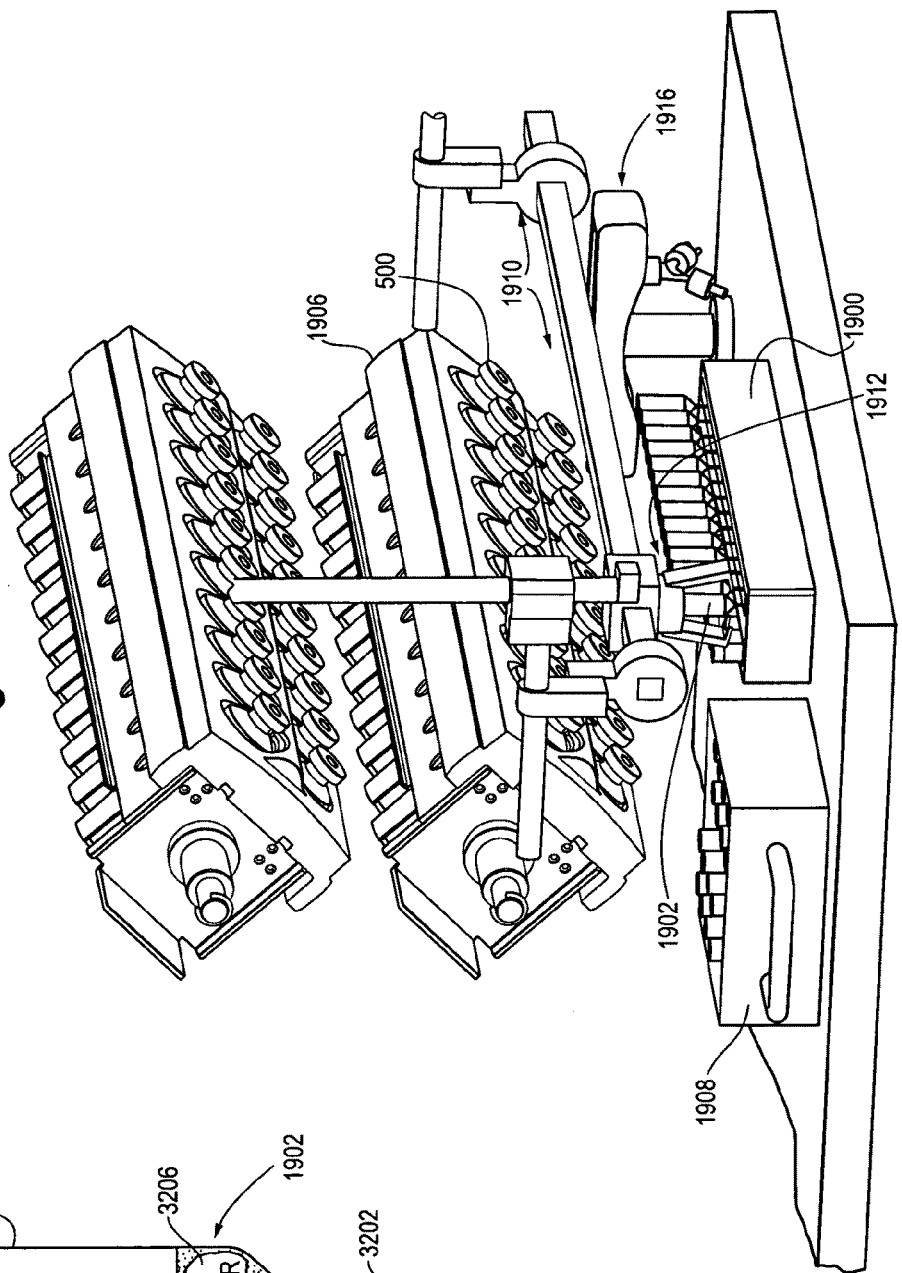
FIG. 15 is a detailed perspective view showing the operation of the sample removal apparatus in the identification and/or characterization instrument to pick up one of the sampling devices of FIG. 14 from a cassette of disposable devices. The cassette includes a multitude of the separation devices of FIG. 6 or 12 and a multitude of the sampling devices of FIG. 14.
Figure 17:
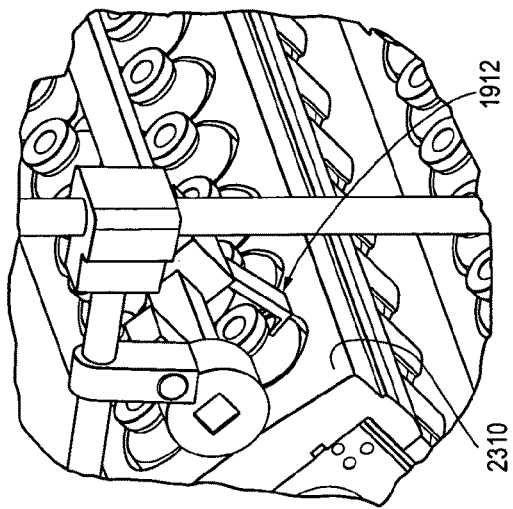
FIG. 17 is a more detailed illustration of the sample removing apparatus in the position shown in FIG. 16.
Figure 16:
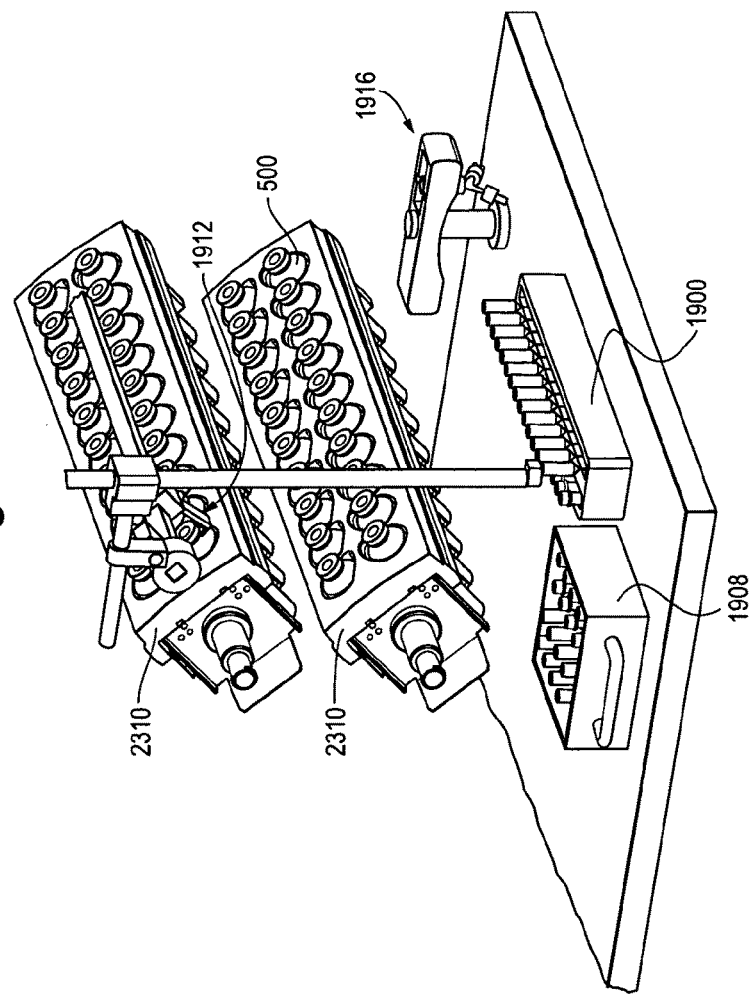
FIG. 16 is a detailed perspective view showing the operation of the sample removal apparatus to sterilize the stopper at the top of the detection container and vent the detection container.

With reference to FIG. 15, the sample removal apparatus 1912 is moved to a position where it is placed directly over one of the sampling devices 1902 in the cassette 1900. The fingers of the sample removal apparatus 1912 grip the sampling device 1902 and the apparatus 1912 is raised upwards, removing the sampling device 1902 from the cassette 1900. As shown in FIG. 16, the specimen containers 500 are tilted upwards. The stopper at the top of the bottle is sterilized using UV light or a disinfecting agent (e.g., bleach or alcohol). As shown in FIG. 17, the bottle is vented by introducing the needle 3202 (FIG. 14) of the sampling device through a pierceable septum in the stopper of the bottle 500, equalizing the pressure within the interior of the bottle to that of ambient conditions. The port 3208 of the sampling device may be connected to the pneumatic system (1914, FIG. 1) during this process, e.g., a rolling diagram pump 1710 as shown in the second embodiment below.

Figure 18:
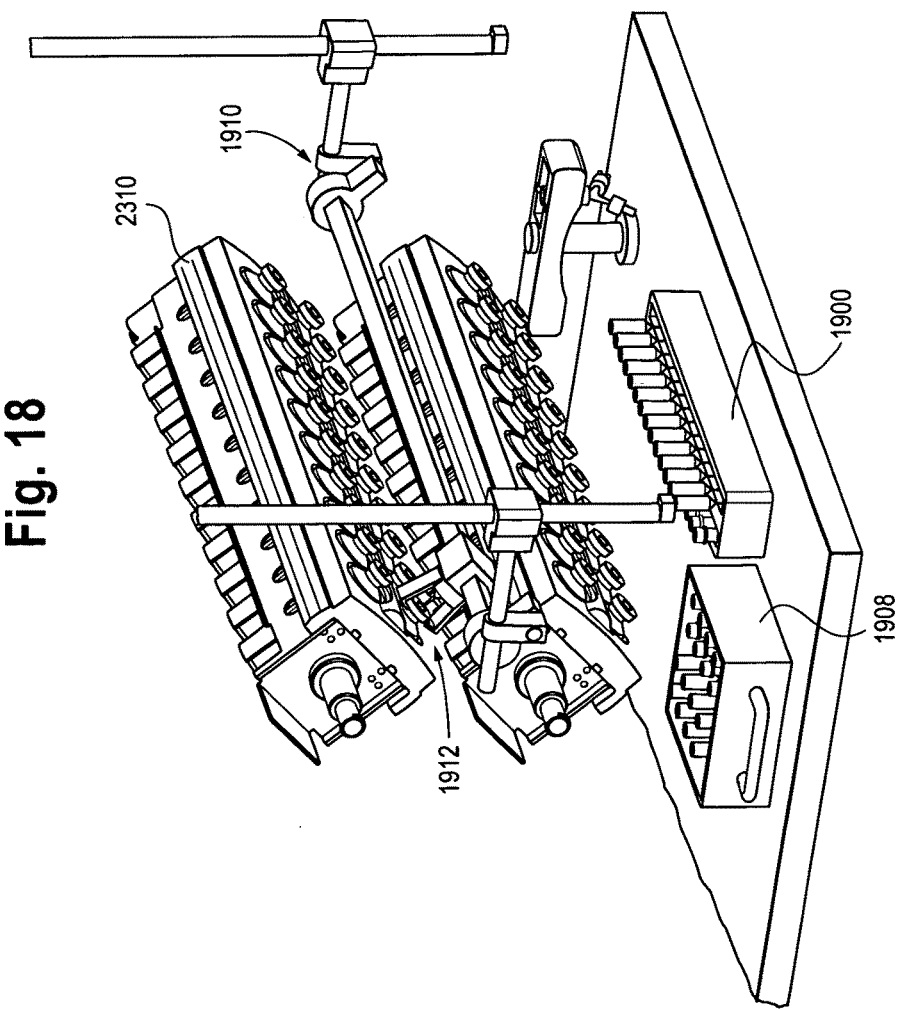
FIG. 18 is a detailed perspective view showing the operation of the sample removal apparatus to withdraw a portion of the sample within the detection container into one of the disposable sampling devices of FIG. 14.
Figure 19:
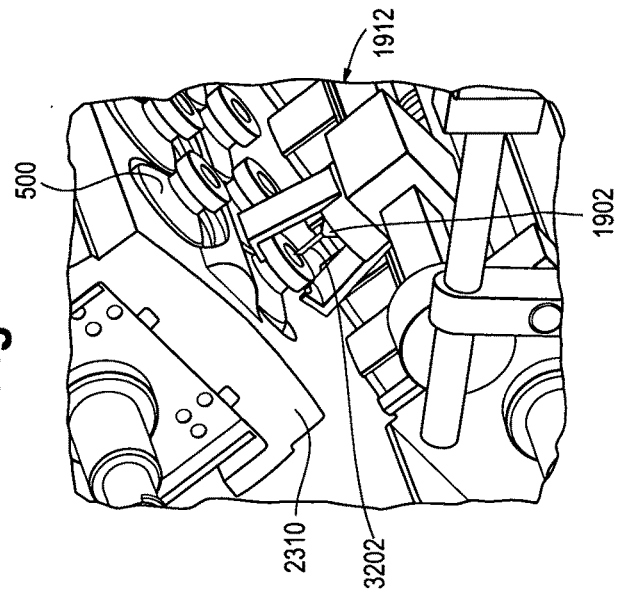
FIG. 19 is a more detailed illustration of the sample removal apparatus in the position of FIG. 18.

As shown in FIGS. 18 and 19, the racks 2310 are then rotated to the downward orientation. The sample removal apparatus 1912, in conjunction the pneumatic system, withdraws a test sample from the bottle 500 into the sampling device 1902.

Lysis

The sampling device 1902 is optionally loaded with approximately 1 ml of a lysis buffer 3206 (FIG. 14). In this embodiment, an approximately 2 ml test sample removed from the bottle 500 and mixed with the lysis buffer in the sampling device 1902, e.g., by agitation of the device 1902 after loading into the sampling device 1902. The lysis operation is selective to non-microorganism component (e.g., the blood cells), i.e., the microbial agent cells are not lysed.

The lysis buffer 3206 selectively lyses undesired cells (i.e., non-microorganism cells) that may be present in the sample, e.g., blood cells and/or tissue cells. The selective lysis of non-microorganism cells permits separation of microorganisms from other components that may be present in the sample. Accordingly, the lysis solution is one that is capable of selectively lysing cells, e.g., non-microorganism cells (e.g., by solubilizing eukaryotic cell membranes). The lysis solution may comprise one or more detergents, one or more enzymes, or a combination of one or more detergents and one or more enzymes.

Useful detergent may include one or more non-denaturing lytic detergent, such as Triton® X-100 Triton® X-100-R, Triton® X-114, NP-40, Genapol® C-100, Genapol® X-100, Igepal® CA 630, Arlasolve™200, Brij® 96/97, CHAPS, octyl β-D-glucopyranoside, saponin, and nonaethylene glycol monododecyl ether (C12E9, polidocenol). Optionally, denaturing lytic detergents can be included, such as sodium dodecyl sulfate, N-laurylsarcosine, sodium deoxycholate, bile salts, hexadecyltrimethylammonium bromide, SB3-10, SB3-12, amidosulfobetaine-14, and C7BzO. Optionally, solubilizers can also be included, such as Brij® 98, Brij® 58, Brij® 35, Tween® 80, Tween® 20, Pluronic® L64, Pluronic® P84, non-detergent sulfobetaines (NDSB 201), amphipols (PMAL-C8), and methyl-β-cyclodextrin. In one embodiment, polyoxyethylene detergent detergents may be preferred. The polyoxyethylene detergent can comprise the structure $C_{12-18}/E_{9-10}$, wherein C12-18 denotes a carbon chain length of from 12 to 18 carbon atoms and E9-10 denotes from 9 to 10 oxyethylene hydrophilic head groups. For example, the polyoxyethylene detergent can be selected from the group consisting of Brij® 97, Brij® 96V, Genapol® C-100, Genapol® X-100, nonaethylene glycol monododecyl ether (polidocanol), or a combination thereof and ethylenediaminetetraacetic acid (EDTA).

The lysis solution may also comprise one or more enzymes. Enzymes that can be used in the lysis solutions include, without limitation, enzymes that digest nucleic acids and other membrane-fouling materials (e.g., proteinase XXIII, DNase, neuraminidase, polysaccharidase, Glucanex®, and Pectinex®).

In another embodiment, one or more additional agents can be used, including for example, reducing agents such as 2-mercaptoethanol (2-Me) or dithiothreitol (DTT), stabilizing agents such as magnesium, pyruvate, and humectants, and/or chelating agents such as ethylenediaminetetraacetic acid (EDTA). The lysis solution can be buffered at any pH that is suitable to lyse the desired cells, and will depend on multiple factors, including without limitation, the type of sample, the cells to be lysed, and the detergent used. In some embodiments, the pH can be in a range from about 2 to about 13, e.g., about 6 to about 13, e.g., about 8 to about 13, e.g., about 10 to about 13. Suitable pH buffers include any buffer capable of maintaining a pH in the desired range, e.g., about 0.05 M to about 1.0 M CAPS.

Dispense into Separation Device 1904 and Separation/Concentration

Figure 20B:
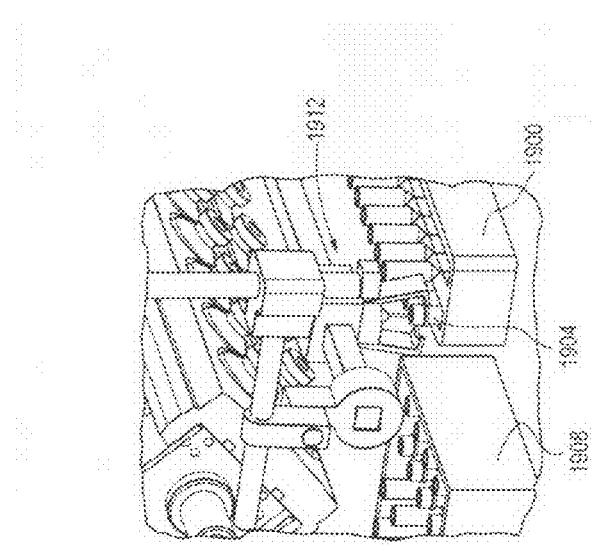
FIGS. 20A-20C are three perspective views of the sample removal apparatus showing the operations of dispensing the sample into one of the separation devices and transfer the sampling device to the waste container.
Figure 20A:
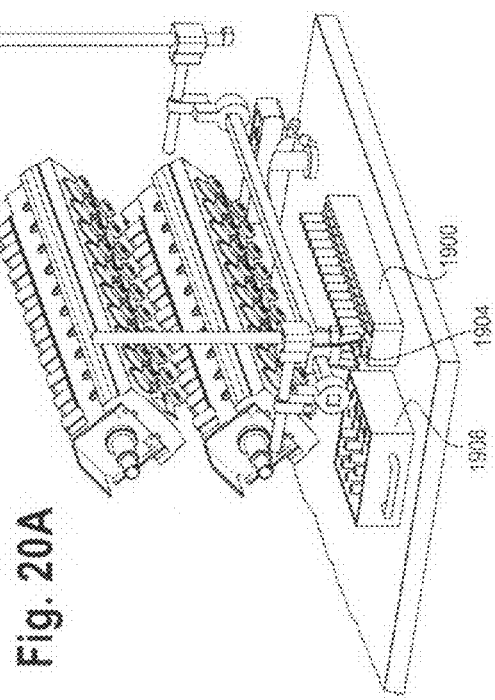
Figure 20C:
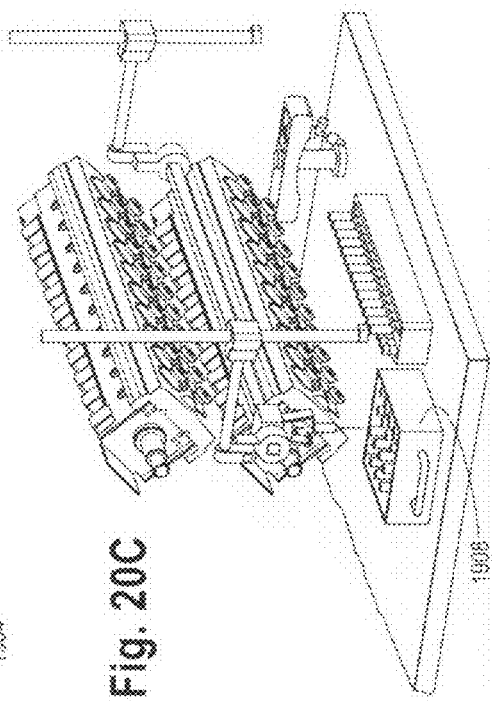

As shown in FIGS. 20A and 20B, the sample removal apparatus 1912 carries the sampling device 1902 (loaded with a mixed lysis buffer and sample solution) to the position of one of the separation devices 1902 in the cassette 1900. The sample removal apparatus pierces the cap of the separation device 1904 with the needle 3202 of the sampling device 1902 and injects 0.5 to 1.0 ml of the sample+lysis buffer mixture into the reservoir of the separation device 1904. The dispensing could also be performed after uncapping the separation device 1904 and recapping the separation device 1904 after recapping. The sample removal apparatus then transfers the sampling device 1902 to the waste container 1908 as shown in FIG. 20C and deposits, it into the waste container.

In one embodiment, the separation is carried out by a centrifugation step in which the sample (e.g., a lysed sample) is placed on top of an approximately 1 ml liquid phase density cushion 2802 (FIG. 10) previously loaded in the separation device 1904 and the device 1904 is centrifuged under conditions (e.g., 10,000 g) which allow the microorganisms to be isolated and concentrated (e.g., the microorganisms form a pellet or pellet-like mass at the bottom and/or sides of the separation device 1904). "Density cushion" refers to a solution having a homogenous density throughout. The density of the cushion is selected such that the microorganisms in the sample pass through the cushion while other components of the sample (e.g., blood culture broth, cell debris) remain on top of the cushion or do not pass all of the way through the density cushion.

The material for the density cushion 2802 can be any material that has the appropriate density range for the methods of this invention. In general, the density of the cushion is in the range of about 1.025 to about 1.120 g/ml. In one embodiment, the material is colloidal silica. The colloidal silica may be uncoated (e.g., Ludox® (W.R. Grace, CT)) or coated, e.g., with silane (e.g., PureSperm® (Nidacon Int'l, Sweden) or Isolate® (Irvine Scientific, Santa Ana, Calif.)) or polyvinylpyrrolidone (e.g., Percoll™, Percoll™ Plus (Sigma-Aldrich, St. Louis, Mo.)). The colloidal silica may be diluted in any suitable medium to form the proper density, e.g., balanced salt solutions, physiological saline, and/or 0.25 M sucrose. Suitable densities can be obtained with colloidal silica at a concentration of about 15% to about 80% v/v, e.g., about 20% to about 65% v/v. Another suitable material for density cushions is an iodinated contrast agent, e.g., iohexol (Omnipaque™ NycoPrep™, or Nycodenz®) and iodixanol (Visipaque™ or OptiPrep™). Suitable densities can be obtained with iohexol or iodixanol at a concentration of about 10% to about 25% w/v. Sucrose can be used as a density cushion at a concentration of about 10% to about 30% w/v e.g., about 15% to about 20% w/v, for blood culture samples. Other suitable materials that can be used to prepare the density cushion include low viscosity, high density oils, such as microscope immersion oil (e.g., Type DF; Cargille Labs, New York), mineral oil (e.g., Drakeol® 5, Draketex 50, Peneteck®; Penreco Co., Pennsylvania), silicone oil (polydimethylsiloxane), fluorosilicone oil, silicone gel, metrizoate-Ficoll® (LymphoPrep™), e.g., at a concentration of about 75% to about 100% for blood culture samples, diatrizoate-dextran (PolymorphoPrep™), e.g., at a concentration of about 25% to about 50% for blood culture samples, carboxymethyl cellulose, hydroxypropylmethyl cellulose, polyethylene oxide (high molecular weight), Pluronic® F127, Pluronic® F68, mixtures of Pluronic® compounds, polyacrylic acid, cross-linked polyvinyl alcohol, cross-linked polyvinyl pyrrolidine, PEG methyl ether methacrylate, pectin, agarose, xanthan, gellan, Phytagel®, sorbitol, Ficoll® (e.g., Ficoll® 400 at a concentration of about 10% to about 15% for blood culture samples), glycerol, dextran (e.g., at a concentration of about 10% to about 15% for blood culture samples), glycogen, cesium chloride (e.g., at a concentration of about 15% to about 25% for blood culture samples), perfluorocarbon fluids (e.g., perfluoro-n-octane), hydrofluorocarbon fluids (e.g., Vertrel XF), and the like as are well known in the art. In one embodiment, the density cushion is selected from one or more of colloidal silica, iodixanol, iohexol, cesium chloride, metrizoate-Ficoll®, diatrizoate-dextran, sucrose, Ficoll® 400, and/or dextran in any combination. The density cushion can also be made up of a combination of materials, e.g., a combination of colloidal silica and oil.

Transfer to Separation and Concentration Station (Centrifuge)

As shown in FIG. 21, after loading of the separation device 1904 with the mixed or lysed test sample, the sample removal apparatus 1912 retrieves the loaded separation device 1904, lifts it out of the cassette 1900, and moves the separation device 1904 to the centrifuge 1916. The separator 1904 is then placed into a holder or loading position of the centrifuge 1916.

A separation and concentration of the microbial agent in the sample occurs within the separation device 1904 using the centrifuge 1916.

The separation step can be carried out to separate the microorganisms from other components of the sample (e.g., non-microorganisms or components thereof) and to concentrate the microorganisms into a pellet that can be interrogated for identification and characterization purposes. The separation does not have to be complete, i.e., it is not required that 100% separation occur. All that is required is that the separation of the microorganisms from other components of the sample be sufficient to permit interrogation of the microorganisms without substantial interference from the other components.

The centrifuge spins the separation device 1904 at high speed in order to concentrate the microbial agent into the bottom of the capillary tube within the separation device 1904. The combination of the action of the lysis buffer on the non-microorganism cells (e.g., blood cells), the presence of the density solution within the separation device 1904, and the centrifugation, results in the separation of microbial agent from the lysed blood/broth mixture and the concentration of the microbial agent into a pellet or pellet-like mass in the bottom of the capillary tube, as shown in FIGS. 10 and 11.

In one embodiment, the separation device 1904 is centrifuged in station 1916 using a swing out rotor so that the microorganisms form a pellet directly on the bottom of the separation device 1904 (in the bottom of the capillary tube shown in FIGS. 8, 10 and 13). The separation device 1904 is centrifuged at a sufficient acceleration and for a sufficient time for the microorganisms to be separated (e.g., a pellet formed) from other components of the sample. The centrifugation acceleration can be about 1,000×g to about 20,000×g, e.g., about 2,500×g to about 15,000×g, e.g., about 7,500×g to about 12,500×g, etc. The centrifugation time can be about 30 seconds to about 30 minutes, e.g., about 1 minute to about 15 minutes, e.g., about 1 minute to about 5 minutes.

Reading

The identification and/or characterization module (read station 1918), which is shown positioned adjacent to the centrifuge then interrogates the concentrated microbial agent using fluorescence spectroscopy (e.g., intrinsic fluorescence and/or diffuse reflectance), Raman spectroscopy or other optical technique. In other embodiments, the microorganisms in the pellet can be interrogated using mass spectrometry techniques, such as MALDI-TOF mass spectrometry, desorption electrospray ionization (DESI) mass spectrometry, GC mass spectrometry, LC mass spectrometry, electrospray ionization (ESI) mass spectrometry and Selected Ion Flow Tube (SIFT) spectrometry. As shown in FIG. 22, the identification and/or characterization module 1918 may be physically located proximate to the centrifuge 1916, in which case the separation device 1904 does not need to be moved further by the robotic transfer mechanism. Alternatively, the identification and/or characterization module 1918 could be located in a different location within the identification/characterization instrument and the robotic transfer mechanism operates to move the separation device to the location of the identification and/or characterization module 1918.

Transfer to Waste

Figure 24:
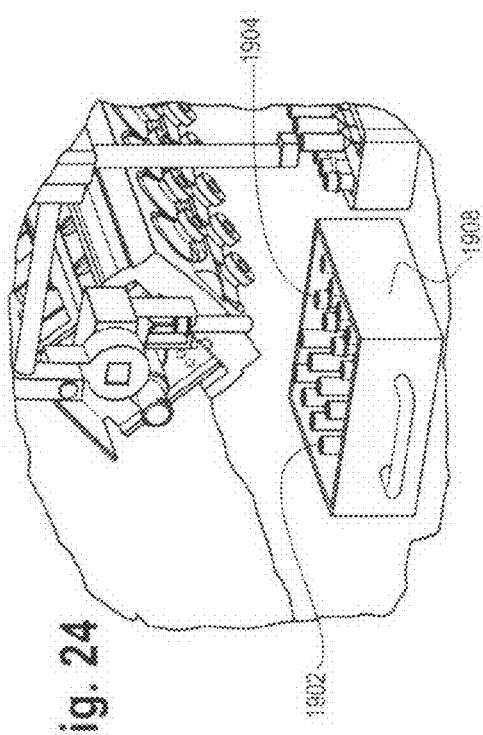
FIG. 24 is a more detailed illustration of the operation of placing the separation device into the waste container.

After reading, as shown in FIG. 23, the robotic transfer mechanism 1910 and sample removal apparatus 1912 operates to lift the separation device 1904 from the centrifuge 1916, transfers the separation device 1904 laterally and places it in the waste container 1908. FIG. 24 shows the waste container 1904 containing a multitude of the sampling devices 1902 and the separation devices 1908. When the waste container 1908 is full it is removed from the instrument and then replaced with an empty waste container. Prior to disposal of the separation device, a photographic image of the lower region of the separation device may be taken with a camera (not shown) to verify the separation process and provide valuable information on the identity of the isolate, such as pellet size, shape, color and density.

External Processing of Concentrated Microbial Agent

While in the above embodiment the concentrated microbial agent is interrogated while it is still located within the separation device 1904, it is possible to remove the concentrated microbial agent from the separation device and test it directly to identify and/or characterize the microbial agent.

Figure 25:
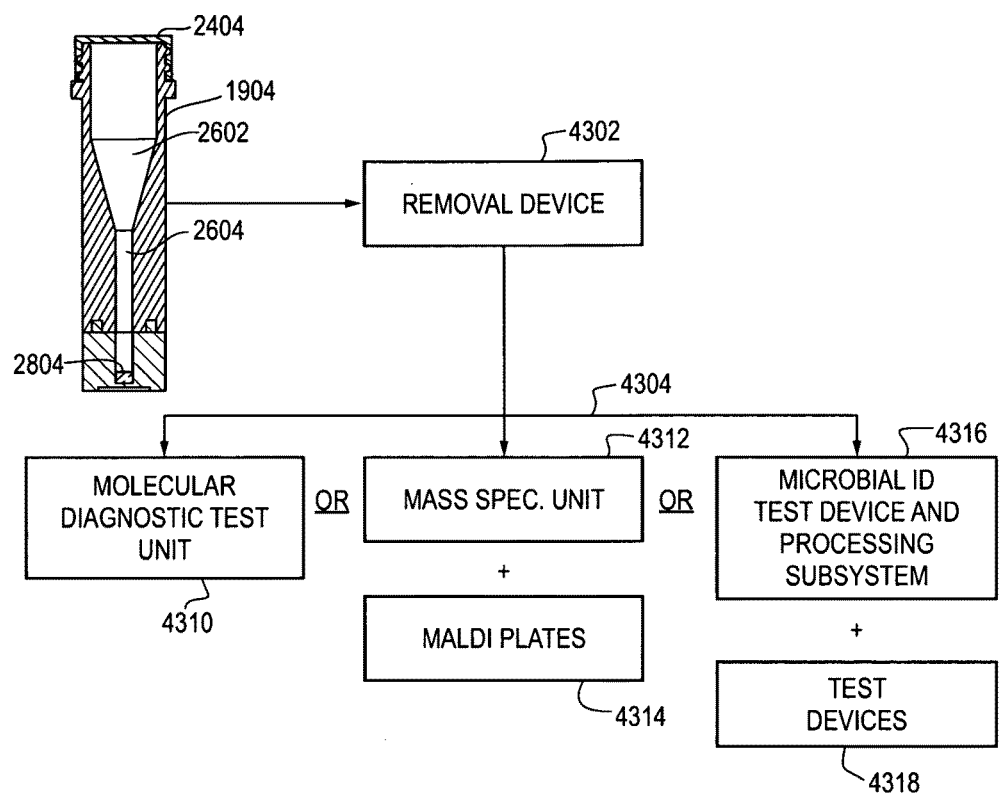
FIG. 25 is a block diagram of an alternative configuration of the identification and/or characterization instrument in which the concentrated microbial agent is removed from the separation device and analyzed after removal. The analysis could be performed by any one of a number of different types of systems or units, including a molecular diagnostic test unit, a mass spectrometry unit, or a microbial identification test device and associated processing instrument.

In this variation, referring to FIG. 25, the separation device 1904 is transferred to a removal device or station 4302. At the station 4302, the cap 2404 of the separation device 1904 is removed and the concentrated microbial agent 2804 is removed from the separation device 1904. The microbial agent is then subject to one or more additional tests. In one possible configuration, the microbial agent is supplied to a molecular diagnostic test unit 4310 which may include a disposable test strip or the like and processing instrument for identification of the agent. Alternatively, a sample of the microbial agent could be applied to a MALDI mass spectrometry plate 4314 and the plate inserted into a mass spectrometry unit 4312. Alternatively, the microbial agent could be delivered to a microbial identification and/or characterization test device 4318 (e.g., test card) and the card incubated and tested in a processing instrument 4316.

III. Method of Operation

Flow Chart (FIGS. 26A, B, C)

Figure 26B:
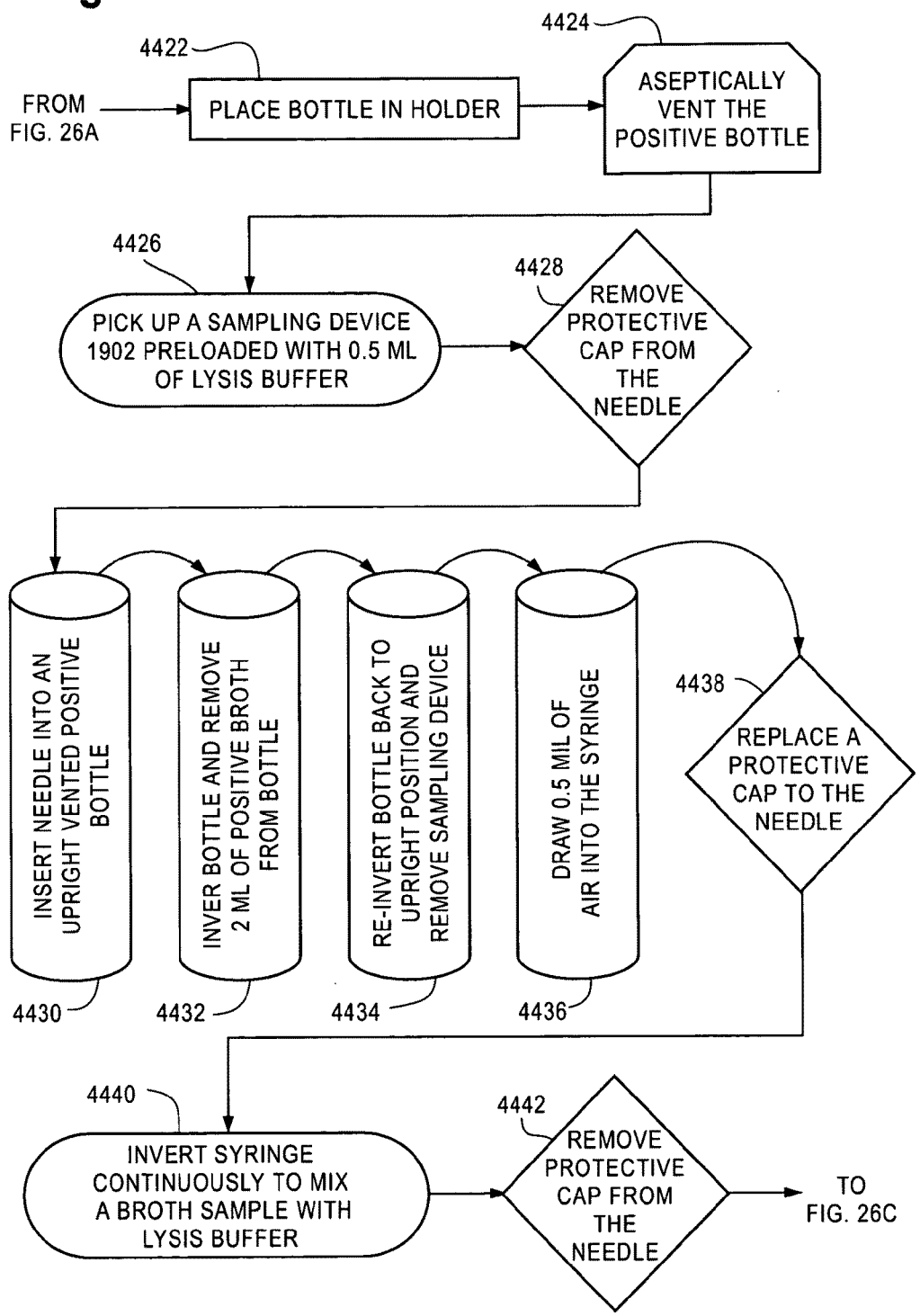

The method of operation of the identification/characterization instrument 104 in an embodiment in which the specimen container 500 is subject to both detection and identification steps will now be described with reference to FIGS. 26A-26C.

The process starts at step 4402 with the loading of a sample into one of the containers 500 and delivery of the loaded container 500 to a detection instrument (as described in our prior provisional application and in co-pending application Ser. No. 12/780,126 filed May 14, 2010 See FIG. 47, instrument 102.

At step 4404, the container 500 is loaded into the detection instrument 102, e.g., by placing the detection container on conveyer which delivers the container to the detection instrument or by manually loading the container. (See FIGS. 47 and 48 and the description of those figures below)

At step 4406, the container 500 is incubated within the detection instrument 102.

At step 4408 the detection container is read (by a detection unit in the instrument 102).

At step 4410, the reading of the detection container is analyzed to determine if the container is positive. If no, the processing branches along NO branch 4411 and a check is made if a timer has expired (step 4412). If the timer has expired, the bottle is deemed negative and the bottle is transferred to the waste container at step 4414. Otherwise, the incubation continues and steps 4406, 4408 and 4410 continue periodically.

If at step 4410 the detection container is positive, the processing proceeds to the YES branch 4416. The detection container is moved to the exit location in the detection instrument at step 4418. At step 4420 the detection container is transferred to the identification/characterization instrument 104, e.g., by moving the detection container 500 onto a conveyor and moving it into the entrance location of the identification/characterization instrument (see FIG. 47). The transfer could occur by some other manner, the details of which can vary widely.

At step 4422 (FIG. 26B), the detection container is placed into one of the racks 2310 of the identification/characterization instrument 104. The robotic transfer mechanism 1910 may be used in this process.

At step 4424, the detection container is aseptically vented. This step may occur prior to picking up of the sampling device or may occur after picking up the sampling device, see FIGS. 15 and 16.

At step 4426, one of the sampling devices 1902 is picked up from the cassette 1900. The sampling device 1902 is preloaded with a selective lysis buffer as shown in FIG. 15; alternatively the lysis buffer is added to the sampling device at this time.

At step 4428, a protective cap (not shown), if fitted, covering the needle 3202 of the sampling device is removed.

At step 4430, the needle 3202 is inserted into a upright vented container 500 (see FIGS. 16 and 17).

At step 4432, the detection container is inverted (see FIGS. 18 and 19) and a small sample (e.g., a 2.0 ml sample) is removed from the container 500.

At step 4434, the container 500 is rotated to an upright orientation and the needle 3202 of the sampling device 1902 is removed.

At step 4436, a small volume (e.g., 0.5 ml sample) of air is introduced into the sampling device. This could be accomplished automatically using the pneumatic system 1914 connected to the sampling device.

At step 4438, a protective cap for the needle 3202, if fitted, is replaced.

At step 4440, the sampling device 1902 is inverted and agitated to thoroughly mix the portion of the sample with the selective lysis buffer.

At step 4442, the protective cap for the needle 3202, if fitted, is again removed. (Note: a station fitted with appropriate gripping or grasping features could be provided for automatically removing and replacing the cap of the needle or alternatively the cap could remain on the needle as described in the second embodiment)

At step 4444, a small portion of the positive broth/lysis buffer mix is discarded into a waste container.

At step 4446, the sample removal apparatus moves the sampling device 1902 to the position above one of the separation devices 1904 (see FIG. 38) and pierces the cap with the needle of the sampling device. The separation device 1904 is pre-loaded with the density cushion in this embodiment.

In one possible variation, the lysis buffer is also loaded into the separation device 1904 with the density cushion and the mixing of the sample and the lysis buffer takes place within the separation device 1904.

At step 4448, the sample removal apparatus 1912 gently adds 0.5 to 1.0 ml of the sample/lysis buffer mixture on top of the density cushion already present in the reservoir of the separation device 1904. See FIGS. 20A and 20B.

At step 4450, the sample removal apparatus 1912 is moved to the position of the waste container 1908 and the sampling device 1902 is discarded. See FIG. 20C.

At step 4452, the sample removal apparatus returns to the separation device 1904 and picks it up out of the cassette 1900 and moves it to the location of the separation and concentration station 1916, and places the separation device 1904 into the centrifuge. See FIG. 21.

At step 4454, the centrifuge cycle is started.

At step 4456, after completion of the centrifugation process, the separation device is moved to the identification and/or characterization module 1918 (reading station). Where the reading station is proximate to the centrifuge, the centrifuge is rotated to a reading position wherein the separation device 1904 is positioned for reading as shown in FIG. 11.

At step 4458, the optical scan of the separation device 1904 in the identification and/or characterization module is started (See FIG. 21, 22).

At step 4460, after completion of the reading operation, the separation device 1904 is placed into the waste container 1908 (see FIGS. 23, 24).

IV. Second Embodiment (FIGS. 27-46)

A second embodiment of the identification instrument 104 will be described in conjunction with FIGS. 27-46. This embodiment is similar to the first embodiment of FIGS. 1-26 in terms of overall function and operation; the main differences are (1) a different construction of the robotic transfer mechanism 1910; (2) a provision for vortexing of the sample and lysis buffer in the sampling device 1902, and (3) inclusion of optional detection features in the rack holding the specimen containers 500 (see FIG. 28) for detecting microbial growth within the container 500 so that the identification system is intimately combined with a detection system for detecting whether a specimen container is positive for presence of a microbial agent. A few other points of differentiation in the details of the configuration of the second embodiment will also be noted in the following description.

However, the second embodiment, like the first embodiment of FIGS. 1-26, shares the same overall goals and design objectives. That is, the second embodiment of FIGS. 27-46 automates the removal of a test sample from a specimen container (preferably soon after a positive determination has been made), automates lysing of non-microorganism cells in the test sample, automates loading of the lysed sample into a disposable separation device, automates separation and concentration of the microbial agent present in the lysed sample in the separation device, and automates interrogation of the microbial agent to identify and/or characterize the microbial agent.

The culture bottles/specimen containers 500 are loaded into racks or holding structures of the identification instrument 104 either manually or automatically. In an optional configuration, the specimen containers 500 are tested for the presence or microorganisms by a detection subsystem which is incorporated into the racks. In a manual, prior art method, without automation, a technician would remove a bottle from a separate detection instrument after the bottle is deemed "positive". This could be several hours after the diagnostic determination, especially if the determination is made in the middle of the night or when the lab is understaffed. However, with the automated identification instrument in this embodiment, the steps of automated identification and/or characterization of the microbial agent can proceed immediately, and automatically, after the specimen container is deemed "positive".

In the case of lytic centrifugation and intrinsic fluorescence measurement, features of both of the illustrated embodiments, it may be desirable that the sample be processed for purposes of identification and/or characterization shortly after a positive call by an associated detection instrument. As the bottle is called positive the microorganisms are in an exponential stage of growth. This growth phase is distinguished from the lag phase and death phase which are both before and after, respectively, the exponential phase. Microorganisms in this exponential phase have different physical and genetic expression characteristics than the lag and death phase.

By automating this process of identification and/or characterization, the technician is removed from the system. Identification and/or characterization of the microbial agent can occur much more rapidly in the present embodiments as compared to prior approaches.

A. System Layout

Figure 27:
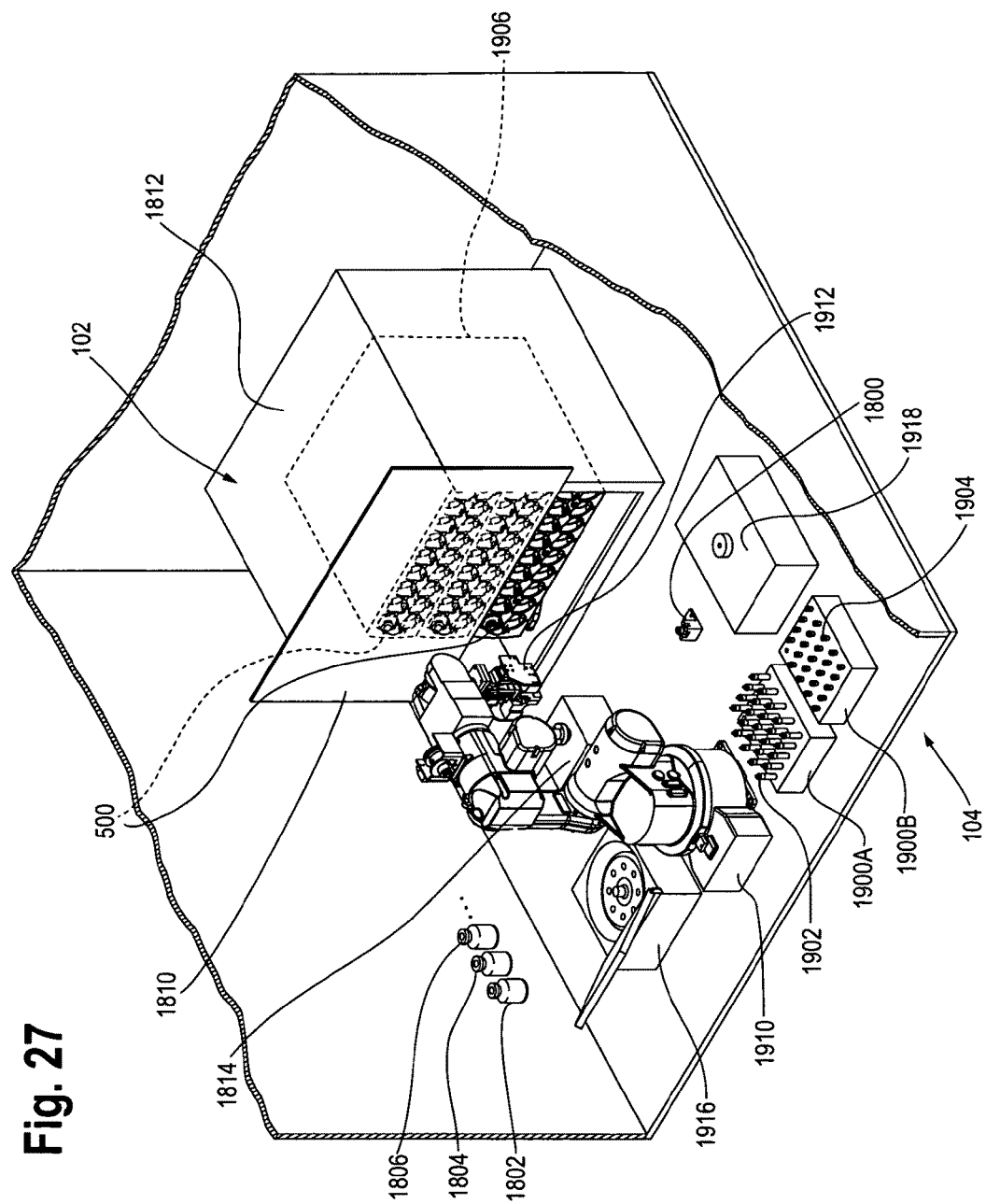
FIG. 27 is a perspective view of a second embodiment of an instrument for rapid and automated identification and/or characterization of a microbial agent in a sample.

The identification instrument 104 in accordance with a second embodiment is shown in FIG. 27. The instrument 104 includes a first cassette 1900A containing a plurality of disposable sampling devices 1902 and a second cassette 1900B containing a plurality of disposable separation devices 1904. A rack or holding structure 1906 includes receptacles for holding a multitude of containers 500 containing samples for identification testing. The rack 1906 is shown contained within an insulated incubation enclosure 1812. The enclosure 1812 includes a door 1810 that is opened to expose the bottles 500 and allow venting of the bottles and removal of a test sample via a robotic transfer mechanism 1910, sample removal apparatus 1912, and the sampling device 1902.

The robot transfer mechanism 1910 includes a rotating base and movable joints and segments between the joints so as to allow the robotic transfer mechanism 1910 and in particular gripping structures included in the sample removal apparatus or sampling head 1912 to access the various components in the instrument 104. These components include a separation and concentration device (centrifuge 1916), the cassettes 1900A and 1900B, a vortexer 1814 for mixing a lysis buffer and test sample within the sampling device 1902, a read station 1918, and various containers 1802, 1804, 1806 containing different lysis buffers and/or density cushions in the situation where the lysis buffers and density cushions are added to the sampling device or separation device at the time of use. The robotic transfer mechanism 1910 is able to access each of the bottles 500 and optionally grip and hold the bottles 500. Thus, the robotic transfer mechanism 1910 may optionally be the device to automatically load the bottles 500 into the holding structure or rack 1906. Alternatively, the bottles 500 could be loaded into the rack manually via an access door positioned on the opposite side of the enclosure 1812 from the door 1810. See FIG. 49, door 4902.

In the configuration of FIG. 27, a centrifuge cup holder 1800 holds a small cup-like holder 1801 into which the separation device 1904 is placed (see FIG. 46A); the combination of the separation device 1904 and cup-like holder 1801 are placed into the centrifuge 1916 for separation and concentration of the microbial agent in the separation device 1904. After centrifugation, the cup-like device 1801 is returned to the cup holder 1800. The sample removal apparatus 1912 grips the separation device and the robotic transfer mechanism places it into the reading/identification module 1918. The concentrated microbial agent in the separation device 1904 is interrogated by the reading/identification module 1918. The reading step may include the features described above, such as measuring intrinsic fluorescence spectra of the sample and, with the aid of a computer, comparison of the measured spectra to a data set containing spectra from known microbial agents and classification using a classification algorithm. After reading, the separation device 1904 is placed into a waste container (see FIGS. 1, 15, item 1908).

Figure 28:
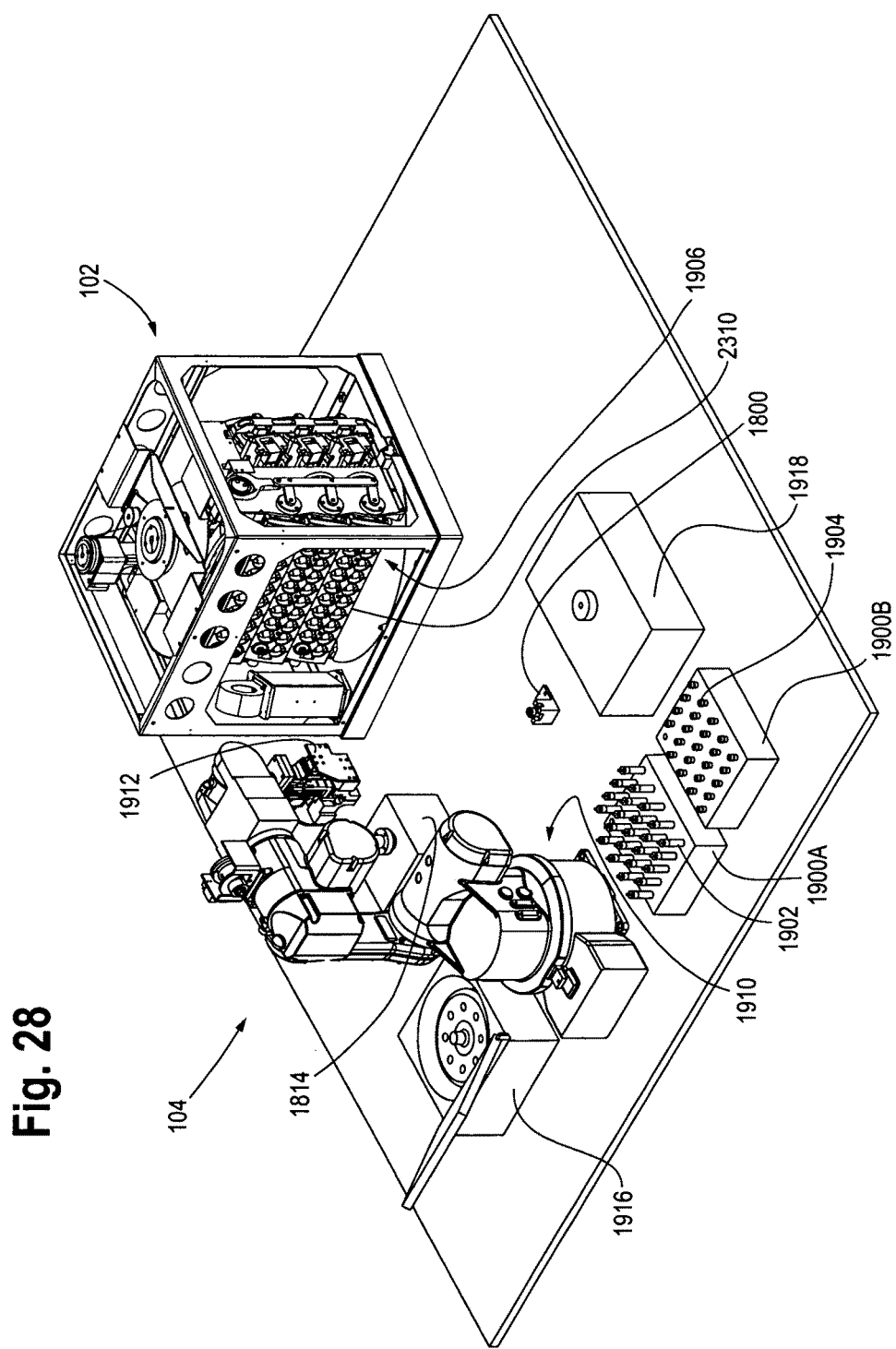
FIG. 28 is a perspective view of the instrument of FIG. 27, showing one possible configuration of the racks for holding the specimen containers. In the embodiment of FIG. 28, the racks include features for incubation of the specimen containers, agitation of the specimen containers, and automated detection of microbial growth within the specimen containers. Thus.

FIG. 28 is an illustration of an alternative arrangement for the identification instrument 104. In this embodiment, the walls or panels from the incubation enclosure are removed to show one embodiment of the racks 1906 that hold the bottles 500. The racks 1906 are incorporated into a rotating turret which rotates about a vertical axis. Detection instrumentation for noninvasively detecting whether a bottle is positive is incorporated in the racks 1906. These aspects are described in more detail in co-pending application Ser. No. 12/800,446, filed on the same date as this application, the content of which is incorporated by reference herein. Accordingly, in this embodiment the racks 1906 and associated detection instrumentation function as an automated detection system 102 for determining the presence of a microbial agent in a specimen container.

FIG. 29 is another perspective view of the embodiment of FIG. 27, showing the centrifuge 1916, vortexer 1814 and sample removal apparatus 1912 included in the robotic transfer mechanism 1910.

FIG. 30 shows the cassettes 1900A and 1900B of disposables in more detail. While each cassette is shown holding twenty-five disposable sampling devices 1902 or separation devices 1904, the number or arrangement of the devices 1902 and 1904 within a replaceable cassette 1900 is not important.

B. Robot Transfer Mechanism 1910 and Sampling Removal Apparatus 1912

Figure 31:
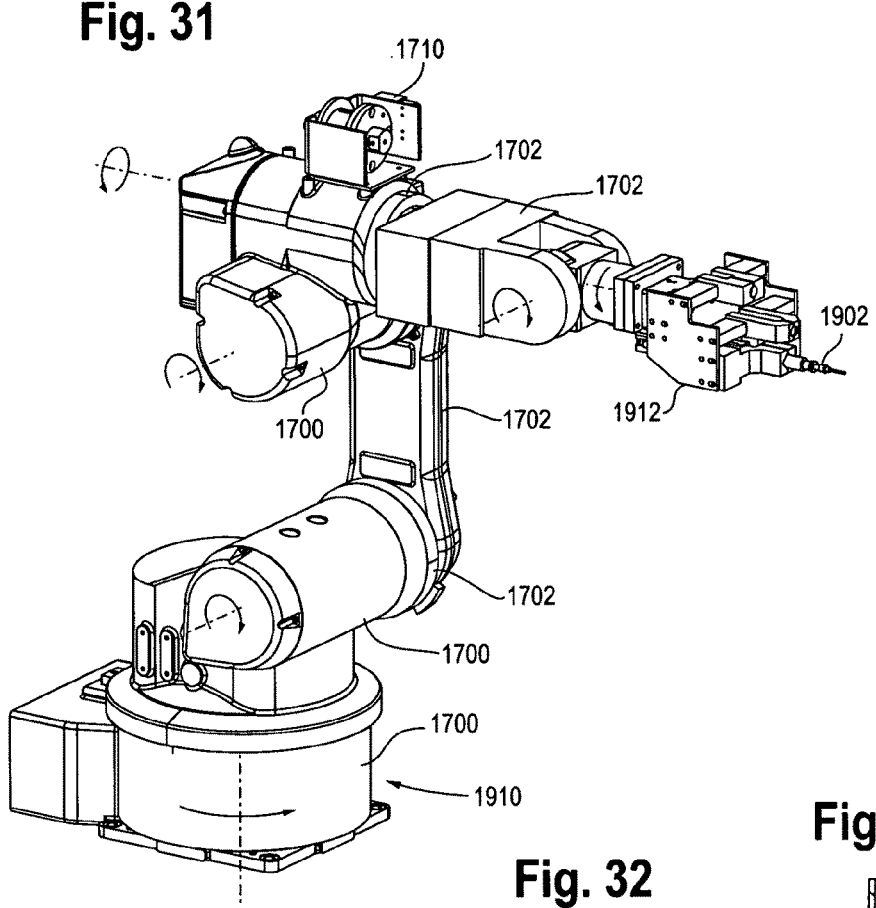
FIG. 31 is a perspective view of a multiple axis robot used in the embodiment of FIG. 29.

FIG. 31 is a perspective view of the robotic transfer mechanism 1910. The transfer mechanism 1910 is shown in a form of a six-axis robot. The robot includes six rotational joints 1700 indicated by the arrows and segments 1702 between the robot joints that expand or contract linearly in order to extend or contract or otherwise move the position of the sample removal apparatus 1912 placed at the tooling end of the robot arm in three-dimensional space. A rolling diaphragm pump assembly 1710 is fitted to the robot transfer mechanism 1910 to apply vacuum or positive pressure to the sampling device 1902 via a connecting tube 3402 to facilitate venting and sampling the containers 500 as described below. The pneumatic system 1914 (FIG. 1) provides pneumatic controls for the gripping tooling forming the sample removal apparatus 1912.

Figure 34:
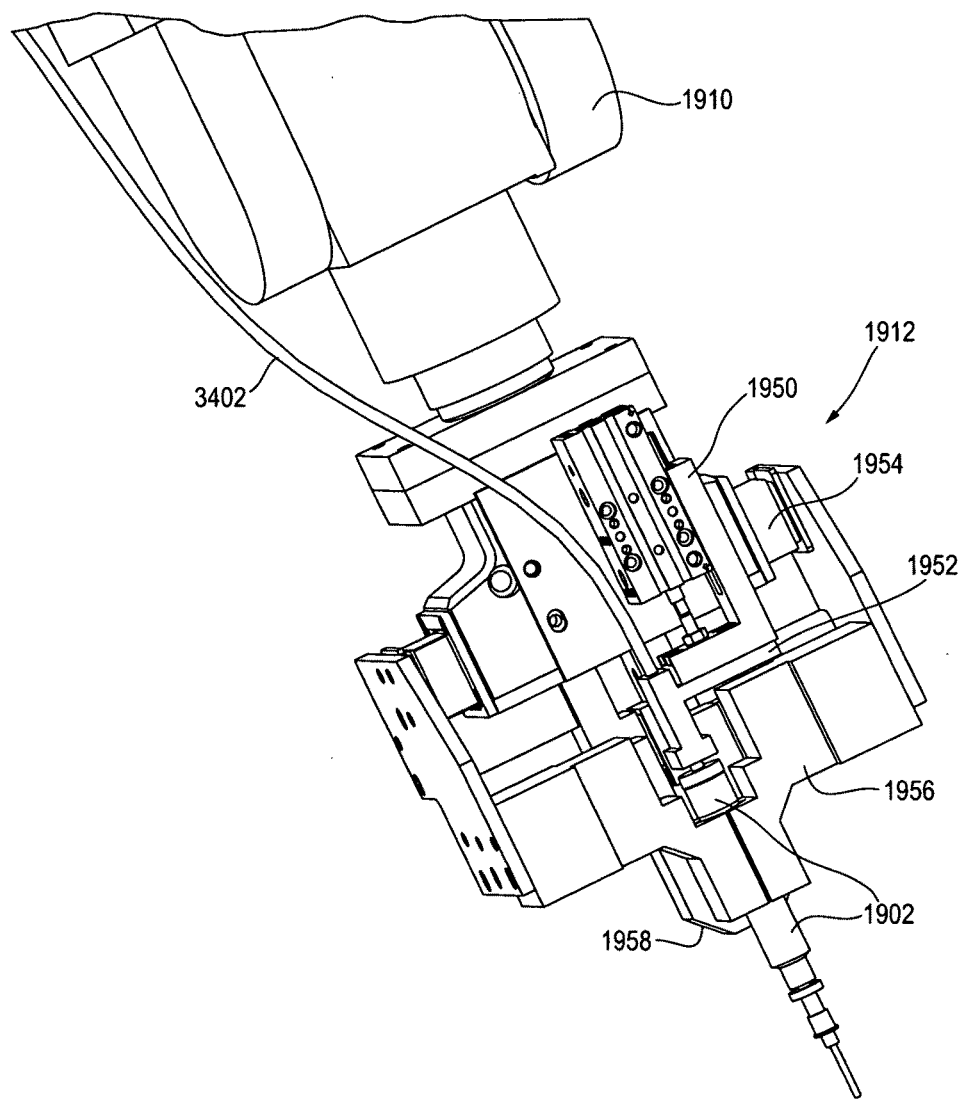
FIG. 34 is a detailed perspective view of the distal end of the arm of the robot of FIG. 31 shown gripping the sampling device of FIG. 32.
Figure 35:
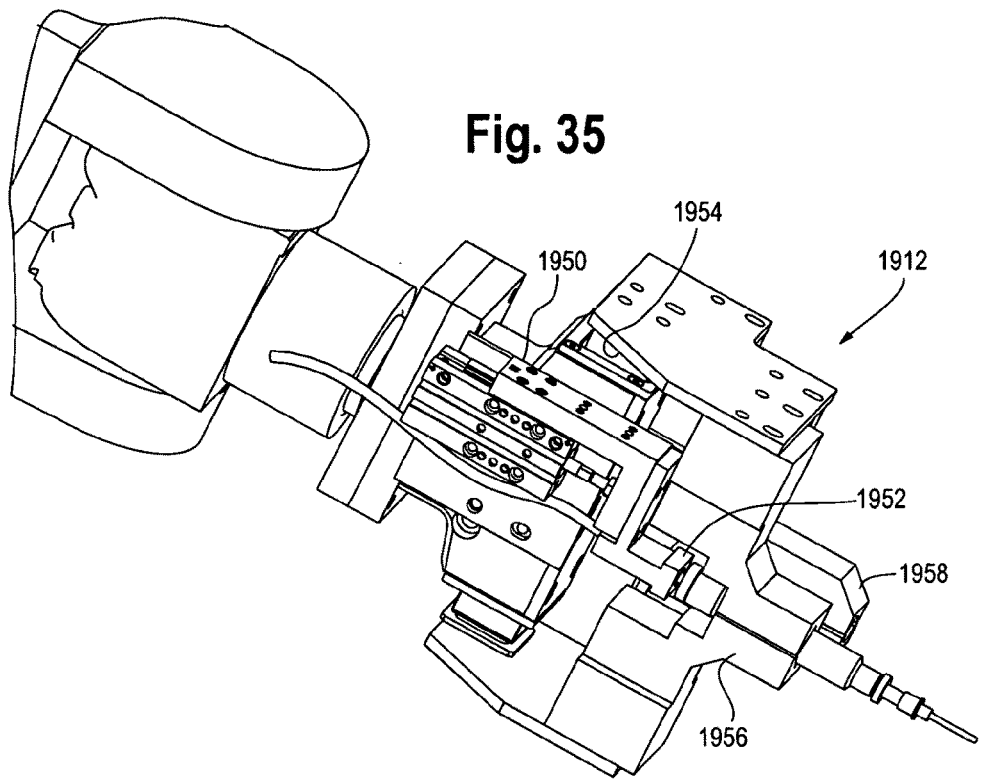
FIG. 35 is another detailed perspective view of the distal end of the arm of the robot of FIG. 31 shown gripping the sampling device of FIG. 32.

A six axes robot is chosen to allow for flexibility especially the ability to vent and sample the bottle. A pneumatic gripper 1954, see FIGS. 34 and 35, is placed at the tooling end of the robot on the last rotary joint. Plates attached to the gripper 1954 hold three end effectors; that is, there are three separate gripping components: one 1956 for the sampling device 1902, one 1958 for the separation device 1904 and specimen containers 500, and one (not shown) for a vacuum tube which may be used in future configurations. A connector 1952 is used to attach the free end of the tube 3402 to the fitting 3208 (FIG. 33) on the proximal end of the sampling device 1902. A pneumatically operated linear slide 1950 is moved forward to advance the connector 1952 to engage with the sampling device 1902 and backward to disengage from the sampling device when the device 1902 is deposited in the waste container.

Figure 36:
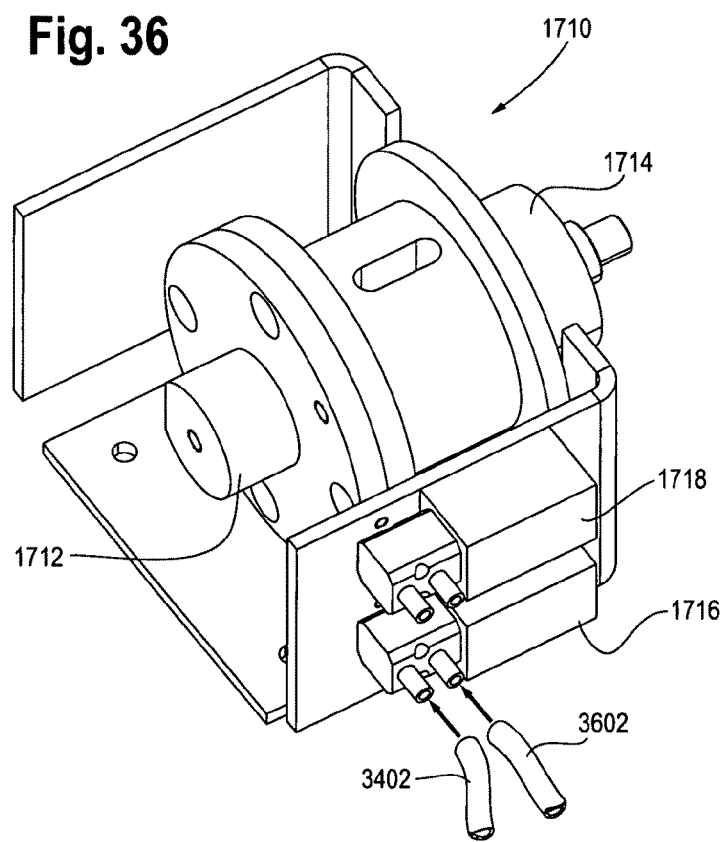
FIG. 36 is a perspective view of the pump assembly on the robot of FIG. 31 which operates to provide vacuum and positive pressure to the sampling device in order to (a) withdraw a small portion of the sample from one of the specimen containers and (b) dispense the sample (optionally after lysing the sample) into one of the disposable separation devices of FIGS. 6 and 30.

The gripper 1954 and linear slide 1950 are pneumatic driven, with the gripper and linear slide controlled from the same air line (3602 FIG. 36). Flow control valves (not shown) control the rate movement on the gripper and linear slide. When the sampling device 1902 is to be picked up, the gripping component 1956 is positioned around the sampling device 1902 with the component 1956 open and the linear slide 1950 retracted. An air valve (not shown) is activated to close the gripper 1954 and close the gripping component 1956 and advance the linear slide 1950. Through flow controls, the gripper closes first, grabbing the sampling device 1902. Shortly after, the linear slide 1950 advances and engages the connector (1952 in FIG. 34) with the sampling device 1902. Tubing 3402 connects the pump assembly 1710 with the connector 1952 in FIG. 34 and sampling device 1902, thereby establishing a connection from the sampling device 1902 to the pump 1710 (FIG. 36) via the tubing 3402.

C. Sampling Device 1902

Figure 33:
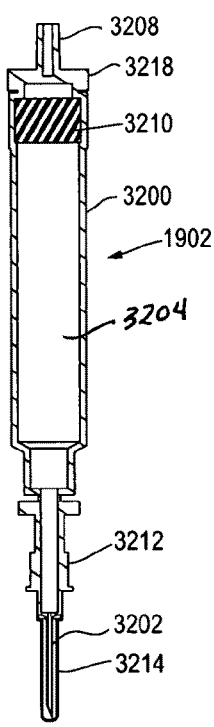
FIG. 33 is a cross sectional view of the sampling device of FIG. 32.

The sampling device 1902 in this embodiment is shown in FIGS. 32 and 33. The operation of the device 1902 for venting and sampling a specimen container 500 is described below in conjunction with FIGS. 36 and 37. The operation of the device 1902 for injecting the sample into the separation device 1904 is described below in conjunction with FIGS. 43-46.

Referring now to FIGS. 32 and 33, the sampling device 1902 includes a 18-gauge needle 3202 having a rubber sheath 3214. A luer fitting 3212 connects the needle 3202 to a 5 ml syringe body or tube 3200. A 0.2 μm hydrophobic filter 3218 is coupled to the syringe body 3200 with an elastomeric fitting 3210. A port or fitting 3208 receives the tube 3402 (FIG. 34) which is connected to the rolling diaphragm pump 1710 fitted on the robot transfer mechanism 1910 of FIG. 31.

The sheath 3214 has four functions: 1) sheath the needle 3202 to avoid needle stick injuries, 2) keep needle 3202 sterile, 3) prevent leaking of components out of tube 3200, and 4) act as spring to push back on components during sampling from the specimen container 500 and the injection of the separation device 1904 (see FIGS. 44 and 45). The sheath prevents the needle 3202 from sticking or binding to a septum or stopper fitted on the end of the specimen container 500. As the needle is withdrawn from the septum the rubber sheath pushes against the septum preventing the binding of the needle and septum. Similarly, during injection of the separation device the spring-like compression of the sheath 3214 pushes against the screw cap of the separation device 1904 and prevents the needle for sticking or binding to the cap.

The hydrophobic filter 3218 (FIG. 33) prevents microbes from contaminating the pumping system and tubing. Since this filter is hydrophobic, liquid is prevented from passing to the pump 1710 of FIG. 31. Another function of the filter besides preventing contamination, is repeatable fluid withdrawal. Once liquid touches the filter 3218 no more air can be evacuated from the tube 3200 since the water blocks the flow of air. Thus, the pump 1710 can continue pumping but the volume of liquid extracted will be a function of the tubing volume and not the precision of the pump.

D. Vacuum Pump Assembly 1710

The vacuum pump assembly 1710 of FIG. 31 is shown isolated in perspective view in FIG. 36. The pump 1710 contains a rolling diaphragm 1712 connected to a linear actuator 1714. Solenoid valves 1716 and 1718 switch the pump from input to output. During the venting step, in which the bottles 500 are vented to atmosphere using the sampling device 1902, the solenoid valves 1716 and 1718 are actuated to let positive pressure vent through the system (input). Also, during sampling the pump draws in fluid from the bottle 500 into the sampling device 1902. The fluid is ejected (output) to the separator device 1904 (FIGS. 43-44). For both input and output modes, the linear actuator 1714 continues to operate, moving the rolling diaphragm 1712 back and forth. Check valves (not shown in FIG. 36) take part in controlling the direction of the fluid.

E. Venting and Sampling

Figure 37:
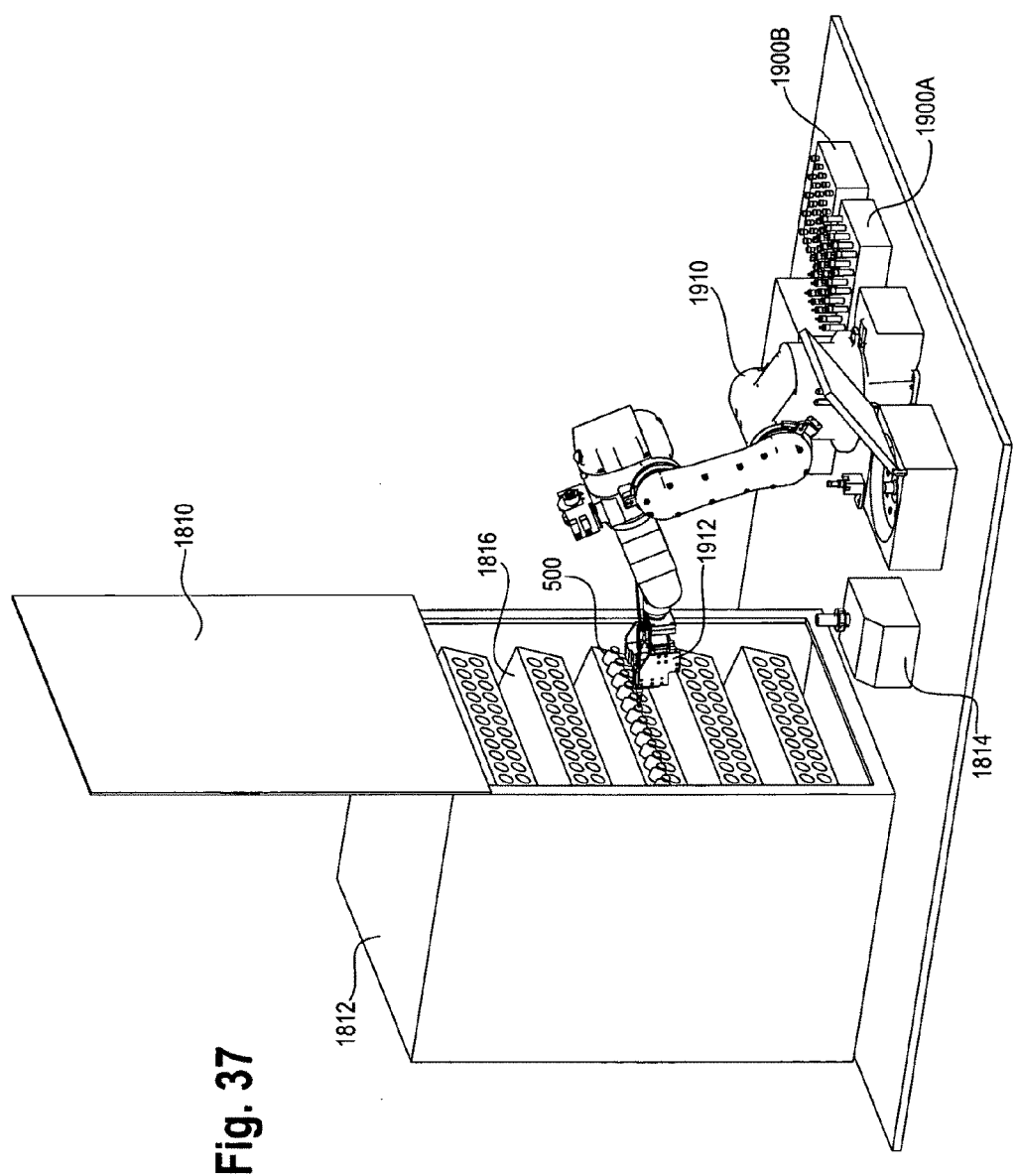
FIG. 37 is a perspective view of the robot of FIG. 31 performing a sampling operation on one of the specimen containers using the sampling device of FIG. 32.
Figure 38:
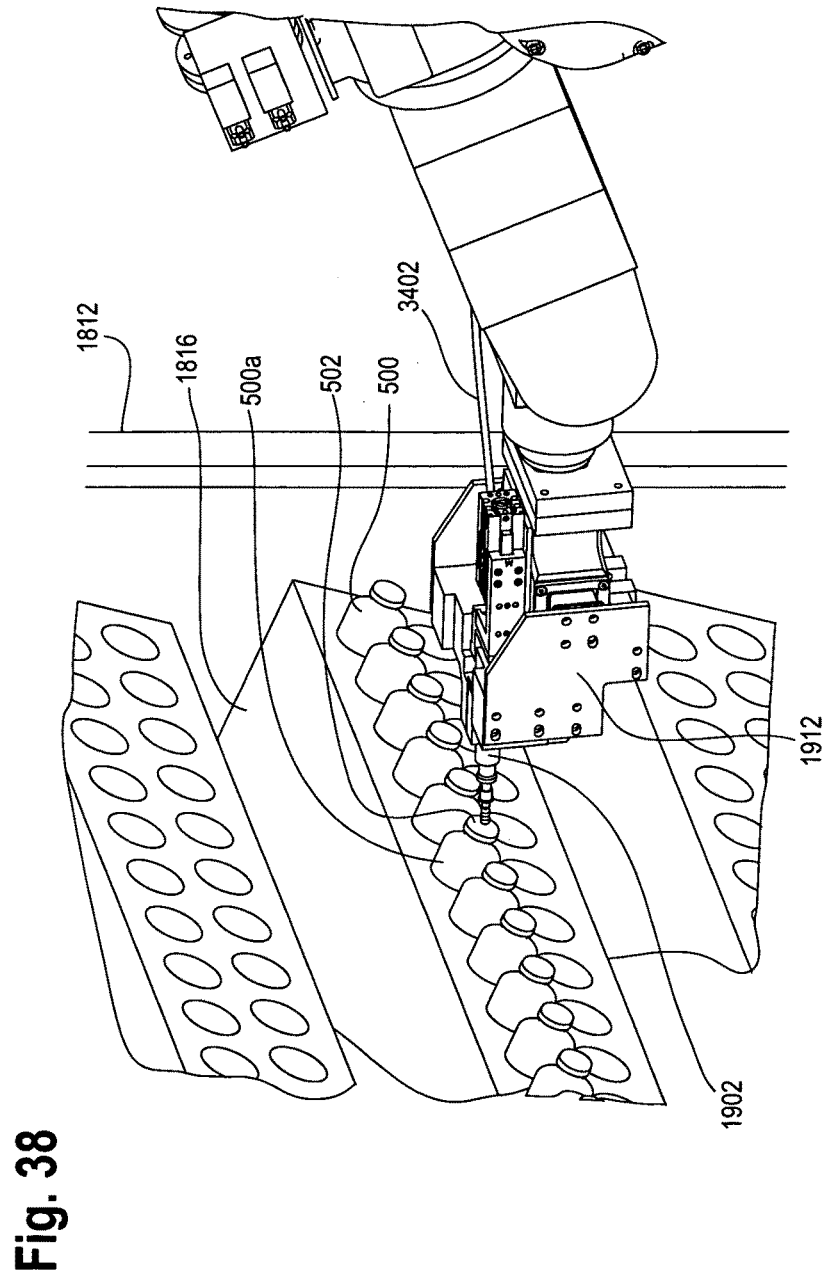
FIG. 38 is a more detailed view of the sampling operation shown in FIG. 37.

The venting and sampling steps are shown in FIGS. 37 and 38. The robot 1910 first picks up one of the venting and/or sampling devices 1902 from the cassette 1900A. The robot 1910 moves into the position shown in FIG. 37. The door 1810 is opened. The racks 1816 of FIG. 37 are rotated to an upwards pointing position and venting occurs by means of inserting the needle of the sampling device 1902 into the specimen containers 500. The racks 1816 are then rotated to a downward pointing position shown in FIG. 37 and the pump 1710 operated to draw a small volume of the sample (0.5 to 1.0 ml) from the specimen container 500 into the sampling device 1902. The sampling device 1902 is either pre-loaded with lytic agent or alternatively the lytic agent is added to the sampling 1902 prior to the venting and sampling steps. In the case where the sampling device is loaded with lytic agent in-situ, the robotic transfer mechanism grasps one of the sampling devices, accesses lytic agent solutions stored in containers 1802, 1804, 1806 etc., see FIG. 27, and withdraws 1.0 to 2.0 ml of lytic agent into the sampling device 1902 and then proceeds with the venting and sampling steps.

F. Mixing of Lytic Agent and Sample in Sampling Device 1902

As noted previously, the embodiment of FIGS. 27-46 includes features for mixing the test sample and lysis buffer, e.g., by vortexing the sampling device 1902 in order to mix the sample withdrawn from the specimen container with the lytic agent present in the sampling device 1902.

The vortexing will now be described in conjunction with FIGS. 29, and 39-42, showing the vortexer 1814. A unique feature of this system is a vortex cup 3900 which holds the sampling device 1902. The robotic transfer mechanism 1910 first places the sampling device 1902 in the vortex cup 3900 (see FIG. 39), releases the sampling device 1902, and then moves upward into the position shown in FIG. 40. The robot gripper fingers 3450 then closes loosely around the above the hydrophobic filter 3218 (FIGS. 32, 33) of the sampling device 1902. The sampling device 1902 is held loosely in the vortexer cup 3900 so that the vortexer 1814 can be free to agitate the sampling device 1902. If it is held tightly the vortexer 1814 is not free to agitate the sample/lysis buffer mixture which is present in the sampling device 1902. The bottom surface 1957 of the gripper tooling 1956 retains the sampling device 1902 in the vortexer 1814 during vortexing.

Figure 40:
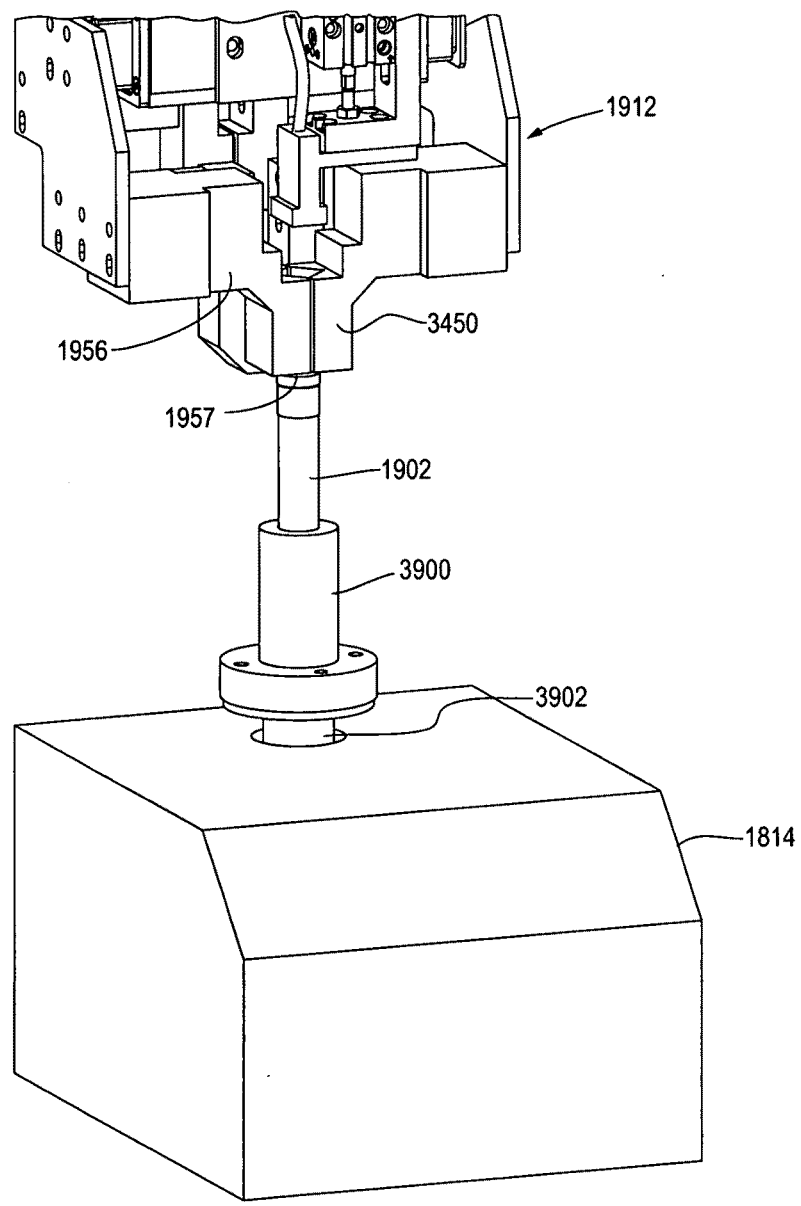
FIG. 40 is a perspective view of the sampling device of FIG. 32 being held by the robot hand during the vortexing operation.
Figure 41A:
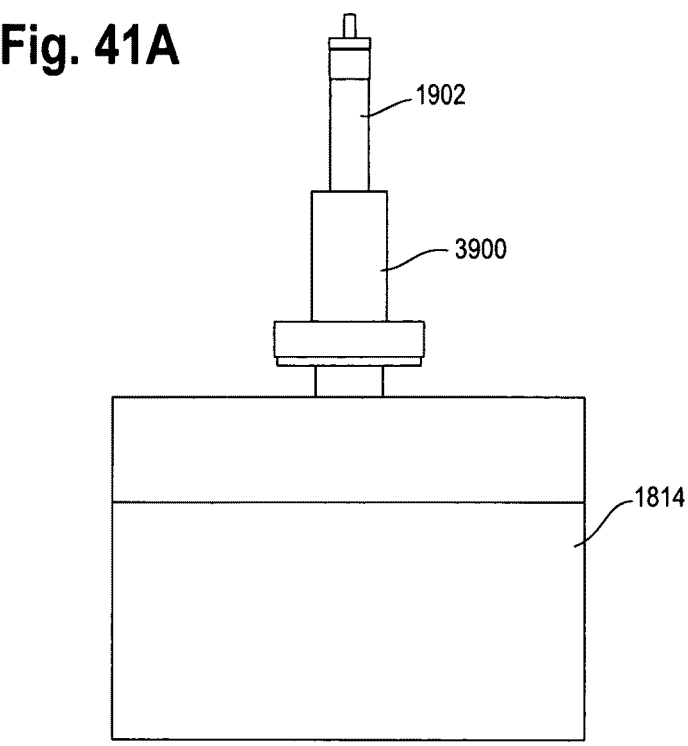
FIGS. 41A and 41B are side and cross-sectional views of the vortexer and sampling device.
Figure 41B:
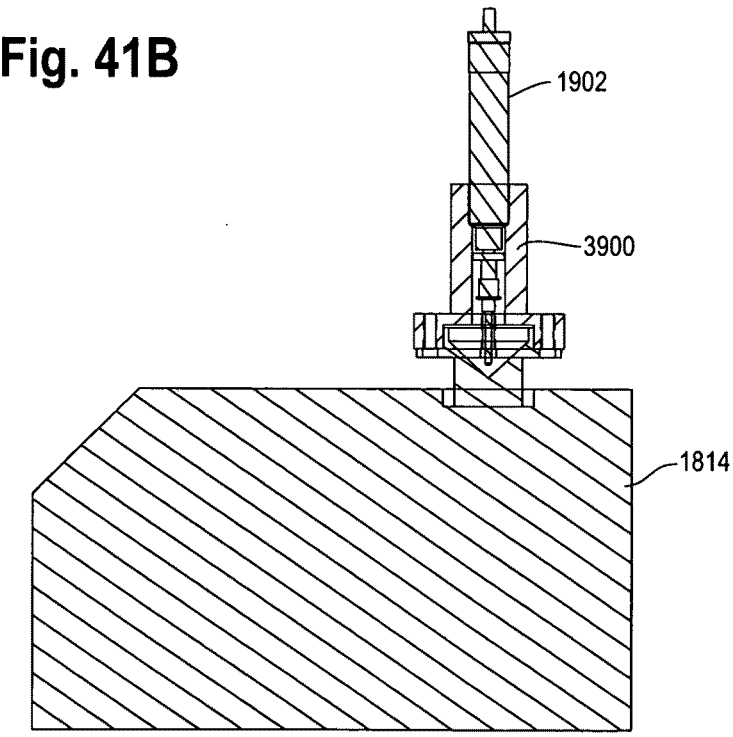
Figure 42A:
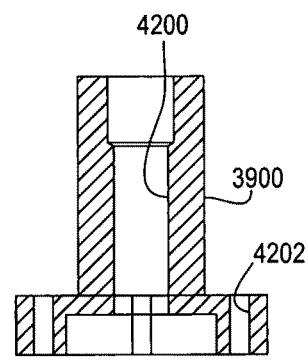
FIGS. 42A and 42B are cross-sectional and perspective views of a holder for the sampling device incorporated into the vortexer.
Figure 42B:
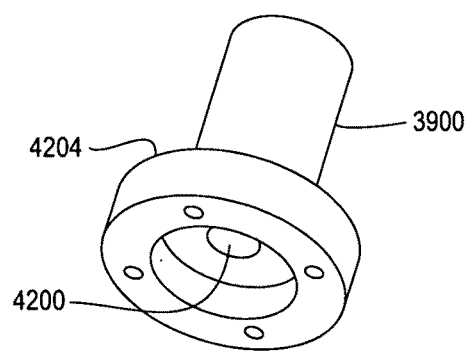

The vortexer 1814 includes a base 3902 that the cup or holder 3900 is mounted to as via fasteners extending through holes 4202 in the flange 4204 of the holder 3900 as shown in FIGS. 41-42. The interior channel 4200 of the holder 3900 is sized to fit the sampling device 1902 as shown in FIGS. 40 and 41. The vortexing sufficiently mixes the sample and the lysis buffer with a 5 second cycle at 3000 rpm.

Figure 39:
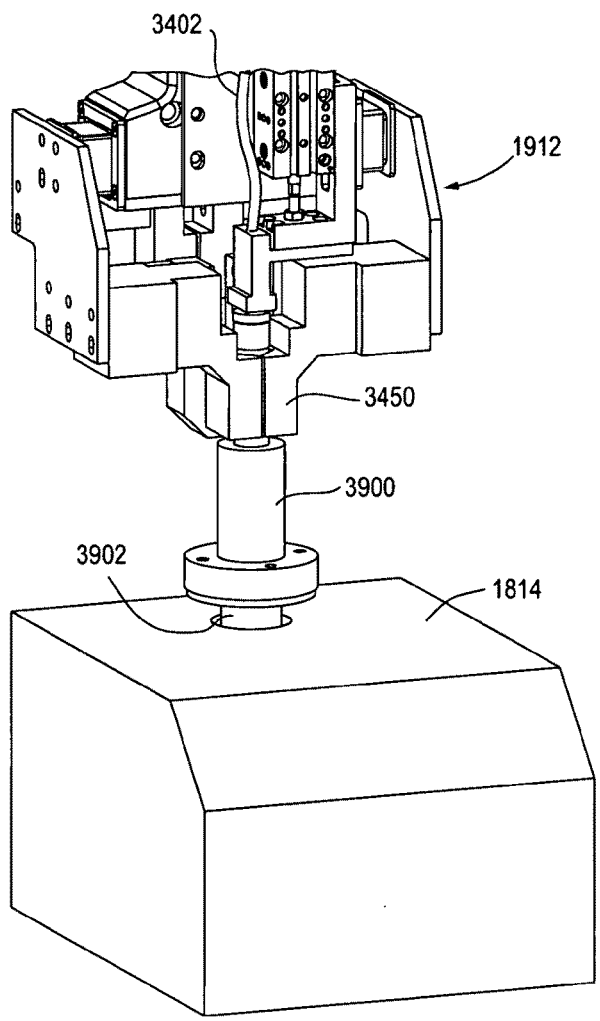
FIG. 39 is a perspective view of the sampling device of FIG. 32 being placed into a vortexer shown in FIGS. 26 and 27 in order to facilitate lysing of cellular components in the sample withdrawn from one of the specimen containers.
Figure 39A:
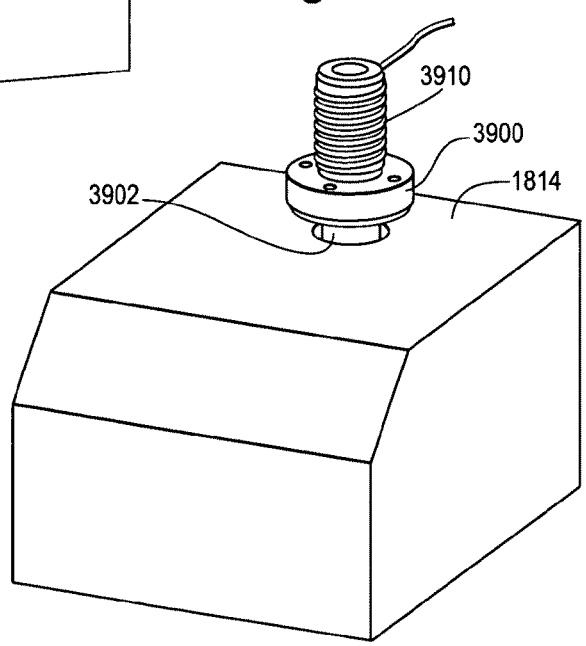
FIG. 39A is a perspective view of the vortexer having an optional coil heater around the holder of the sampling device in order to heat the holder and maintain the sample within the sampling device at 37 degrees C.

In one optional configuration, the vortex cup 3900 include heating elements to maintain the sample in the sampling device 1902 at 37 degrees C. The heating may take the form of a coil resistive heater 3910 shown in FIG. 39A. The agitation frequency, duration and temperature of the vortex process may change for particular samples and buffers.

G. Injection of Mixed Sample into Separation Device 1904

It may be desirable to first load the separation device into the centrifuge to pre-spin the lytic buffer and insure no trapped air is present in the capillary tube of the separation device. Also, if the optics system is configured in the centrifuge a quality check (e.g., a pre-read of the separation device before adding lysed sample) can be performed. Quality control checks could include inspection for debris or fibers that may be present in the separation device, scratches to the optic surfaces, or other optic defects.

After the vortexer 1814 completes the mixing of the sample and lysis buffer in the sampling device 1902, an approximately 1 ml portion of the mixed sample and lysis solution is then injected into the disposable separation device 1904. This operation may occur while the separation device 1904 is still contained within the cassette 1900B of FIGS. 26 and 27. The mixed sample and lysis buffer is shown as mixture 4302 in FIG. 43A. (FIG. 43D shows the rubber sheath 3214 shown partially removed from the needle 3202 but this is only to better illustrate the sheath and the needle; the needle is covered by the sheath during use as shown in FIGS. 43B and 43C).

Figure 43A:
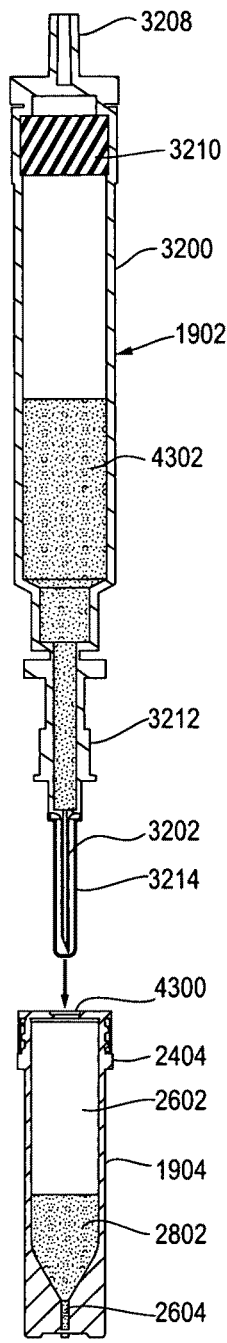
Figure 43B:
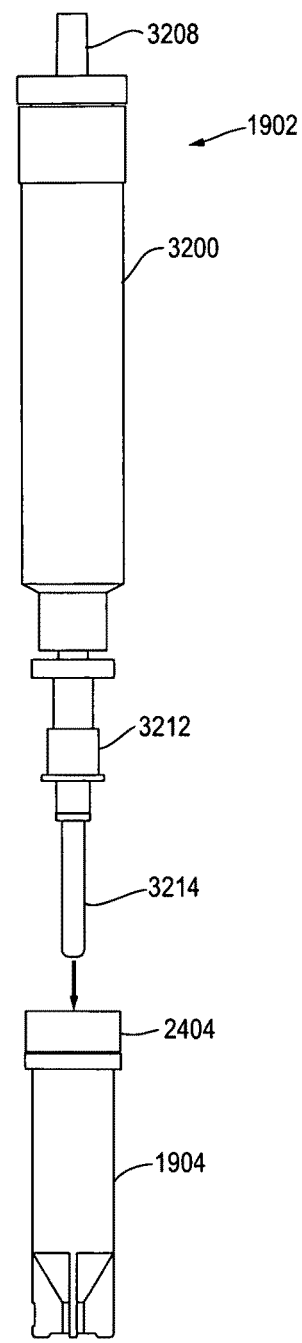
Figure 46:
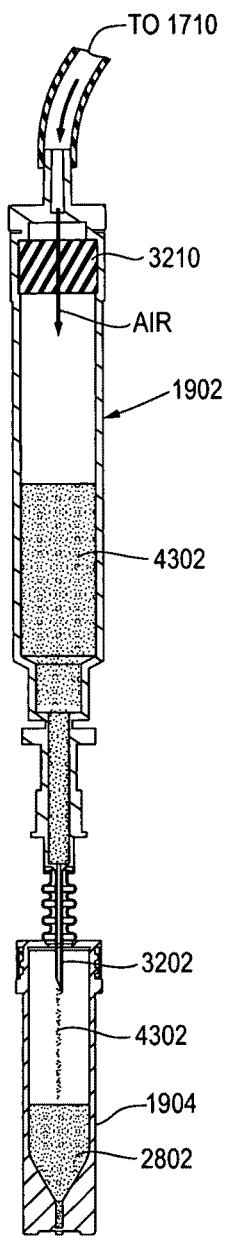
FIG. 46 is a cross-section view of the sampling and separation devices showing the injection operation.
Figure 46A:
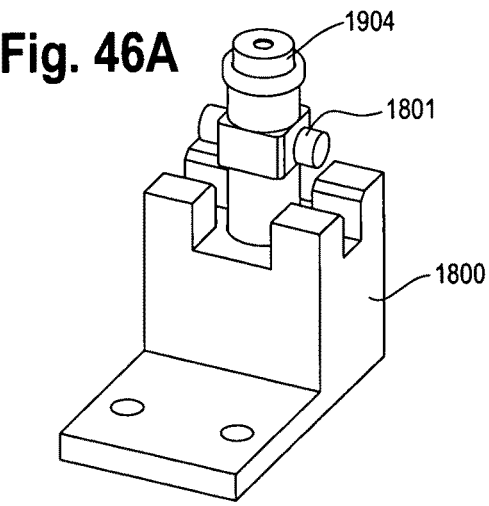
FIG. 46A is a detailed view of the cup and cup holder of FIG. 27, showing the cup receiving one of the separation devices.
Figure 46B:
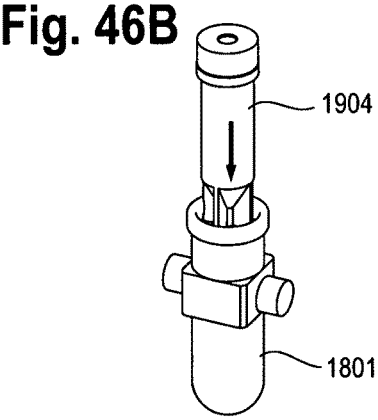
FIG. 46B shows a separation device being inserted into the cup of FIG. 46A.
Figure 46C:
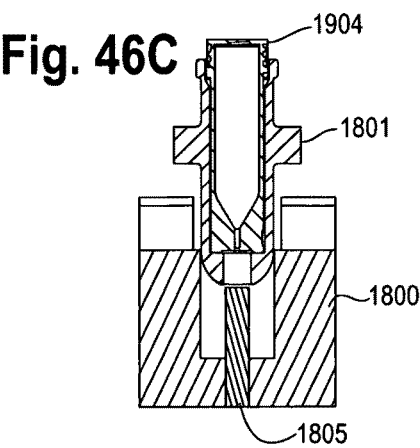
FIG. 46C is a cross-section of the cup holder, cup and separation device of FIG. 46A.

To accomplish the injection of the sample into the separation device 1902, the robotic transfer mechanism positions the (loaded) sampling device 1902 over one of the separation devices 1904 as shown in FIG. 43A and then proceeds to lower the sampling device 1902 so that the needle 3202 is forced through both the rubber sheath 3214 and the septum 4300 provided in the cap 2404 of the separation device 1904 so as to place the tip of the needle 3202 into the interior chamber 2602 of the separation device. See FIGS. 44, 45 and 46. This action compresses the rubber sheath 3214 as shown in FIGS. 44, 45 and 46, with the sheath 3214 acting on a spring and applying force to the cap 2404. As shown in FIG. 46, the roller diaphragm pump 1710 operates to pump air into the sampling device 1902, creating positive pressure in the interior of the sampling device and thereby forcing the test sample/lysis buffer mixture 4302 to be injected via the needle into the separation device 1904 as shown in FIG. 46. The mixture 4302 is dispensed on top of the 1.0 ml density cushion 2802 already present in the separation device 1904.

H. Transfer of Loaded Separation Device 1904 into Centrifuge 1916

After loading of the separation device 3202 in this manner, the robotic transfer mechanism 1910 proceeds to transfer the sampling device 1902 to a waste container, and then pick up the loaded separation device 1904 and place it in the cup 1801 held by the cup holder 1800 (FIG. 28, FIG. 46A-46C). Then, the combination of the cup 1801 and separation device 1904 is picked up and lifted off the holder 1800 (FIG. 46A) by the robotic transfer mechanism 1910 and placed in the centrifuge 1916 (FIG. 28) for separation and concentration of the sample in the separation device 1904.

In one possible embodiment, the centrifuge 1916 is not an indexed centrifuge, i.e., it does not come to the exact same position after spinning. The centrifuge lid is open and closed by a pneumatic cylinder. The position of the centrifuge is found by a camera (not shown) on the robot transfer mechanism 1910. A picture of the centrifuge is taken and machine vision software determines the position of the centrifuge so that the separation device 1902 can be correctly placed in the centrifuge. In particular, the camera looks for a fiducial mark on the rotor and the robot moves to the appropriate position in the centrifuge rotor. The separation device 1904 is inserted into the proper location to maintain balance in the centrifuge 1916.

The centrifuge could be configured to just spin one separation device at a time (as in the case of the first embodiment), or multiple devices at a time as shown in FIGS. 27-29.

The machine vision component (camera) could be eliminated by using an indexed centrifuge rotor. In this configuration, the centrifuge rotor would stop at the same position after centrifugation. This could be accomplished by using a mechanical clutch to engage the rotor and moving it past an optical sensor to the correct position. This method could eliminate complexities (e.g. lighting, complex software algorithms) and costs associated with machine vision, and thus for some implementations may be preferred.

I. Separation and Concentration of Microbial Agent in Separation Device 1904

The centrifuge operates to spin the separation device 1902 at high revolutions per minute for sufficient time to concentrate the microbiological specimen within the separation device into a pellet or pellet-like mass, as described in conjunction with the first embodiment, e.g., 10,000 g for 2 minutes. During centrifugation the lysed red blood cells separate to the top of the density cushion and the intact microbes form a pellet at the bottom of the 1 mm capillary tube 2604 in the separation device 1902 (see FIG. 43A). The centrifuge lid is opened using a pneumatic cylinder and the robot removes the separation device 1902 and cup 1801. The position of the capillary tube and holder is determined by machine vision as in the placement step above. The separation device 1902 and cup 1801 are removed as a unit from the centrifuge 1918 and placed on the cup holder 1800 (using pin 1805 as a locating mechanism, see FIG. 46C), and then the robot 1910 picks up the separation device 1902 and moves it to the reading unit 1918.

J. Reading of Concentrated Microbial Agent in Separation Device 1904

The reading unit 1918 interrogates the concentrated microbial agent forming the pellet within the separation device 1902. The details are not pertinent to this disclosure. The results (characterization and/or identification information for the microbial agent) are output to the user interface of the instrument, a connected workstation, a printer, or other output device depending on the configuration of the instrument.

K. Sterilization of Specimen Container 500 Stopper

In some biological applications for the present instrument 104, the specimen container 500 is inoculated with a specimen sample, such as human body fluids or other normally-sterile body fluids. This is accomplish by injecting the sample through a needle into a stopper formed at the top of the container 500. There is a chance that the sample may contain biohazardous material. Often a small drop of the sample, such as blood, may be left on the surface of the stopper. It is desirable to sterilize this surface before sampling and processing to avoid contamination of the container 500 with airborne or surface microbes.

Several methods could be developed to sterilize this surface in an automated manner. These include:

1) UV sterilization of the stopper surface. Ultraviolet light is a standard method of sterilizing surfaces. Automation could be accomplished by attaching a UV light source to a second robot or automation mechanism provided in the instrument that would move to the stopper surface for sterilization before venting the bottle or removing a test sample.

2) Misting the surface with a disinfectant such as isopropyl alcohol or other chemical and then wiping the surface clear. Presently this is the most common manual method of sterilizing inoculation sites. Normally, swabs are soaked in a disinfectant and a technician wipes the surface before inoculating the bottle or removing a sample. Mechanical wiping is necessary in the case of dried blood spots on the surface since a chemical mist may not penetrate through the blood. The misting of the surface can be automated by pressurizing a disinfectant reservoir with air and spraying this onto the surface of the stopper. The mechanical wipe can be accomplished by picking up a swab or fabric wipe and wiping the stopper surface. Other mechanical methods of wiping the surface include a rolling fabric soaked in the disinfectant. Again, these methods could be accomplished by means of a separate robotic mechanism in the instrument 104, or by providing the existing robot transfer mechanism 1910 with additional gripping/wiping/misting/UV sterilization components as the case may be.

L. Other Configurations for Robotic Transfer Mechanism 1910

While the second embodiment shown in FIGS. 27-29 uses a six-axes robot for the automation robot transfer mechanism 1910 to accomplish transfer and positioning of components or materials in the instrument, it is but one of a variety of choices that could be made and the scope of the present disclosure is intended to encompass other robotic transfer mechanisms. A multi-axis robot arm was chosen because it is flexible. New automation steps can be easily programmed without requiring major mechanical tooling redesigns. Once the process is established, the robot could be replaced by a simpler and more compact robot, with fewer axes, or a Cartesian (x,y,z) automation system. The Cartesian system would be more inexpensive than the six-axes robot. A Cartesian system is used for example in the first embodiment (see FIG. 5).

M. Electric Actuators

A few of the actuators of the second embodiment (and in particular the gripper and slide aspects of the sample removal apparatus 1912) are operated by pneumatics (compressed air). Pneumatic mechanisms are simple to program and design, however they are not amenable to clinical or some laboratory settings where compressed air is not available. These actuators can be replaced by electrical/mechanical systems such as linear drives, stepper and servo motor connected to linear drives and solenoids.

N. Alternative Mixing Methods

In the second embodiment, a vortexer 1814 is used to vigorously mix the sample and lytic buffer. A different mixing method such as sonication or reciprocal mixing could be used in place of vortexing.

O. Other Applications for Identification System

We have described in detail a method and instrument for automatically vent and sample a specimen container, e.g., blood culture bottle. The sample is lysed and centrifuged to process the microbial agent present in the sample for further analysis. The features of the instrument can be applicable to other diagnostic systems and other types of culture bottles. These systems could include molecular biology tests or automated culture bottles for industrial samples. Industrial samples could include sterility testing of drugs or food.

In the case of molecular biology tests it may be very important to perform a microbial test during exponential growth of a microorganism. During the exponential growth phase the genetic expression of microbes is different than during the lag phase. In the lag phase, which is prior to the exponential growth phase, microbes are converting their genetic machinery to express proteins to consume the media nutrients which may be different from their previous environment. As the microbes enter exponential phase the genetic expression has become set.

An automated detection instrument (102), such as that described here and in our prior provisional application or the BacT/ALERT® system, can determine when the microbes begin exponential phase and the automated identification method above can process a sample soon after exponential phase begins. In a manual culture method it would be difficult to determine when exactly the microbes enter into exponential phase since this would entail checking the bottles frequently for turbidity. Should the beginning of the exponential phase be missed by the technician, there is a risk that microbes would pass into death phase as the limited nutrients are consumed. Hence, in preferred embodiments the present identification instrument automatically processes the positive specimen containers soon or immediately after the container is deemed "positive."

In some other non-clinical embodiments of the identification system, the lysis step is optional or not preformed. Hence, the provision of a lytic buffer in the sampling device and vortexing the sampling device are not required in every possible configuration of the present inventive instrument.

P. Re-Sampling of Specimen Containers

The process of venting, sampling, separation and interrogation described above can be repeated on the same specimen container 500 as needed. In one possible variation, a given specimen container 500 is sampled successively using sampling devices 1902 loaded with different lytic buffers (e.g., loaded in situ from the supply of lytic buffers in the instrument) and loaded into different separation devices 1904 which are then subject to separation and concentration steps and then reading.

The instrument 104 may also perform identification and/or characterization testing without first performing the detection step; possibly shortening the time to identification. This mode of operation could be employed when other clinical data are available that are predictive of infection. Patient condition, biomarkers (e.g., PCT) etc. are examples of data that could be predictive of infection. In this mode, specimen containers are loaded into the identification instrument 104 (e.g., using the rack designs of either embodiment), the bottles are incubated in racks provided in the identification instrument, and every bottle is periodically sampled and subject to the separation and concentration step and the interrogation step. If a given sample is not able to be identified or characterized at the first iteration, the specimen container can be re-sampled, e.g., every 30 minutes, until sufficient microbial agent growth has occurred within the specimen container such that the reading step for that subsequent iteration returns an identification and/or characterization result. Incubation of the specimen container occurs prior to and during the sequential sampling of the specimen container.

Q. Coupling to Automated Detection Instrument.

In some embodiments, the automated identification instrument 104 of the first and second embodiments is tightly coupled to an automated detection instrument configured to determine whether a specimen container 500 is positive for presence of a microbial agent. This tight coupling preferably provides for automated hand-off of positive specimen containers 500 from a detection instrument to the automated identification instrument 104 as soon as the specimen container is tested "positive."

Figure 48:
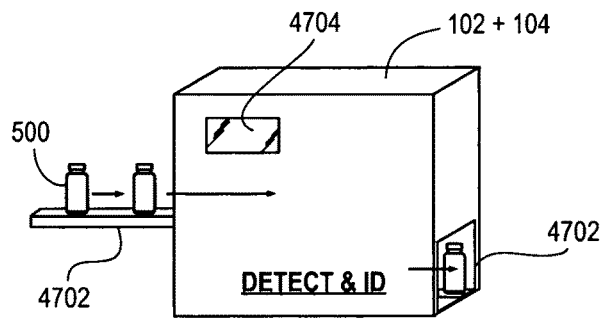
FIG. 48 is a schematic representation of a combined automated detection and identification instrument which receives specimen containers in an automated fashion e.g., via a conveyor.

A variety of instrument configurations for achieving such coupling are described in our prior U.S. provisional application Ser. 61/216,339 filed May 15, 2009. A few options are shown in FIGS. 47 and 48. In FIG. 47, an automated detection instrument 102 is linked via conveyer 4702 to the automated identification and/or characterization instrument 104. Bottles arriving at the automated identification and/or characterization instrument 104 are picked up by the robotic transfer mechanism 1910 and loaded into the racks. In FIG. 48, the bottles are provided to a combined detection and automated identification and characterization instrument (e.g., as set forth above for the second embodiment, see FIG. 28 and the above discussion). In this configuration, the racks holding the incoming specimen containers 500 include detection instrumentation for interrogating colorimetric sensors incorporated in the bottom of the bottles. Further, the combined instrument 102+104 is provided with incubation features, such as providing the incubation enclosure 1812 of FIGS. 27 and 37.

Figure 49:
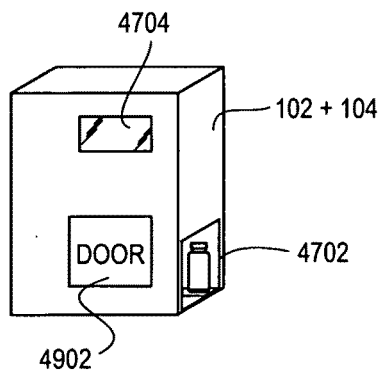
FIG. 49 is a schematic representation of a combined automated detection and identification instrument which receives specimen containers manually from a user, e.g., via opening a door in a front panel of the instrument. The embodiment of FIG. 49 could be implemented, for example, using the arrangement shown in FIG. 27.

Still other configurations are possible, as described in the co-pending application Ser. No. 12/800,467 filed on the same date as this application. FIG. 49 shows an embodiment in which the combined instrument 102+104 includes a door 4902 for manual loading of bottles into the racks of the combined detection and identification/characterization instrument.

In the embodiments of FIG. 47-49, a drawer 4702 is provided to provide access to remove waste from the instrument, e.g., specimen containers, sampling devices and separation devices.

The physical configuration of the external panels for the instruments of FIGS. 47-49 are not particularly important and can vary widely. The instruments include a graphical user interface and display 4704 which can also vary widely.

R. Computer System Schematic

Figure 50:
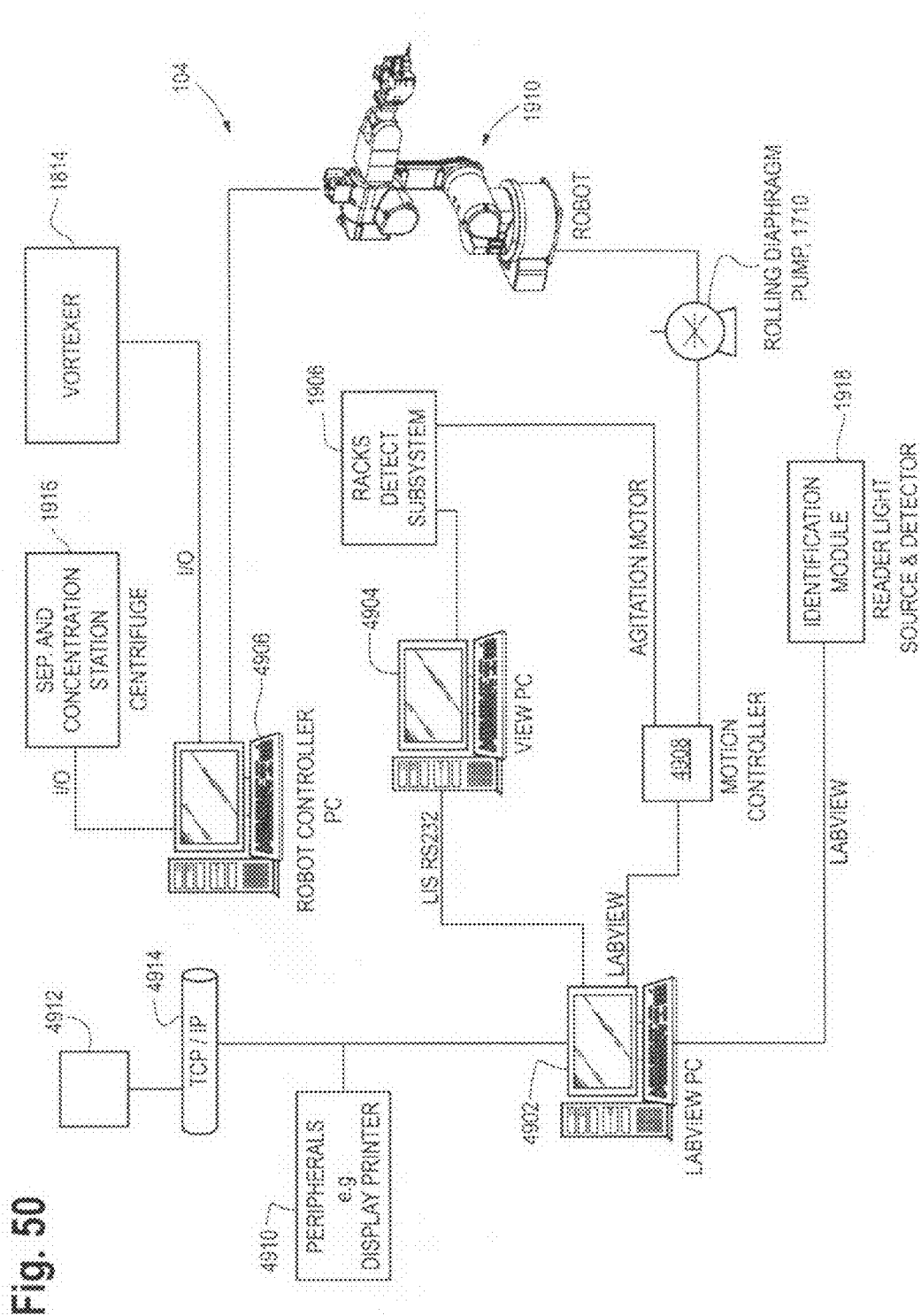
FIG. 50 is schematic block diagram showing a computer system controlling the operation of the instrument of FIGS. 27-46.

FIG. 50 is schematic block diagram showing the identification and/or characterization instrument 104 and its associated computer control system. The details shown in FIG. 50 can vary widely and are not particularly important, and therefore are provided here by way of example and not limitation.

A computer 4902 running LabVIEW (National Instruments) is connected to two computers: (1) a computer 4904 via a serial connection, and (2) a robot control computer 4906 via an Ethernet connection. The computer 4904 controls the racks 1906 and associated detection subsystem for detecting whether bottles are positive, controls the stepper motors which agitates (oscillates) the rack 1906 to provide agitation during incubation via a motion controller 4908. A stepper motor (not shown) allows for the rack to be precisely put in position for venting and sampling by the robot transfer mechanism 1910.

The LabVIEW 4902 computer queries the computer 4904 for positive bottles. The computer 4904 computer replies through the serial connection and the bottle ID, time of positive and bottle position are parsed by the LabVIEW computer 4902. The bottle position is sent to the robot controller 4906 which opens the door to the racks (FIG. 27, 1810) through a digital signal to a relay controlling pneumatic cylinders connected to the door. The robot 1910 acquires a sampling device 1902 and vents the bottle and samples as described above.

A digital signal from the robot controller 4906 is sent to relays to open and close the lid of the centrifuge 1916, start the centrifuge 1916 and control the vortexer 1816. Motion control of the linear actuator on the rolling diaphragm pump is controlled by the LabVIEW computer 4902 via a motion controller 4908.

Interrogation measurements (e.g., intinsic fluorescence measurements) aptured by the identification module 1918 are sent to the LabVIEW computer 4902. The computer 4902 compares the measured spectra with stored reference spectra from known samples to identify and/or characterize the microbial agent in the sample as described above. To do this comparison, the computer 4902 includes a memory (e.g., hard disk) containing the reference spectra data and machine-readable code storing software instructions to perform the comparison, e.g., the algorithms described previously. The computer 4902 includes a conventional central processing unit which operates on the acquired data and stored reference data using the algorithm(s) to generate a result for the sample under test and provides a report e.g., via a user interface on the instrument or attached peripherals 4910. The computer 4902 can communicate over an Internet Protocol network 4914 with other remotely located computers 4912, e.g., to share identification and/or characterization results, store the results in a remote database, or interface to other laboratory information systems.

S. Combination of Separation and Sampling Devices into a Single Disposable Device.

As described previously, the identification and/or characterization instrument 104 includes a sample removal apparatus 1912 which holds or grasps a disposable venting and/or sampling device 1902. Together, they operate to vent the specimen container and remove a portion of the biological sample in the positive detection container 500 and add the portion to a separation device 1904. The functions of vending and sampling could be performed by separate disposable devices 1902. Additionally, the functions of venting, sampling and separation could be performed in a single disposable device as described in this section.

Figure 52:
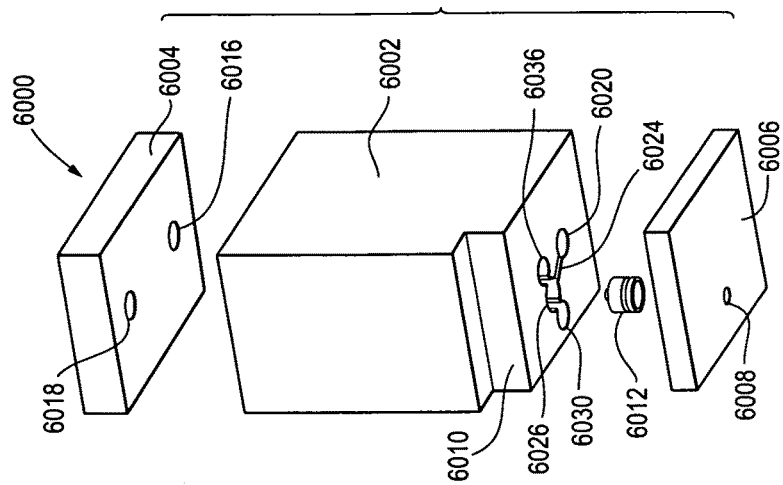
FIG. 52 is a perspective view of the separation device embodiment of FIG. 51, showing a top plate and base plate separated from the separation device.
Figure 51:
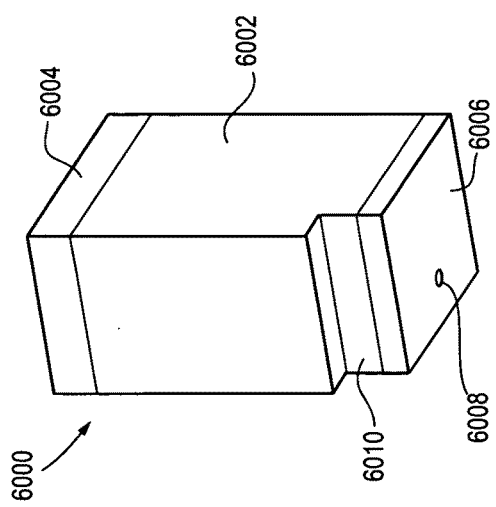
FIG. 51 is a perspective view of a second embodiment of a separation device which can be used in conjunction with the identification/characterization instrument of FIG. 1. The separation device of this embodiment has a separate lytic chamber and a separate separation chamber which are connected by a fluid flow-channel.
Figure 56:
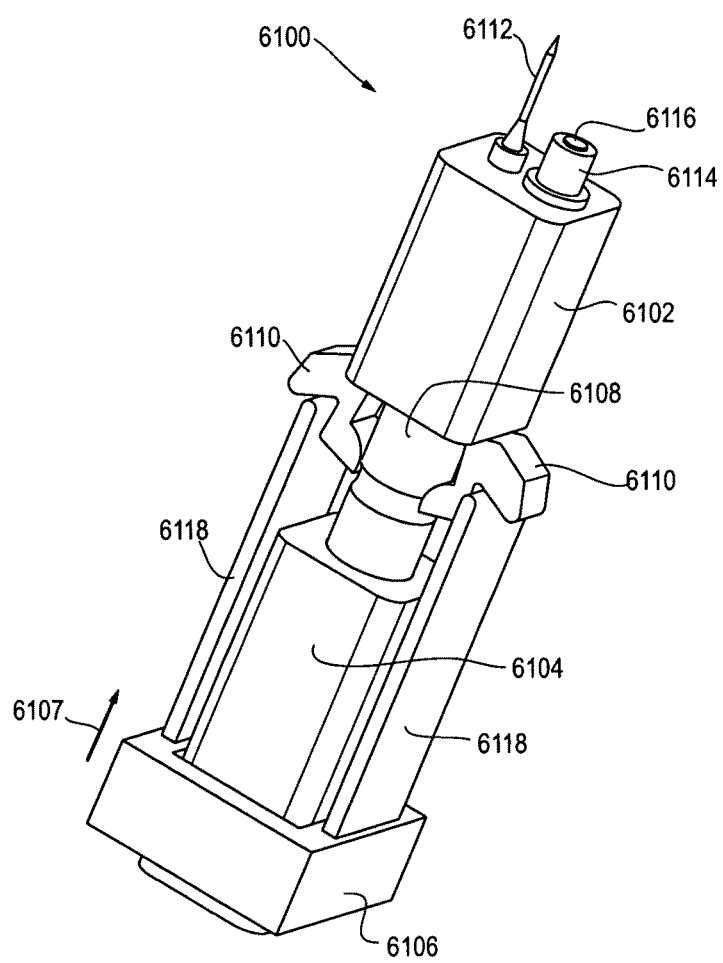
FIG. 56 is a perspective view of a combined sampling and separation device which can be used in conjunction with the identification/characterization instrument of FIG. 1.

Referring to FIGS. 51-55, a separation device 6000 includes a body 6002, generally in the shape of a block, a top plate 6004 and a base plate 6006. The body contains an optical window used for intrinsic fluorescence measurements; the material forming the window optically clear and non-fluorescing. In general, the body 6002 can be molded or otherwise formed from any known plastic material known in the art. As shown in FIGS. 53-55, the body 6002 of the separation device 6000 encloses a lytic chamber 6020, a venting channel 6030, a fluid transfer channel 6034 and a separation chamber 6040. The lytic chamber 6020 and separation chamber 6040 are orientated along two parallel and adjacent vertical axes 6022, 6042, defined in the body 6002, each chamber having top and bottom terminal ends. The venting channel 6030 provides a first fluid communication channel connecting the bottom end of the lytic chamber to a vent or pump port 6018 in the top plate 6004. As shown in FIGS. 54-55, the first fluid communication channel further comprises a venting fluid flow groove 6032 contained in the upper surface 6034 of the body 6002 and providing fluid communication between the lytic chamber 6020 and the venting channel 6030. The fluid transfer channel 6036 provides a second fluid communication channel connecting the bottom end of the lytic chamber 6020 to the top end of the separation chamber 6040 for transferring a lytic buffer and sample from the lytic chamber 6020 to the separation chamber 6040. As shown in FIGS. 54 and 56, the second fluid communication channel further comprises a venting fluid flow groove 6038 contained in the upper surface 6034 of the body 6002 and providing fluid communication between the lytic chamber 6020 and the separation chamber 6040. The lytic chamber 6020, venting channel 6030 and fluid transfer channel 6036 are open to a bottom surface 6010 of the body 6002 of the device 6000, as shown in FIG. 52. The bottom surface 6010 of the body 6002 may further comprise a lower fluid flow groove 6024 providing fluid communication between the bottom of the lytic chamber 6020 and the venting channel 6030 and fluid transfer channel 6036 through a valve well 6026 (described further below). The top plate 6004 and base plate 6006 can be attached to the body 6002 by any known means in the art to close of or otherwise seal the chambers 6020, 6040 and channels 6030, 6034. For example, the top plate 6004 and/or base plate 6006 can be affixed to the body by welding or by the use of an adhesive.

Figure 62:
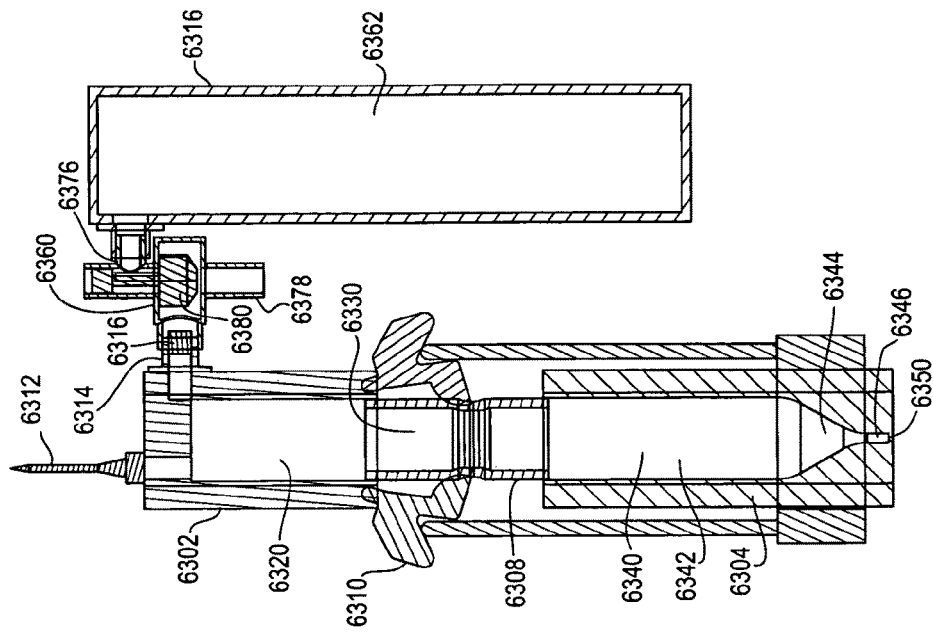
FIG. 62 is a cross-sectional view of the combined sampling and separation device shown in FIG. 61.

As shown in FIG. 52, the separation device 6000 includes a valve 6012 and a valve actuator port 6008 that runs through the top plate 6004. The valve 6012 is contained within a valve well 6026 in the bottom surface 6010 of the body 6002, and is operable between a first position and a second position via an external actuator (not shown). When the valve 6012 is in a first position, a first fluid communication channel is "open" from the bottom of the lytic chamber 6020 through the venting channel 6030 to the vent or pump port 6018. This open first fluid communication channel is operable to vent excess pressure from the device 6000 or to provide a vacuum to the lytic chamber 6020 through the use of a pump (not shown). When the valve 6012 is in a second position, a second fluid communication channel is "open" from the bottom of the lytic chamber 6020 through the fluid transfer channel 6036 to the separation chamber 6040. This open second fluid communication channel is operable for transferring the lytic buffer and sample from the lytic chamber 6020 to the separation chamber 6040. As shown in FIG. 62, the vent or pump port 6018 and sample entry port 6016 comprise open channels through the top plate 6004. In one possible embodiment, the sample entry port 6016 further comprises a pierceable septum (not shown). In another embodiment, a syringe needle (not shown) can be attached or affixed to the sample entry port 6016, thereby allowing the lytic and separation device to additionally operate as a venting and/or sampling device for directly obtaining a sample from a specimen container 500.

As shown in FIG. 54, the separation chamber 6040 may further comprise an upper reservoir, a middle tapered section and a lower capillary tube 6048 all arranged around a central vertical axis. As shown, the middle tapered section connects the wider diameter upper reservoir and the smaller diameter capillary tube 6048. In one embodiment, the bottom wall of the capillary tube 6048 is made of an optically transparent material for facilitating optical interrogation of a concentrated microbial agent (not shown) located at the bottom of the capillary tube 6048. In another embodiment, the separation device 6000 is made of an optically transparent material to facilitate optical interrogation of a concentrated microbial agent (not shown) located at the bottom of the capillary tube 6048. As shown, the bottom wall opposite the capillary tube 6048 may be of a reduced thickness to facilitate optical interrogation as indicated in FIG. 53. In yet another embodiment, optical interrogation can occur from the side of the device 6000. In accordance with this embodiment, the block will comprise a notch section 6010 and a reduced thickness side wall juxtaposed the capillary tube 6048. In accordance with this embodiment, the separation device 6000 is made of an optically transparent material to facilitate optical interrogation of a concentrated microbial agent (not shown) located at the bottom of the capillary tube 6048.

In operation, the lytic chamber 6020 can be loaded with a lysis buffer and a sample taken from a positive culture container. For example, a sampling device 1902, as described elsewhere herein, can be used to deposit separately or in combination a lysis buffer and a sample from a positive culture container into the lytic chamber 6020. In another embodiment, the lysis buffer can be added to the lytic chamber 6020 of the separation device 6000 within the characterization/identification subsystem. For example, the sampling device 1902 can be used to obtain an aliquot of lysis buffer (e.g., from a lysis buffer reservoir) that can be subsequently deposited into the lytic chamber 6020 through the sample entry port 6016 (e.g., a pierceable septum) in the body 6002. Next, the sampling device 1902 can be used to obtain a sample from a positive specimen container 500 and deposit that sample into the lytic chamber 6020 through the lytic chamber port 6016. The lysis buffer and sample are then mixed within the lytic chamber 6020, e.g., by agitation and/or vortexing of the sampling device 6000. The selective lysis step is allowed to proceed for a sufficient time to allow the lysis reaction to be substantially completed (e.g., from 1 to 5 minutes). This selective lysis step selectively lyses undesired cells (i.e., non-microorganism cells) that may be present in the sample, e.g., blood cells and/or tissue cells. In another embodiment, the lytic chamber 6020 can be pre-loaded with a lysis buffer and the sample loaded to the lytic chamber prior to agitation and/or vortexing. In one embodiment, the sampling device 6000 can optionally be incubated to allow the selective lysis step to proceed more quickly.

After the lysis step, the lysed sample and lysis buffer can be transferred to the separation chamber 6040 through the a fluid flow channel 6030 for the separation of any microorganisms over a pre-loaded a density cushion, as described herein. The valve 6012 is pressed down externally by a mechanical actuator (not shown), thereby opening the fluid flow channel 6030 between the lytic chamber 6020 and the separation chamber 6040. A pump above the separation chamber 6040 draws the mixture through the fluid flow channel 6030 to the top of the separation chamber 6040. In one embodiment, by holding the separation device 6000 at an angle; the fluid can flow gently down the interior wall of the separation chamber 6040 and onto the density gradient.

The identification/characterization instrument 104 further includes a separation and/or concentration station, optionally in the form of a centrifuge, which operates on the separation device 6000 so as to separate the microbial agent from other products in the portion of the biological sample and concentrate the microbial agent within the separation device 6000. In one example, the microbial agent is concentrated in the form of a pellet or pellet-like mass in the bottom of the capillary tube 6060 of the separation device 6000.

The identification/characterization instrument further includes a identification and/or characterization module or read station (see, e.g., FIG. 1, 1918) which interrogates the concentrated microbial agent to identify and/or characterize the microbial agent.

Another embodiment having a stacked chamber design is shown in FIGS. 59-69B.

FIGS. 55-60 illustrate a combined sampling and separation device 6100. As shown in FIGS. 55-56 and 59, the combined sampling and separation device 6100 includes an upper housing 6102, a lower housing 6104, and a flexible pinch valve 6108 connecting the upper housing 6102 and lower housing 6104. As shown in FIGS. 57 and 58, the upper housing encloses an upper lytic chamber 6120, the lower housing encloses a lower separation chamber 6140, and the flexible pinch valve 6108 defines a fluid transfer channel 6130 therethrough. The upper lytic chamber 6120, fluid transfer channel 6130 and lower separation chamber 6140 can be orientated around a central axis 6122.

The combined sampling and separation device 6100 further includes a pair of opposable compression tabs 6110, a valve actuator block 6106 and opposable actuator arms 6118 operable to "open" and "close" the flexible pinch valve 6110. In operation, the valve actuator block 6106 can be moved in a first direction (e.g., towards the compression tabs 6110, as represented by arrow 6107) to "open" the valve 6100. By moving the actuator block 6106 towards the compression tabs 6110 the actuator arms 6118 push up the compression tabs 6110 moving the compression tabs 6110 away from the flexible pinch valve thereby open the valve 6108. In the open position, the fluid flow channel 6130 is opened allowing fluid communication between the upper lytic chamber 6120 and the lower separation chamber 6140 (as shown in FIG. 58). The valve actuator block 6106 can also be moved in a second direction (e.g., away from the compression tabs 6110, as represented by arrow 6109) to "close" the valve 6108. When the actuator block 6106 is moved away from the compression tabs 6110 the actuator arms 6118 move the pair of opposable compression tabs 6110 to a "closed" position, thereby pinching closed the flexible pinch valve 6108 (as shown in FIG. 60).

As shown in FIGS. 56-57 and 59, the combined sampling and separation device 6100 also includes a syringe needle 6112 for obtaining a sample from a specimen container, and a vacuum port 6114 for pulling a vacuum within the lytic chamber 6120, thereby assisting with loading of the device 6100. Optionally the syringe may further comprise a sheath (not shown) to protect the syringe needle from damage and/or contamination. Also, as shown in FIGS. 56-57 and 59, the combined sampling and separation device 6100 includes a vacuum port 6114. The vacuum port will include a gas permeable filter or hydrophobic membrane 6116 that allows gases to pass but prevents contamination. In operation, the vacuum port can be connected to a pump (not shown) that can apply a vacuum to the sampling and separation device 6100 for the uptake of a sample from a positive specimen container.

As shown in FIGS. 58 and 60, the separation chamber 6140 includes an upper reservoir 6142, a middle tapered section 6144 and a lower capillary tube 6146 all arranged around axis 6122 below the lytic chamber 6120. As shown, the middle tapered section 6144 connects the wider diameter upper reservoir 6142 and the smaller diameter capillary tube 6146. In one embodiment, the bottom wall 6150 of the capillary tube 6146 is made of an optically transparent material for facilitating optical interrogation of a concentrated microbial agent (not shown) located at the bottom of the capillary tube 6146. In another embodiment, the separation device 6100 is made of an optically transparent material to facilitate optical interrogation of a concentrated microbial agent (not shown) located at the bottom of the capillary tube 6146. As shown, the bottom wall 6150 opposite the capillary tube 6146 may be of a reduced thickness to facilitate optical interrogation as indicated in FIGS. 58 and 60.

In operation, with the flexible pinch valve 6108 in the closed position, the lytic chamber 6120 can be loaded with a lysis buffer and a sample taken from a positive culture container. In one embodiment, the lysis buffer can be added to the lytic chamber 6120 of the separation device 6100 using the syringe needle 6112. For example, the syringe needle 6112 can be used to obtain an aliquot of lysis buffer (e.g., from a lysis buffer reservoir), depositing the lysis buffer into the lytic chamber 6120. Next, the syringe needle 6112 can be used to obtain a sample from a positive specimen container 500, depositing that sample into the lytic chamber 6120. The lysis buffer and sample are then mixed within the lytic chamber 6120, e.g., by agitation and/or vortexing of the sampling device 6100. The selective lysis step is allowed to proceed for a sufficient time to allow the lysis reaction to be substantially completed (e.g., from 1 to 5 minutes). This selective lysis step selectively lyses undesired cells (i.e., non-microorganism cells) that may be present in the sample, e.g., blood cells and/or tissue cells. In another embodiment, the lytic chamber 6120 can be pre-loaded with a lysis buffer and the sample loaded to the lytic chamber prior to agitation and/or vortexing. In still another embodiment, the sampling device 6100 can optionally be incubated to allow the selective lysis step to proceed more quickly.

After the lysis step, the lysed sample and lysis buffer can be transferred to the separation chamber 6140 through the a fluid flow channel 6130 for the separation of any microorganisms over a pre-loaded a density cushion, as described herein. To transfer the lysed sample and lysis buffer to the separation chamber 6140, the pair of opposable compression tabs 6110 are moved to the open position, thereby opening the flexible pinch valve 6108 and allowing fluid communication between the lytic chamber 6120 and the separation chamber 6140 through the fluid flow channel 6130. With the flexible valve 6108 in the open position, the lysed sample and lysis buffer will flow via gravity through the fluid flow channel 6130 and onto the density cushion (not shown) contained in the separation chamber 6140. In one embodiment, by holding the separation device 6100 at an angle, the fluid can flow gently down the interior wall of the separation chamber 6140 and onto the density gradient.

The identification/characterization instrument 104 further includes a separation and/or concentration station, optionally in the form of a centrifuge, which operates on the separation device 6100 so as to separate the microbial agent from other products in the portion of the biological sample and concentrate the microbial agent within the separation device 6100. In one example, the microbial agent is concentrated in the form of a pellet or pellet-like mass in the bottom of the capillary tube 6160 of the separation device 6100.

The identification/characterization instrument further includes a identification and/or characterization module or read station (see, e.g., FIG. 1, 1918) which interrogates the concentrated microbial agent to identify and/or characterize the microbial agent as described previously.

Figure 61:
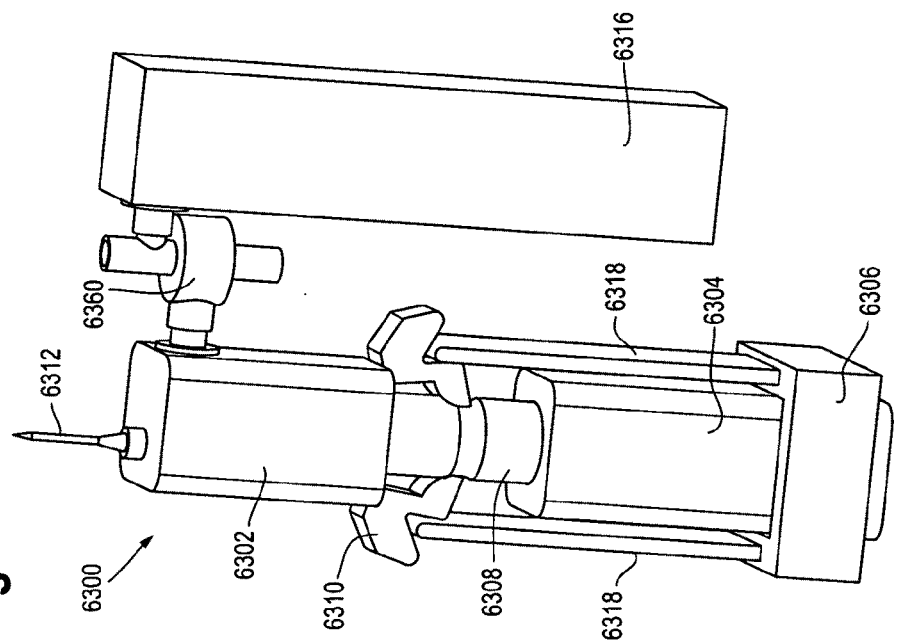
FIG. 61 is a perspective view of a second embodiment of a combined sampling and separation device.
Figure 67:
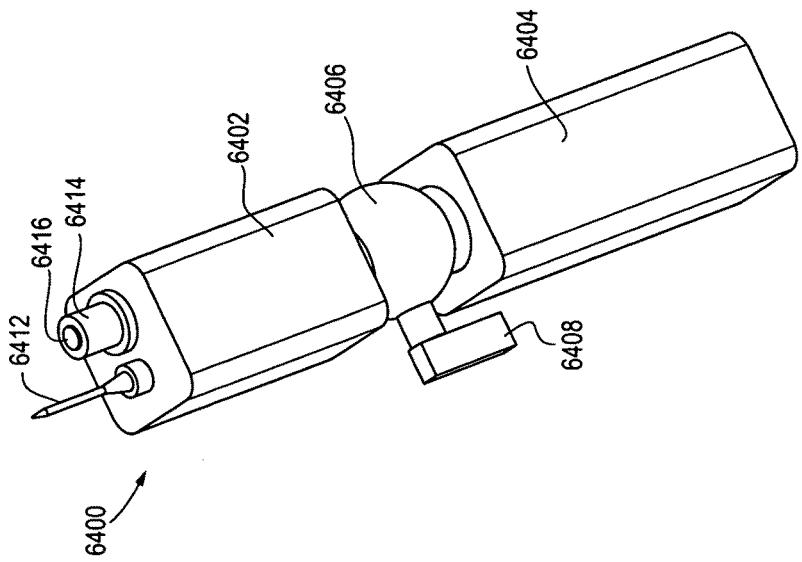
FIG. 67 is a perspective view of a third embodiment of a combined sampling and separation device which can be used in conjunction with the identification/characterization instrument of FIG. 1.

Another embodiment of the combined sampling and separation device 6300 is shown in FIGS. 61-63. Like the combined sampling and separation device shown in FIGS. 56-60, the combined sampling and separation device 6300 includes an upper housing 6302 enclosing a lytic chamber 6320, a lower housing 6104 enclosing a separation chamber 6340, and a flexible pinch valve 6308 defining therethrough a fluid transfer channel 6130.

The combined sampling and separation device 6300 further comprises a pair of opposable compression tabs 6310, a valve actuator block 6306 and opposable actuator arms 6318 operable to "open" and "close" the flexible pinch valve 6308. In operation, the valve actuator block 6306 can be moved in a first direction (e.g., towards the compression tabs 6310, as represented by arrow 6307) to "open" the valve 6308. By moving the actuator block 6306 towards the compression tabs 6310 the actuator arms 6318 push up the compression tabs 6310 moving the compression tabs 6310 away from the flexible pinch valve thereby open the valve 6308. In the open position, the fluid flow channel 6330 is opened allowing fluid communication between the upper lytic chamber 6320 and the lower separation chamber 6140 (as shown in FIG. 62). The valve actuator block 6306 can also be moved in a second direction (e.g., away from the compression tabs 6306) to "close" the valve 6308. When the actuator block 6306 is moved away from the compression tabs 6310 the actuator arms 6318 move the pair of opposable compression tabs 6310 to a "closed" position, thereby pinching closed the flexible pinch valve 6308 (not shown).

As shown in FIGS. 61-63, the combined sampling and separation device 6300 also comprises a syringe needle 6312 for obtaining a sample from a positive specimen container, a valve port 6314 for pulling a vacuum within the lytic chamber 6320, thereby assisting with loading of the device 6300. Optionally the syringe may further comprise a sheath (not shown) to protect the syringe needle from damage and/or contamination. The vacuum port will include a gas permeable filter or hydrophobic membrane 6116 that allows gases to pass but prevents contamination. The combined sampling and separation device further comprises a vacuum chamber, which is optionally pre-charged with a vacuum and operable connected to the sampling and separation device 6300 via a valve 6360 to apply a vacuum to the sampling and separation device 6300 for the uptake of a sample from a positive specimen container.

Referring to FIG. 63, the valve mechanism 6360 of this embodiment comprises a pump port 6370 that allows a pump (not shown) to operate the plunger 6380 between a vacuum position and a venting position. The valve 6360 further comprises an interior chamber 6374, a vacuum port 6376, and a venting port 6378. In operation, the pump (not shown) can move the plunger to a first position or a vacuum position (as shown in FIG. 65) thereby opening a fluid communication channel from said valve port 6372, through the interior chamber 6374 and through the vacuum port 6376 to the vacuum chamber 6362. In the first position or vacuum position, the valve 6360 allows a vacuum to be applied to the sampling and separation device 6300, thereby controlling the uptake of a sample from positive specimen container. The plunger 6380 can also be moved to a second position or venting position thereby opening a fluid communication channel from said valve port 6372, through the interior chamber 6374 and through the vacuum port 6378, thereby allowing the sampling and separation device to vent a specimen container prior to the uptake of a sample via the vacuum.

As shown in FIG. 62, the separation chamber 6340 may further comprise an upper reservoir 6342, a middle tapered section 6344 and a lower capillary tube 6346 all arranged around axis 6322 below the lytic chamber 6320. As shown, the middle tapered section 6344 connects the wider diameter upper reservoir 6342 and the smaller diameter capillary tube 6346. In one embodiment, the bottom wall 6350 of the capillary tube 6346 is made of an optically transport material for facilitating optical interrogation of a concentrated microbial agent (not shown) located at the bottom of the capillary tube 6346. In another embodiment, the separation device 6300 is made of an optically transparent material to facilitate optical interrogation of a concentrated microbial agent (not shown) located at the bottom of the capillary tube 6346. As shown, the bottom wall 6350 opposite the capillary tube 6346 may be of a reduced thickness to facilitate optical interrogation as indicated in FIG. 62.

As one of skill in the art would appreciate, the sampling and separation device 6300 of this embodiment operates in a similar manner as the sampling and separation device 6100 of the first embodiment. Accordingly, a detailed description of the operation of this specific embodiment is excluded. After the lysis step has been carried out, the sampling and separation device 6300 of this embodiment can be centrifuged for separation and/or pelleting of any microorganisms contained therein. The sampling and separation device 6300 of this embodiment may be pre-loaded with a lysis buffer and/or a density cushion.

Referring now to FIGS. 64-67, a third embodiment of a combined sampling and separation device 6200 is shown. The combined sampling and separation device 6200 includes an upper housing 6202, a lower housing 6204, and a rotary connection 6206 connecting the upper housing 6202 and lower housing 6204. As shown in FIG. 65, the upper housing encloses an upper lytic chamber 6220, the lower housing encloses a lower separation chamber 6240, and the rotary connection 6206 defines a fluid transfer channel 6130 therethrough. The upper lytic chamber 6220, fluid transfer channel 6230 and lower separation chamber 6240 can be orientated around a central axis 6222, as shown in FIG. 65.

In operation, the rotary connection 6206 can be rotated to an "open" position. In the open position, the fluid flow channel 6230 is opened allowing fluid communication between the upper lytic chamber 6220 and the lower separation chamber 6240 (as shown in FIG. 65). The rotary connection 6206 can also be rotated to a "closed" position to close the fluid flow channel 6230. As shown in FIG. 65, the fluid flow channel comprises an upper opening or channel 6232 through the upper portion of the rotary connection 6208 and a lower opening or channel 6234 through the lower portion of the rotary connection 6210. The rotary connection 6206 of this embodiment may further comprise a sealing gasket 6218 between the upper portion of the rotary connection 6208 and the lower portion of the rotary connection 6210, as shown in FIG. 66, to prevent leaks.

Figure 66:
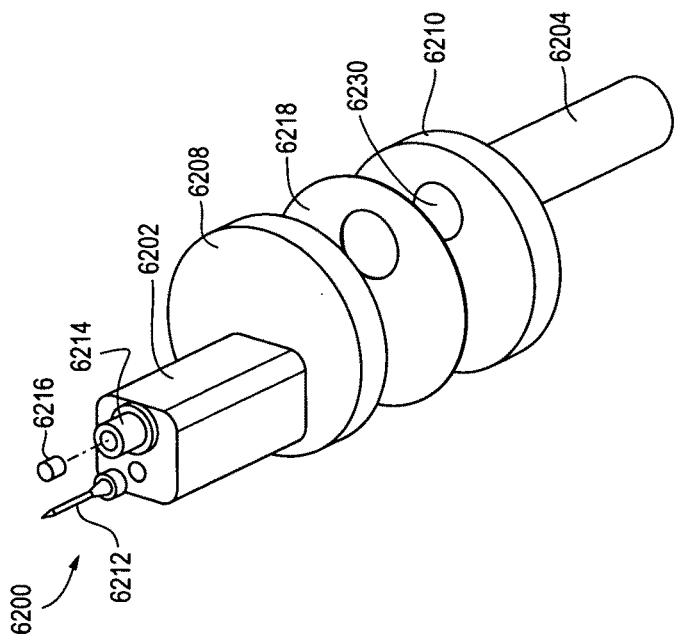
FIG. 66 is an exploded view of the combined sampling and separation device shown in FIG. 64.

As shown in FIGS. 64-66, the combined sampling and separation device 6200 also comprises a syringe needle 6212 for obtaining a sample from a positive specimen container, and a vacuum port 6214 for pulling a vacuum within the lytic chamber 6220, thereby allowing a sample to be loading into the lytic chamber 6260 of the device 6200. Optionally the syringe may further comprise a sheath (not shown) to protect the syringe needle from damage and/or contamination. The vacuum port 6214 will include a gas permeable filter or hydrophobic membrane 6216 that allows gases to pass but prevents contamination. In operation, the vacuum port 6214 can be connected to a pump (not shown) that can apply a vacuum to the sampling and separation device 6200 for the uptake of a sample from a positive specimen container.

As shown in FIG. 65, the separation chamber 6240 may further comprise an upper reservoir 6242, a middle tapered section 6244 and a lower capillary tube 6246 all arranged around axis 6222 below the lytic chamber 6220. As shown, the middle tapered section 6244 connects the wider diameter upper reservoir 6242 and the smaller diameter capillary tube 6246. In one embodiment, the bottom wall 6250 of the capillary tube 6246 is made of an optically transparent material for facilitating optical interrogation of a concentrated microbial agent (not shown) located at the bottom of the capillary tube 6246. In another embodiment, the separation device 6200 is made of an optically transparent material to facilitate optical interrogation of a concentrated microbial agent (not shown) located at the bottom of the capillary tube 6246. As shown, the bottom wall 6250 opposite the capillary tube 6246 may be of a reduced thickness to facilitate optical interrogation as indicated in FIG. 65.

As one of skill in the art would appreciate, the sampling and separation device 6200 of this embodiment operates in a similar manner as the sampling and separation device 6100 of the first embodiment. Accordingly, a detailed description of the operation of this specific embodiment is excluded. After the lysis step has been carried out, the sampling and separation device 6200 of this embodiment can be centrifuged for separation and/or pelleting of any microorganisms contained therein. The sampling and separation device 6200 of this embodiment may be pre-loaded with a lysis buffer and/or a density cushion.

Referring now to FIGS. 67-69B, another embodiment of a combined sampling and separation device 6400 is shown. The combined sampling and separation device 6400 includes an upper housing 6402, a lower housing 6404, and a rotary valve 6406 connecting the upper housing 6402 and lower housing 6404. As shown in FIGS. 68B and 69B, the upper housing encloses an upper lytic chamber 6420, the lower housing encloses a lower separation chamber 6440, and the rotary valve 6306 defines a fluid transfer channel 6430 therethrough. The upper lytic chamber 6420, fluid transfer channel 6430 and lower separation chamber 6440 can be orientated around a central axis 6422, as shown in FIGS. 68B and 69B.

In operation, the rotary valve 6406 can be rotated via a valve handle 6408 to an "open" position 6434 (see FIG. 79B). In the open position, the fluid flow channel 6430 is opened allowing fluid communication between the upper lytic chamber 6420 and the lower separation chamber 6440 (as shown in FIG. 69B). The rotary valve 6406 can also be rotated to a "closed" position 6434 (see FIG. 68B) to close the fluid flow channel 6430.

As shown in FIGS. 67-69B, the combined sampling and separation device 6400 also comprises a syringe needle 6412 for obtaining a sample from a positive specimen container, and a vacuum port 6414 for pulling a vacuum within the lytic chamber 6420, thereby allowing a sample to be loading into the lytic chamber 6460 of the device 6400. Optionally the syringe may further comprise a sheath (not shown) to protect the syringe needle from damage and/or contamination. The vacuum port 6414 will include a gas permeable filter or hydrophobic membrane 6416 that allows gases to pass but prevents contamination. In operation, the vacuum port 6414 can be connected to a pump (not shown) that can apply a vacuum to the sampling and separation device 6400 for the uptake of a sample from a positive specimen container.

As shown in FIGS. 68B and 69B, the separation chamber 6440 may further comprise an upper reservoir 6442, a middle tapered section 6444 and a lower capillary tube 6446 all arranged around axis 6422 below the lytic chamber 6420. As shown, the middle tapered section 6444 connects the wider diameter upper reservoir 6442 and the smaller diameter capillary tube 6446. In one embodiment, the bottom wall 6450 of the capillary tube 6446 is made of an optically transparent material for facilitating optical interrogation of a concentrated microbial agent (not shown) located at the bottom of the capillary tube 6446. In another embodiment, the separation device 6400 is made of an optically transparent material to facilitate optical interrogation of a concentrated microbial agent (not shown) located at the bottom of the capillary tube 6446. As shown, the bottom wall 6450 opposite the capillary tube 6446 may be of a reduced thickness to facilitate optical interrogation as indicated in FIGS. 68B and 69B.

As one of skill in the art would appreciate, the sampling and separation device 6400 of this embodiment operates in a similar manner as the sampling and separation device 6100 of the first embodiment. Accordingly, a detailed description of the operation of this specific embodiment is excluded. After the lysis step has been carried out, the sampling and separation device 6400 of this embodiment can be centrifuged for separation and/or pelleting of any microorganisms contained therein. The sampling and separation device 6400 of this embodiment may be pre-loaded with a lysis buffer and/or a density cushion.

From the above discussion, it will be appreciated that we have disclosed an apparatus for automated venting of a specimen container (500) having a closure (e.g., septum) sealing the interior of the specimen container from the environment, comprising:

a rack (e.g., FIG. 5, 1906) holding the specimen container 500;

a venting device (1902, FIG. 14, FIG. 32) having a needle 3202, a chamber 3202 in fluid communication with the needle and a port 3208 in fluid communication with the chamber (FIGS. 14, 32, 43A); (Note: the venting device may take the form of one of the combined separation and sampling devices shown in FIGS. 51-59 particularly if configured with a needle)

a robotic transfer mechanism (1910, FIGS. 1, 5, 247) moveable relative to the rack;

a sample removal apparatus (1912, FIGS. 1, 5, 15, 17, 27, 37, 38), attached to the robotic transfer mechanism having gripping features for gripping the venting device;

wherein the sample removal apparatus and robotic transfer mechanism are moveable relative to the specimen container so as to automatically insert the needle of the venting device through the closure of the specimen container to thereby vent the interior of the specimen container and obtain equilibrium between the interior of the specimen container and the atmosphere. (FIGS. 16, 38)

As discussed above, the rack is moveable between a first position wherein the specimen container is oriented in an upward orientation (FIGS. 16, 17) and a second position wherein the specimen container is oriented in a downward orientation (FIGS. 18, 19), and wherein the insertion of the needle of the venting device occurs while the rack is moved to the first position (FIGS. 16, 17).

As shown in the embodiment of FIG. 32A, the venting device 1902 may include a hydrophobic filter 3218 positioned within the venting device proximate to the port.

The apparatus further includes a pneumatic system 1914 (FIG. 1) coupled to the port 3208 of the venting device, e.g., as shown in FIGS. 14 and 34 (via tube 3402 connected to the vacuum pump 1710 of FIG. 31). Thus, the pneumatic system 1910 may include a tube 3402 having a first end connected to the port of the venting device (see FIG. 34) and a second end connected to a pneumatic pump (FIG. 36).

As discussed above, in some embodiments the venting device 1902 is loaded with a selective lytic agent (see FIG. 14). In some embodiments the venting device 1902 includes a sheath covering the needle (see FIG. 32, 43, sheath 3214). The sheath can be flexible (see FIGS. 44-46) and the flexible sheath covers a portion of the needle external to the specimen container during the venting of the specimen container (FIG. 38).

As noted above, the robotic transfer mechanism 1910 can take a variety of forms, including a multi-axis robot arm (see FIGS. 31, 37). Alternatively, the robotic transfer mechanism can take the form of a Cartesian robot moveable in at least two orthogonal directions relative to the rack 1906 (see FIG. 5). As shown in FIGS. 5 and 35, the sample removal apparatus can include gripping fingers (See 1956, FIGS. 34, 35). As shown in FIG. 34, the sample removal apparatus includes a slide 1952 coupled to the first end of the tube 3402, the slide moveable relative to the venting device 1902 to advance the first end of the tube 3402 over the port 3208 of the venting device 1902.

It will also be appreciated that we have described an apparatus for automated sampling of a specimen container having a closure sealing the interior of the specimen container from the environment, comprising: a rack 1906 holding the specimen container; a sampling device 1902 having a needle, a chamber in fluid communication with the needle and a port in fluid communication with the chamber; a robotic transfer mechanism 1910 moveable relative to the rack; a sample removal apparatus 1912 attached to the robotic transfer mechanism having gripping features for gripping the sampling device 1902; and a pneumatic system 1914 coupled to the port of the sampling device (e.g., via tube 3402); wherein the sample removal apparatus and robotic transfer mechanism are moveable so as to automatically insert the needle of the sampling device through the closure of the specimen container, the pneumatic system operative to draw a portion of a sample contained within the specimen container into the chamber of the sampling device via the needle. (FIGS. 15, 18, 19, 37, 38). (Note: the sampling device may take the form of one of the combined separation and sampling devices shown in FIGS. 51-69).

In one embodiment, the sample removal apparatus 1912 first inserts the needle 3202 into the specimen container while the specimen container is rotated to first, upward position to thereby vent the specimen container 500 and then withdraws the sample from the specimen container after the rack is rotated to a second, downward position.

An automated method for venting a specimen container in the form of a bottle having a closure sealing the interior of the specimen container from the environment has been disclosed comprising the steps of: holding the bottle 500 in a rack 1906 (FIG. 5); automatically and with the aid of robotic apparatus grasping a venting device having a needle, a chamber connected to the needle and a port connected to the chamber (FIGS. 14, 15); automatically moving the robotic apparatus so as to place the venting device in a position proximate to the bottle in the rack (FIGS. 16, 17); automatically inserting the needle of the venting device through the closure so as to place the needle into the interior of the bottle (FIG. 17), and bringing the interior of the specimen container to equilibrium with the atmosphere via the needle, chamber and port.

The method may include a step of moving the rack so as to place the bottle into an upward orientation and performing the automatic inserting step while the bottle is in the upward orientation, as shown in FIGS. 16 and 17. The method may also include the steps of moving the rack so as to place the bottle into a downward orientation; applying vacuum to the port of the sampling device; and drawing a portion of a sample contained within the bottle into the sampling device. (FIGS. 18 and 19).

In one possible configuration, the sampling device 1902 is loaded with a selective lytic agent prior to the drawing step (see FIG. 14, the device 1902 is either pre-loaded with the lytic agent or else the lytic agent is added from a container 1802 within the instrument 104, see FIG. 27, e.g., using the vacuum function of the pneumatic system 1914 and tubing 3402).

Figure 6:
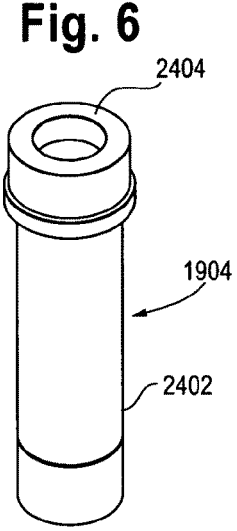
FIG. 6 is a perspective view of a separation device which is used in conjunction with the identification/characterization instrument of FIG. 1. The separation device receives a portion of the sample from a positive specimen container. The microbial agent is concentrated at the bottom of a capillary tube located in the separation device in the manner described herein. The concentrated microbial agent is then interrogated by a identification and/or characterization reading module to characterize and/or identify the microbial agent.
Figure 7:
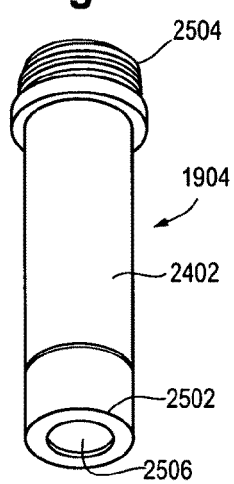
FIG. 7 is a perspective view of the separation device of FIG. 6.

In another aspect, an automated method for sampling a specimen container in the form of a bottle 500 having a closure sealing the interior of the specimen container from the environment is disclosed, comprising the steps of: (a) holding the bottle in a rack 1906; (b) automatically and with the aid of robotic apparatus 1910/1912 grasping a sampling device 1902 having a needle 3202 (FIG. 14, 32), a chamber 3204 connected to the needle and a port 3208 connected to the chamber; (c) automatically moving the robotic apparatus so as to place the sampling device in a position proximate to the bottle in the rack (FIGS. 6, 17); (d) automatically inserting the needle of the sampling device through the closure so as to place the needle into the interior of the bottle (FIG. 18-19, 38), and (e) applying vacuum to the port of the sampling device so as to draw a portion of a sample contained in the bottle into the sampling device.

The method may include a step of moving the rack so as to place the bottle into an downward orientation and performing the automatic inserting step while the bottle is in the downward orientation. (FIG. 18, 19). The method may further include the steps of moving the rack so as to place the bottle into an upward orientation; and wherein the step of inserting the needle of the sampling device is performed while the bottle is in the upwards orientation; and wherein the method further comprises the step of venting the bottle to atmosphere prior to the step of applying vacuum to the port of the sampling device. (FIGS. 16, 17).

In one embodiment, the method includes a step of loading the sampling device with a selective lytic agent prior to the step of inserting the needle of the sampling device through the closure of the specimen container, e.g., from a container 1802 of selective lytic agent (FIG. 27) at the time of use.

The sampling method may be repeated more than one time. Thus, in one aspect, the method may include the steps of repeating steps (b), (c), (d) and (e) more than one time on the same bottle.

As shown in FIGS. 44-46 the method may further comprise the step of injecting some or all of the portion of the sample within the sampling device into a disposable separation device 1902 used for separation and concentration of a microbial agent present in the sample.

The sampling method further include the step of lysing cellular components of the sample within the separation device 1904. The method may also include the step of centrifuging the sampling device 1902 to separate and concentrate a microbial agent within the sampling device. (As note above, the sampling device may take the form of one of the combined separation and sampling devices shown in FIGS. 51-69).

The sampling method may further include the step of incubating the bottle while the bottle is held in the rack, e.g., in the embodiment shown in FIG. 27-29 where the rack is positioned within an incubation enclosure 1812.

As used herein, the term "needle" is intended to be interpreted broadly to refer to a hollow spike-like element. That is, the needle 3202 (FIGS. 14, 33) on the sampling and/or venting device 1902 could take a variety of forms such as a plastic hollow spike.

Presently preferred and alternative embodiments of the inventive automated identification and/or characterization instrument have been described with particularity. However, persons skilled in the art will understand that variation from the details of the disclosed embodiments may be made. All questions concerning the scope of the invention are to be answered by reference to the appended claims.

We claim:

1. An apparatus for automated venting and sampling of a specimen container having a closure sealing the interior of the specimen container from the environment, comprising:
   a rack holding the specimen container;
   a supply of disposable venting and sampling devices, each of such disposable venting and sampling devices having a needle, a chamber in fluid communication with the needle and a port in fluid communication with the chamber;
   a robotic transfer mechanism moveable relative to the rack, the robotic transfer mechanism having a plurality of rotational joints;
   a sample removal apparatus attached to the robotic transfer mechanism having gripping features for gripping the disposable venting and sampling devices, wherein movement of the sample removal apparatus is controlled by the plurality of rotational joints of the robotic transfer mechanism; and
   a pneumatic system comprising a pump located on the robotic transfer mechanism and coupled to the port of the venting and sampling devices operative to draw a test sample contained within the specimen container into the chamber of the venting and sampling devices via the needle, the pneumatic system further comprising a first tube having a first end connected to the pump and a second end connected to the port of the venting and sampling devices, and a second tube having a first end connected to the pump and a second end connected to the gripping features;
   wherein the sample removal apparatus and robotic transfer mechanism are moveable relative to the specimen container so as to automatically insert the needle of the disposable venting and sampling devices through the closure of the specimen container to thereby vent the interior of the specimen container and obtain equilibrium between the interior of the specimen container and the atmosphere.

2. The apparatus of claim 1, wherein the rack is moveable between a first position wherein the specimen container is oriented in an upward orientation and a second position wherein the specimen container is oriented in a downward orientation, and wherein the insertion of the needle of the venting device occurs while the rack is moved to the first position.

3. The apparatus of claim 1, wherein the needle includes a flexible sheath and wherein the flexible sheath covers a portion of the needle external to the specimen container during the venting of the specimen container.

4. The apparatus of claim 1, wherein the robotic transfer mechanism comprises a multi-axis robot arm.

5. The apparatus of claim 1, wherein the robotic transfer mechanism comprises a Cartesian robot moveable in at least two orthogonal directions relative to the rack.

6. The apparatus of claim 1, further comprising a centrifuge device for separating and concentrating a microbial agent within the venting and sampling device.

7. The apparatus of claim 1, wherein the robotic transfer mechanism comprises six rotational joints.

8. The apparatus of claim 1, further comprising a selective lytic agent being loaded within the venting and sampling devices.

9. The apparatus of claim 1, wherein the sample removal apparatus further comprises a pneumatically operated linear slide configured to move forward to engage with the venting and sampling device, and configured to move backward to disengage from the venting and sampling device.

* * * * *